United States Patent
Goto et al.

(10) Patent No.: US 6,426,740 B1
(45) Date of Patent: *Jul. 30, 2002

(54) VISUAL-AXIS ENTRY TRANSMISSION APPARATUS AND METHOD THEREFOR

(75) Inventors: Hironori Goto; Masaaki Yoshida, both of Tokyo (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/140,761

(22) Filed: Aug. 26, 1998

(30) Foreign Application Priority Data

Aug. 27, 1997 (JP) ............................................. 9-244817
Mar. 13, 1998 (JP) ........................................... 10-082925

(51) Int. Cl.$^7$ ................................................ G09G 5/08
(52) U.S. Cl. ...................................................... 345/157
(58) Field of Search ................................. 345/157, 146, 345/171, 902, 158, 173, 7, 8, 9

(56) References Cited

U.S. PATENT DOCUMENTS 4,109,145 A * 8/1978 Graf ........................... 250/203

(List continued on next page.)

FOREIGN PATENT DOCUMENTS

| EP | 0596868 | 5/1994 | ............ G06K/9/58 |
| EP | 0714043 | 5/1996 | ........... G02B/27/02 |
| EP | 0743589 | 11/1996 | ............. G06F/3/00 |
| GB | 2281838 | 3/1995 | ............. G06F/3/00 |
| WO | 91-06263 | 5/1991 | ............. A61F/4/00 |
| WO | 93-14454 | 7/1993 | ............. G06F/3/00 |
| WO | 96/30822 | 10/1996 | ............. G06F/3/00 |

OTHER PUBLICATIONS

"Video See–through Design for Merging of Real and Virtual Environments", E. Edwards, et al., 1993 IEEE.

"The World through the Computer: Computer Augmented Interaction with Real World Environments", J. Rekimoto, et al., UIST '95, Nov. 14–17, 1995.

"Computer Interface to Use Head and Eyeball Movement for Handicapped People", Osamu Takami, et al., 1995 IEEE.

*Primary Examiner*—Richard Hjerpe
*Assistant Examiner*—Ronald Laneau
(74) *Attorney, Agent, or Firm*—Fitzpatrick, Cella, Harper & Scinto

(57) ABSTRACT

A visual axis entry transmission apparatus and method enables a physically handicapped person who can not depress a foot button to easily transmit the selection of a character to be input. 50 characters are displayed, via a display controller, on the liquid crystal device of a head-mounted display unit and on an external monitor. The visual axis position of a user is detected by a visual axis detection circuit, and a character at the visual axis position is obtained based on the detected visual axis position data. Selection character data for the past 100 selections are then updated. When the condition for the entry of a character is satisfied by this new character selection, the character is added to an input character string, and the newly input character is pronounced to notify the user that the character entry has been completed. The visual axis position data are employed to determine the detection result, such as a condition where the visual axis detection was successful, the visual axis detection failed, the eyes were blinking, or the same option was selected. In accordance with the result of the determination, the color of the selection frame for a character is changed to provide the user detection result information that represents the detection result condition, thereby confirming the results of a detection of a line of sight and avoiding having to unnecessarily repeat an operation.

123 Claims, 77 Drawing Sheets

U.S. PATENT DOCUMENTS

| | | | |
|---|---|---|---|
| 4,836,670 A | * 6/1989 | Hutchinson | 351/210 |
| 4,973,149 A | 11/1990 | Hutchinson | 351/210 |
| 5,579,048 A | * 11/1996 | Hirasawa | 348/333 |
| 5,583,795 A | * 12/1996 | Smyth | 364/571 |
| 5,621,424 A | 4/1997 | Shimada et al. | 345/8 |
| 5,644,324 A | * 7/1997 | Maguire, Jr. | 345/9 |
| 6,005,549 A | * 12/1999 | Forest | 345/157 |
| 6,094,182 A | * 7/2000 | Maguire, Jr. | 345/9 |

* cited by examiner

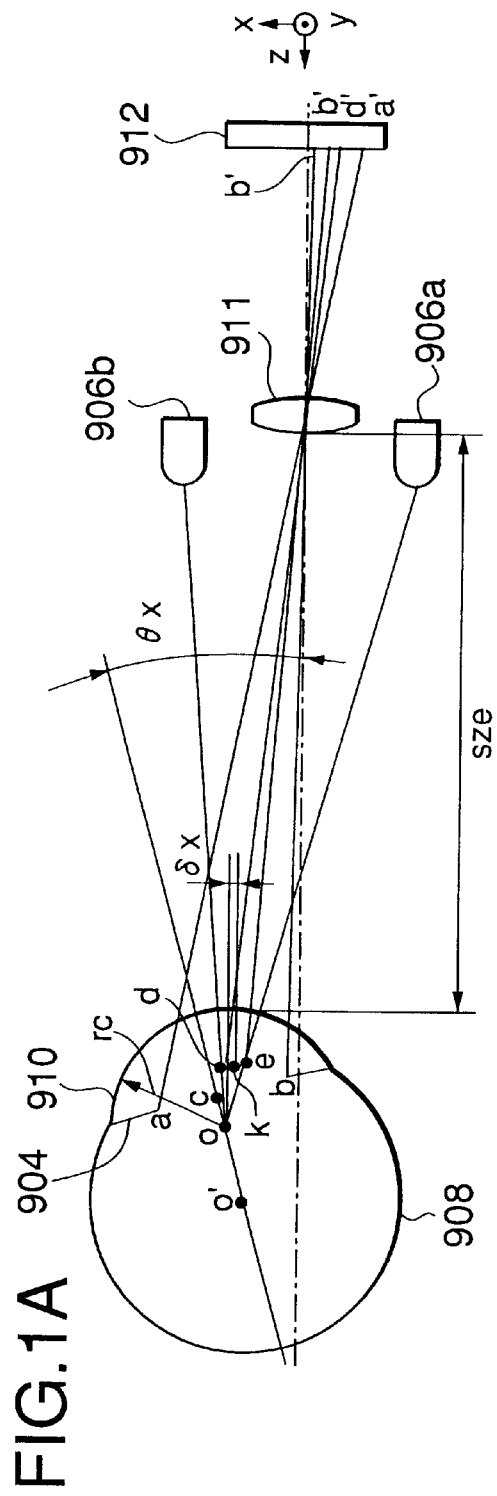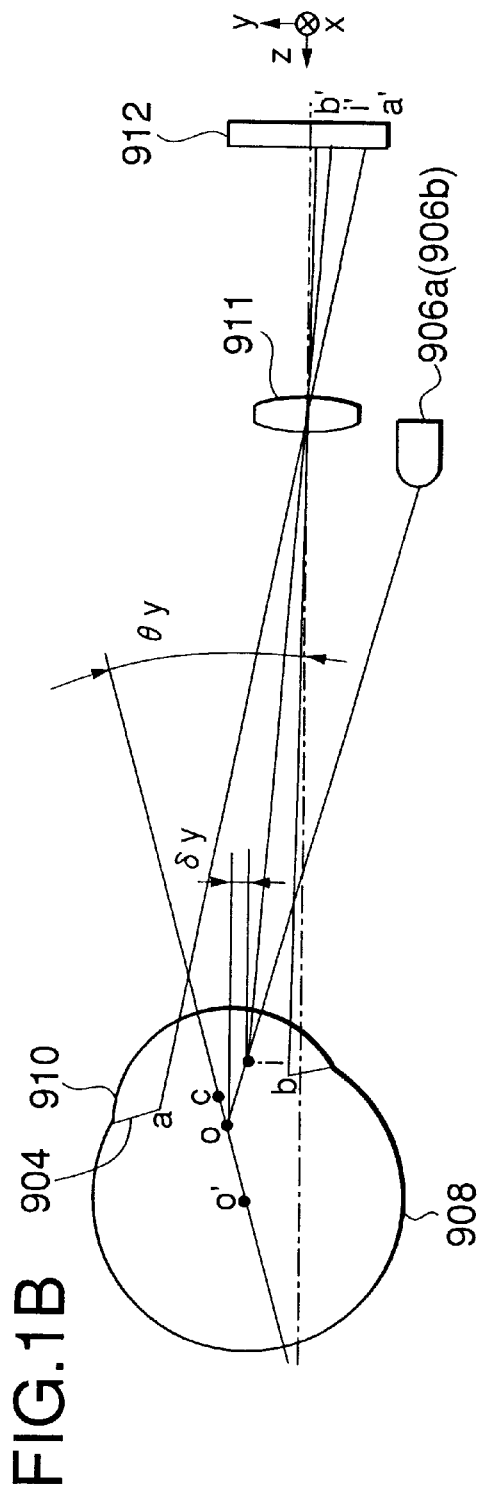

FIG.7

| CANCELLATION | FUNCTION | REGISTRATION | CALL | KATAKANA | ENGLISH CAPITAL LETTER | UTTERANCE |
|---|---|---|---|---|---|---|
| ー | RA | RI | RU | RE | RO | ◁ |
| 、 | WA |  |  | WO | N | < |
| 。 | A | I | U | E | O | > |
| BLANK | YA | YU | YO | TSU | . | ▽ |
| ▽ | CLEAR | PRECEDING LAST CHARACTER DELETION | DELETION | YES | NO | △ |

GOOD AFTERNOON ■

| COMMUNICATOR EYE CONTROL | | | | | | – | □ | × |
|---|---|---|---|---|---|---|---|---|
| FILE(F) EDITING(E) WINDOW(W) HELP(H) | | | | | | – | □ | × |
| CANCELLATION | FUNCTION | REGISTRATION | CALL | KATAKANA | ENGLISH CAPITAL LETTER | UTTERANCE | | |
| – | A | I | U | E | O | ◁ | | |
| ' | KA | KI | KU | KE | KO | < | | |
| ° | SA | SI | SU | SE | SO | > | | |
| BLANK | TA | CHI | TSU | TE | TO | ▷ | | |
| ▽ | CLEAR | PRECEDING CHARACTER DELETION | DELETION | YES | NO | △ | | |
| IT IS A FINE DAY TODAY, ISN'T IT ■ | | | | | | 1997/2/25 19:33 | | |

FIG.23

| COMMUNICATOR EYE CONTROL | | | | | | | — | ☐ | × |
|---|---|---|---|---|---|---|---|---|---|
| FILE(F) EDITING(E) WINDOW(W) HELP(H) | | | | | | | — | ☐ | × |
| CANCELLATION | FUNCTION | REGISTRATION | CALL | KATAKANA | ENGLISH CAPITAL LETTER | UTTERANCE | | | |
| I | NA | NI | NU | NE | NO | △ | | | |
| 、 | HA | HI | HU | HE | HO | < | | | |
| 。 | MA | MI | MU | ME | MO | > | | | |
| BLANK | YA | YU | YO | 、 | 。 | ▷ | | | |
| ▽ | CLEAR | PRECEDING CHARACTER DELETION | DELETION | YES | NO | △ | | | |
| IT IS A FINE DAY TODAY,ISN'T IT ■ | | | | | | 1997/2/25 19:44 | | | |

FIG.24

| COMMUNICATOR EYE CONTROL | | | | | | — | □ | × |
|---|---|---|---|---|---|---|---|---|
| FILE(F) EDITING(E) WINDOW(W) HELP(H) | | | | | | | — | × |
| CANCELLATION | FUNCTION | REGISTRATION | CALL | KATAKANA | ENGLISH CAPITAL LETTER | UTTERANCE | | |
| — | RA | RI | RU | RE | RO | ◁ | | |
| ' | WA | | | WO | N | < | | |
| ° | A | — | U | E | O | > | | |
| BLANK | YA | YU | YO | TSU | · | ▷ | | |
| ▽ | CLEAR | PRECEDING CHARACTER DELETION | DELETION | YES | NO | △ | | |
| IT IS A FINE DAY TODAY, ISN'T IT ■ | | | | | | 1997/2/25 19:43 | | |

FIG.25

| COMMUNICATOR EYE CONTROL | | | | | □ ▢ × |
|---|---|---|---|---|---|
| FILE(F) EDITING(E) WINDOW(W) HELP(H) | | | | | □ ▢ × |

| CANCEL | | | | | ▽ |
|---|---|---|---|---|---|
| CALIBRATION | | | CHANGE PRONOUNCING SPEED | | |
| MEMO PAGE PRINTING | | | SET KEY VOLUME | | |
| RECESS | | | CHANGE MAINTENANCE TIME | | |
| CHANGE VOLUME | | | CHANGE INVALID TIME | | |
| CHANGE VOICE SEX DISTINCTION | | | CHANGE BLINKING TIME | | |

FUNCTION  1997/2/24 17:39

FIG.36

| COMMUNICATOR EYE CONTROL | | | | | − ⬜ × |
|---|---|---|---|---|---|
| FILE(F) EDITING(E) WINDOW(W) HELP(H) | | | | | − ⬜ × |

CHANGE OF KEYBOARD SIZE(VERTICAL DIRECTION)

| OK | CANCEL | | | |
|---|---|---|---|---|
|  | △ |  |  | △ |
| UP (0-10) | 5 |  | DOWN (20-37) | 32 |
|  | ▽ |  |  | ▽ |
| 0 | 1 | 2 | 3 | 4 |
| 5 | 6 | 7 | 8 | 9 |

(32 box marked ~20R)

FUNCTION:KEYBOARD SIZE CHANGE UP DOWN     1997/2/24 18:48

FIG.37

COMMUNICATOR EYE CONTROL

FILE(F) EDITING(E) WINDOW(W) HELP(H)

| CANCELLATION | FUNCTION | REGISTRATION | CALL | KATAKANA | ENGLISH CAPITAL LETTER | UTTERANCE |
|---|---|---|---|---|---|---|
| | A | — | U | E | O | ◁ |
| | KA | KI | KU | KE | KO | < |
| | SA | SI | SU | SE | SO | > |
| | TA | CHI | TSU | TE | TO | ▷ |
| | CLEAR | PRECEDING CHARACTER DELETION | DELETION | YES | NO | △ |
| BLANK | , | ∘ | | | | |
| ▽ | | | | | | |

REGISTERED SENTENCE1¥nREGISTERED SENTENCE2¥n···REGISTERED SENTENCE10¥nREGISTERED SENTENCE1¥nREGISTERED SENTENCE2¥n···REGISTERED SENTENCE2¥n···
|·············································PAGE1·······································|·············································PAGE2·······
¥nREGISTERED SENTENCE10¥n········¥nREGISTERED SENTENCE10¥n
|·············································PAGE10······|

FIG.51

| CANCELLATION | FUNCTION | REGISTRATION | CALL | KATAKANA | ENGLISH CAPITAL LETTER | UTTERANCE |
|---|---|---|---|---|---|---|
| — | A | I | U | E | O | ◁ |
| ` | KA | KI | KU | KE | KO | < |
| ° | SA | SI | SU | SE | SO | > |
| BLANK | TA | CHI | TSU | TE | TO | ▷ |
| ▽ | CLEAR | PRECEDING CHARACTER DELETION | DELETION | YES | NO | △ |

COMMUNICATOR EYE CONTROL

FILE(F) EDITING(E) WINDOW(W) HELP(H)

GOOD AFTERNOON ■

| FIXED SENTENCE PAGE | GREETING | WEATHER | FEELING | ELECTRICITY | ENVIRONMENT |
|---|---|---|---|---|---|
| FIXED SENTENCE 1 | GOOD MORING | IT IS A FINE DAY, ISN'T IT | FEEL WELL | TURN ON TV | OPEN WINDOW |
| FIXED SENTENCE 2 | GOOD AFTERNOON | IT IS A BAD DAY, ISN'T IT | FEEL SICK | TURN OFF TV | CLOSE OPEN WINDOW |
| FIXED SENTENCE 3 | GOOD EVENING | IT IS COLD, ISN'T IT | PLEASANT | TURN ON RADIO | DRAW CURTAIN BACK |
| FIXED SENTENCE 4 | GOOD-BY | IT IS HOT, ISN'T IT | INTERESTING | TURN OFF RADIO | DRAW CURTAIN |
| FIXED SENTENCE 5 | COME AGAIN | IT IS FINE, ISN'T IT | DEAR | TURN VOLUME UP | TURN OF AIR-CONDITIONER |
| FIXED SENTENCE 6 | THANK YOU | IT IS CLOUDY, ISN'T IT | SAD | TURN VOLUME DOWN | TURN OFF AIR-CONDITIONER |
| FIXED SENTENCE 7 | HOW ARE YOU | IT RAINS | LONELY | TURN ON LIGHT | CLOSE DOOR |
| FIXED SENTENCE 8 | I AM FINE | IT SNOWS | FEARFUL | TURN OFF LIGHT | OPEN DOOR |

| FIXED SENTENCE PAGE | FAMILY | PHYSICAL CONDITION | NURSING 1 | NURSING 2 | TIME |
|---|---|---|---|---|---|
| FIXED SENTENCE 1 | CALL GRANDFATHER TO ME | FEEL WELL | SEND FOR A DOCTOR | SPREAD BLANKET | WHAT TIME IS IT NOW |
| FIXED SENTENCE 2 | CALL GRANDMOTHER TO ME | FEEL ILL | CALL A NURSE TO ME | TAKE OFF BLANKET | WHAT IS THE DATE TODAY, AND WHAT DAY IS IT TODAY |
| FIXED SENTENCE 3 | CALL FATHER TO ME | I AM TIRED | PUT AWAY A BED | HUNGRY | ... |
| FIXED SENTENCE 4 | CALL MOTHER TO ME | I AM SLEEPY | MAKE A BED | HELP ME DRINK WATER | ... |
| FIXED SENTENCE 5 | CALL ELDER BROTHER TO ME | I HAVE A HEADACHE | TAKE CARE OF THE PERSONAL NEEDS OF A SICK PERSON | DETACH CONVERSATION AID APPARATUS | ... |
| FIXED SENTENCE 6 | CALL ELDER SISTER TO ME | I HAVE A STOMACHACHE | I WOULD LIKE TO TURN TO THE RIGHT | TURN OFF CONVERSATION AID APPARATUS | ... |
| FIXED SENTENCE 7 | CALL YOUNGER BROTHER TO ME | I HAVE A SORE THROAT | I WOULD LIKE TO TURN TO THE REFT | ... | ... |
| FIXED SENTENCE 8 | CALL YOUNGER SISTER TO ME | I HAVE A SUFFER FROM LUMBAGO | I WOULD LIKE TO TURN UPWARD | ... | ... |

FIG.69

COMMUNICATOR EYE CONTROL-[CCHMD11]

FILE(F) SET(S) HELP(H)

| CANCELLATION | SET | REGISTRATION | CALL | KATAKANA | ENGLISH CAPITAL LETTER | UTTERANCE |
|---|---|---|---|---|---|---|
| I | A | I | U | E | O | ◁ |
| , | KA | KI | KU | KE | KO | < |
| ° | SA | SI | SU | SE | SO | > |
| BLANK | TA | CHI | TSU | TE | TO | ▷ |
| ▽ | CLEAR | ⇩ | DELETION | YES | NO | △ |

IT IS A FINE DAY, ISN'T IT ?

FIG. 70

| NEW CALIBRATION(N) |   |
|---|---|
| LEARNING CALIBRATION(C) |   |
| REST |   |
| VOLUME | ▶ |
| VOICE SEX DISTINCTION |   |
| PRONOUNCING SPEED | ▶ |
| KEY NOTE |   |
| MAINTENANCE TIME | ▶ |
| INVALID TIME | ▶ |
| BLINKING TIME | ▶ |
| SET NUMBER OF KEYBOARD CHARACTERS | ▶ |
| INPUT CONFIRMATION METHOD | ▶ |
| CURSOR MOVEMENT BY VISUAL AXIS |   |
| KEYBOARD SIZE··· |   |
| SET SCENE COLOR(X) |   |
| MOUSE INPUT(M) |   |
| INPUT INITIAL SET DISPLAY |   |
| SET REMOTE CONTROL |   |
| LEARNING REMOTE |   |
| CONTROL REGISTRATION |   |
| SET VIDEO | ▶ |

FIG.72

COMMUNICATOR EYE CONTROL-[CCHMD11]

FILE(F) SET(S) HELP(H)

| CANCELLATION | SET | REGISTRATION | CALL | KATAKANA | ENGLISH CAPITAL LETTER | UTTERANCE |
|---|---|---|---|---|---|---|
| — | //A// | — | U | E | O | ◁ |
| ' | KA | KI | KU | KE | KO | < |
| ° | SA | SI | SU | SE | SO | > |
| BLANK | TA | CHI | TSU | TE | TO | ▷ |
| ▽ | CLEAR | ⇨ | DELETION | YES | NO | △ |

IT IS A FINE DAY, ISN'T IT ?

VISUAL-AXIS ENTRY TRANSMISSION APPARATUS AND METHOD THEREFOR

BACKGROUND OF THE INVENTION

1. Field of the Invention

The present invention relates to a visual axis entry transmission apparatus, and to a method for detecting the line of sight (visual axis) from a user to a display panel and for inputting the result of the detection of the line of sight as information to be shown on a display panel in order to communicate the intent of the user.

2. Related Background Art

A visual axis entry transmission apparatus has been proposed, and is in practical use, that detects the line of sight from a user to a display panel, and inputs the result of the detection of the line of sight as information to be shown on the display panel so as to communicate the intent of the user.

For example, a well known visual axis entry transmission apparatus displays 50 kana characters, alphabetical characters, etc., on a monitor, analyzes a user's visual axis location by obtaining images of the eyeballs of the user with a camera, and then, to perform character input, identifies the character in a character table at the terminus of the visual axis.

However, with the conventional visual axis entry transmission apparatus a user must depress a foot button when he or she decides on a character to be input. The use of this apparatus, however, is difficult for a seriously physically handicapped person who can not depress a foot button.

SUMMARY OF THE INVENTION

It is, therefore, one objective of the present invention to provide a visual axis entry transmission apparatus and method that enables a seriously physically handicapped person who can not depress a foot button to easily transmit the determination of a character to be input.

It is another objective of the present invention to provide a visual axis entry transmission apparatus and method with which a user can confirm the results of a detection of the line of sight and can thus avoid having to unnecessarily repeat an operation.

It is an additional objective of the present invention to provide a visual axis entry transmission apparatus and method with which a user can see an externally input video image, while watching a display panel.

It is a further objective of the present invention to provide a visual axis entry transmission apparatus and method with which a user can select one of a number of options by entering the line of sight, while viewing an externally input image.

It is still another objective of the present invention to provide a visual axis entry transmission apparatus and method for displaying options on a display panel in such a manner that a user can easily identify them.

It is a still additional objective of the present invention to provide a visual axis entry transmission apparatus and method for sequentially varying a control for an external device.

It is a still further objective of the present invention to provide a visual axis transmission apparatus and method for easily and certainly performing a predetermined entry, and for obtaining an operating environment that facilitates an operation involving an entry by a user.

To achieve the above objectives, according to a first aspect of the present invention, a visual axis transmission apparatus comprises:

video display means for displaying a video image on a display panel;

visual axis detection means for detecting the line of sight of a user who faces the video image on the display panel, and for transmitting the intent of the user in accordance with the line of sight that is detected; and selection determination means for employing a visual axis position detected by the visual axis detection means to make a selection from the display panel that the user is viewing.

In addition, according to a second aspect of the present invention, a visual axis transmission method comprises the steps of:

displaying a video image on a display panel;

detecting the line of sight of a user who is facing the video on the display panel, and transmitting the intent of the user in accordance with the line of sight that is detected; and employing a detected visual axis position to determine an option made on the display panel that the user is viewing.

Furthermore, according to a third aspect of the present invention, provided is a memory medium on which is stored a program to be executed by a computer in a visual axis transmission apparatus for transmitting the intent of a user in accordance with the line of sight, the program comprising the procedures of:

displaying a video image on a display panel;

detecting the line of sight of the user who is facing video image on the display panel; and employing a detected visual axis position to determine an option made on the display panel that the user is viewing.

Further, according to a fourth aspect of the present invention, a visual axis entry transmission apparatus comprises:

visual axis entry means for detecting the line of sight of a user who is viewing a display panel, and for entering the result of the detection of the line of sight of the user as information input to the display panel to transmit the intent of the user in accordance with the input information; and visual axis detection result notification means for, upon receiving the result of detection, notifying the user of detection result information indicating that the detection of the line of sight was successful, that the detection of the line of sight failed, that the eyes of the user were blinking, or that the same option was selected.

Moreover, according to a fifth aspect of the present invention, a visual axis entry transmission method comprises the steps of:

detecting the line of sight of a user who is viewing a display panel;

entering the result of the detection of the line of sight of the user as information input to the display panel to transmit the intent of the user in accordance with the input information; and notifying, upon receipt of the result of detection, the user of detection result information indicating that the detection of the line of sight was successful, that the detection of the line of sight failed, that the eyes of the user were blinking, or that the same option was selected.

Also, according to a sixth aspect of the present invention, provided is a memory medium on which is stored a program for building a visual axis entry transmission apparatus system, which includes a visual axis entry device that detects the line of sight of a user who is viewing a display panel and enters the result of the detection of the line of sight as input information for a display panel, and which transmits the intent, obtained by the visual axis entry device, of the user using the input information, the program comprising:

a visual detection result notification module for, upon receiving the result of detection, notifying the user of detection result information indicating that the detection of the line of sight was successful, that the detection of the line of sight failed, that the eyes of the user were blinking, or that the same option was selected.

BRIEF DESCRIPTION OF THE DRAWINGS

FIGS. 1A and 1B are diagrams showing the principle of a visual axis detection method;

FIG. 7 is a diagram showing a video image projected onto a display panel provided by a liquid crystal display device and an external monitor;

FIG. 22 is a diagram showing the first page of a hiragana character selection screen;

FIG. 23 is a diagram showing the second page of the hiragana character selection screen;

FIG. 24 is a diagram showing the third page of the hiragana character selection screen;

FIG. 25 is a diagram showing function selection screen 1 that is displayed when a user selects a "function" option on the character selection screen;

FIG. 36 is a diagram showing a screen for changing the vertical size of a keyboard;

FIG. 37 is a diagram showing a character selection screen when the size of the keyboard has been changed;

FIG. 48 is a diagram showing a train of files to which a registered sentence is written;

FIG. 51 is a diagram showing a screen for displaying the result of the retrieval;

FIG. 52 is a diagram showing a table of fixed sentences and the names of fixed sentence pages;

FIG. 69 is a diagram showing an example screen on the head-mounted display that is obtained through external video display processing performed by the visual axis entry transmission apparatus according to a seventeenth embodiment of the present invention;

FIG. 70 is a diagram showing another example screen on the head-mounted display that is obtained through the external video display processing performed by the visual axis entry transmission apparatus according to the seventeenth embodiment of the present invention;

FIG. 72 is a diagram showing a further example screen on the head-mounted display that is obtained through the external video display processing performed by the visual axis entry transmission apparatus according to the seventeenth embodiment of the present invention;

DETAILED DESCRIPTION OF THE PREFERRED EMBODIMENTS

The preferred embodiments of a visual axis entry transmission apparatus and a method according to the present invention will now be described while referring to the accompanying drawings.

(a) First Embodiment

First, the principle of a visual axis detection method will be explained. FIGS. 1A and 1B are a top view and a side view for explaining the principle of a visual axis detection method.

Figure 2A:
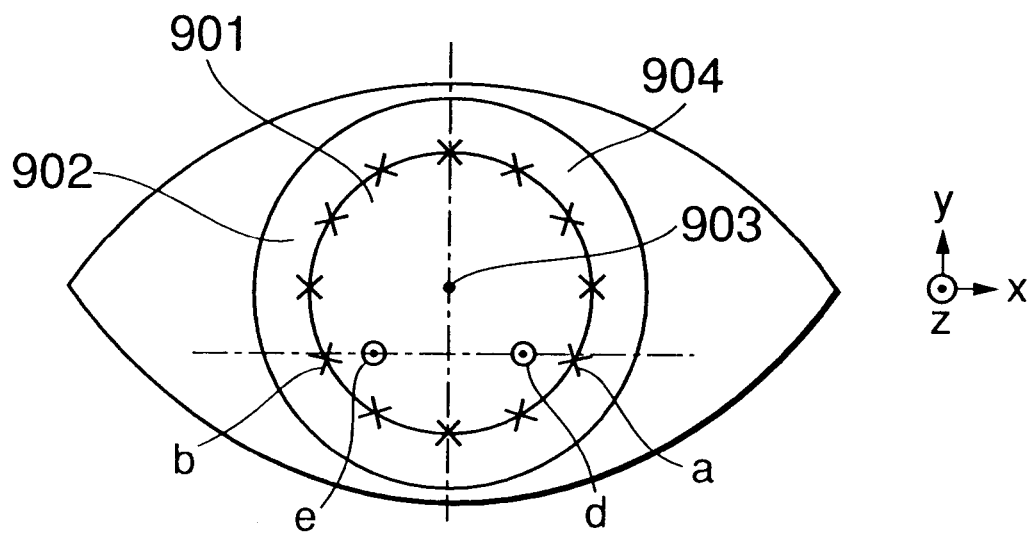
FIGS. 2A and 2B are diagrams showing the image of an eyeball projected onto an image sensor and the intensity of a corresponding signal.
Figure 2B:
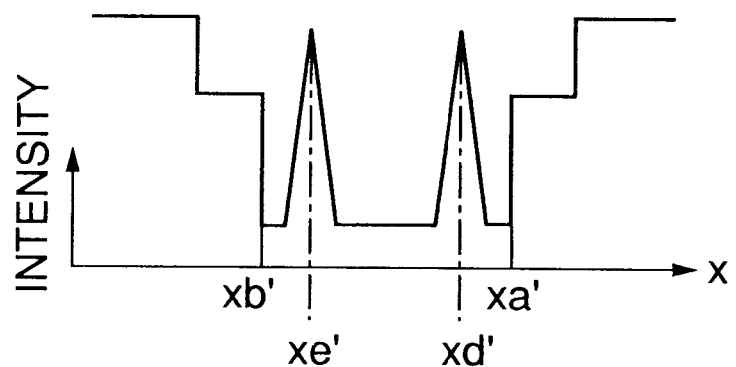

Light-emitting diodes (IRED) 906a and 906b emit infrared light that is not sensed by a user. These light sources are located substantially symmetrically in direction x (the horizontal direction) relative to the light axis of a focusing lens 911, and sightly downward in direction Y (the vertical direction). One part of the emitted light reflected by an eyeball 908 of the user is passed through the focusing lens 911 and forms an image on an image sensor 912. FIGS. 2A and 2B are diagrams showing the image of the eyeball 908 that is projected onto the image sensor 912, and the intensity of the signal.

On the horizontal plane (see FIG. 1A), the infrared light emitted by the light source 906a illuminates a cornea 910 of an eyeball 908 of a user A reflected corneal image d (virtual image) is formed by the infrared light reflected on the surface of the cornea 910 and is concentrated by the focusing lens 911 to form an image at position d' on the image sensor 912. Similarly, the infrared light emitted by the light source 906a illuminates the cornea 910 of the eyeball 908. A reflected corneal image e (a virtual image) is formed by the infrared light reflected onto the surface of the cornea 910, and is concentrated by the focusing lens 911 to form an image at position e' on the image sensor 912.

Light fluxes reflected from edges a and b of an iris 904 are passed through the focusing lens 911 and form images at positions a' and b' on the image sensor 912.

When the rotation angle θ of the light axis of the eyeball 908 at the light axis of the focusing lens 911 is small, multiple points with coordinates xa and xb, which are x coordinates for the edges a and b of the iris 904, can be obtained on the image sensor 912 (see the x marks in FIG. 2A). Thus, the center of the pupil, xc, is calculated by using the least square method for a circle. When the x coordinate of the curvature center o of the cornea 910 is defined as xo, rotation angle θx at the light axis of the eyeball 908 is represented by equation (1):

$$oc \cdot \sin \theta x = xc - xo \quad (1).$$

While taking into account a predetermined compensation value δx at a point k midway between the reflected corneal images d and e, the curvature center xo is calculated using equation (2):

$$xk = (xd + xe)/2$$

$$xo = (xd + xe)/2 + \delta x \quad (2).$$

δx is a value geometrically obtained in accordance with the location of the apparatus and the distance from the eyeball 908. Therefore, from equations (1) and (2) θx is obtained using equation (3):

$$\theta x = \arcsin[[xc - \{(xd + xe)/2 + \delta x\}]/oc] \quad (3).$$

Furthermore, when the coordinates of the individual characteristic points projected onto the image sensor 912 are rewritten as "'" (prime), they are represented by equation (4):

$$\theta x = \arcsin[[xc' - \{(xd' + xe')/2 + \delta x'\}]/oc/\beta] \quad (4).$$

β is a magnification rate determined by the distance "sze" from the focusing lens 911 to the eyeball 908, and is actually obtained as a function for a distance between the reflected corneal images, |xd'−xe'|.

On the perpendicular plane (see FIG. 1B), the corneal images reflected by the two IREDs 906a and 906b are formed at the same position, which is defined as i. The method used for calculating rotation angle θy of the eyeball 908 is substantially the same as that used for the horizontal plane, except that equation (2) differs. When y coordinate of the corneal curvature center o is defined as yo, yo is obtained using equation (5):

$$yo = yi + \delta y \quad (5).$$

δy is a value geometrically obtained in accordance with the location of the apparatus and the distance from the eyeball 908. Therefore, the rotation angle θy in the perpendicular direction is represented by equation (6):

$$\theta y = \arcsin[[yc' - (yi' + \delta y')]/oc/\beta] \quad (6).$$

When a constant m that is determined by a viewfinder optical system is employed, the positional coordinates (xn, yn) on the screen of a viewfinder are respectively represented for the horizontal plane and for the perpendicular plane by equations (7) and (8):

$$xn = m \cdot \arcsin[[xc' - \{(xd' + xe')/2 + \delta x'\}]/oc/\beta] \quad (7)$$

$$yn = m \cdot \arcsin[[yc' - \{(yi' + \delta y')\}]/oc/\beta] \quad (8).$$

As is apparent from FIG. 2B, the trailing edge (xb') and the leading edge (xa') of a waveform output by the image sensor 912 are employed to detect the edges of the pupil. Furthermore, the peaks of the sharp leading edges (xe') and (xd') are employed to obtain the coordinates of the reflected corneal image.

A personal computer system having a visual axis detection function will now be described as an example visual axis entry transmission apparatus.

Figure 3:
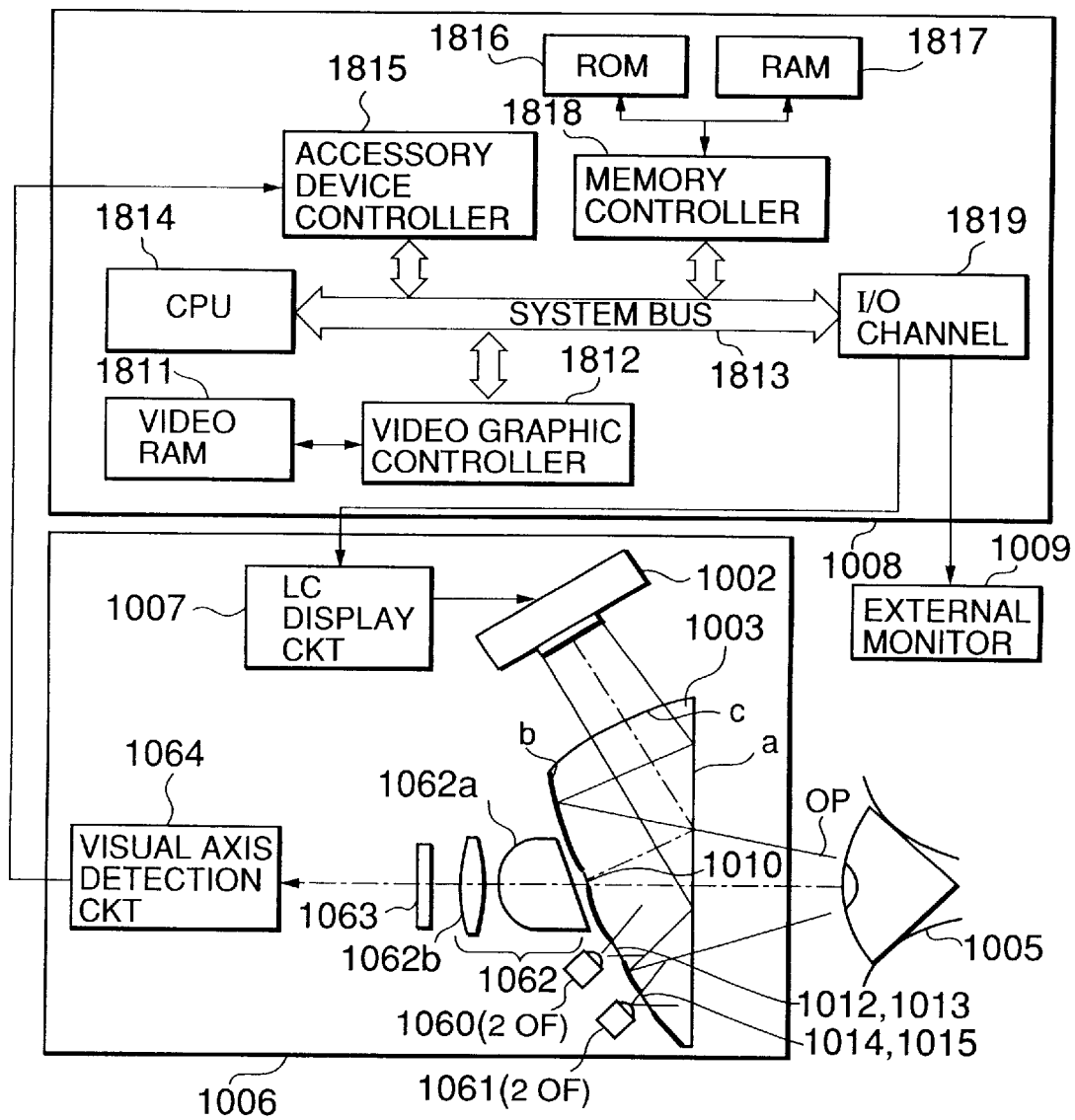
FIG. 3 is a schematic diagram illustrating the arrangement of a personal computer system having a visual axis detection function.

FIG. 3 is a schematic diagram illustrating the arrangement of a personal computer system having a visual axis detection function. The personal computer system comprises a computer unit 1008, which is the main body of a personal computer; a head-mounted display unit 1006, with which an operator can view the screen of the personal computer; and an external monitor 1009, with which an operator or another user can view the screen of the computer.

The head-mounted display unit 1006 is, for example, a pair of goggles or a glass frame that is supported near the eyes of the operator.

The head-mounted display unit 1006 comprises a liquid crystal display device 1002; a special prism 1003, which serves as an enlarging observation system; a visual axis detection circuit 1064 for detecting the line of sight of the eyes 1005 of the operator; a liquid crystal display circuit 1007, for displaying a computer screen on the liquid crystal display device 1002; infrared light emitting diodes 1060 and 1061, for irradiating with infrared light both of the eyes 1005 of the operator; focusing lens 1062a and 1062b for collecting the infrared light reflected by the eyeballs; and a photoelectric converter 1063 for converting the infrared light transmitted by the focusing lens 1062 into an electric signal.

A focus point detection circuit is provided for the visual axis detection circuit 1064 in order to detect the focus point of the operator on the liquid crystal display device 1002, in accordance with the images of the eyeballs of the operator that are displayed on the photoelectric converter 1063.

An explanation will now be given for the optical operation of the observation system in the thus arranged head-mounted display unit 1006. Light from the liquid crystal display device 1002 is refracted by and passed through a third optical face c, is fully reflected by a first optical face a and onto a reflective layer of a second optical face b, is again refracted by and passed through the first optical face a, and is emitted and carried to the eye as a light flux having a spread angle (convergence angle; parallel) that matches the vision of the user.

In this example, the line that connects the eye 1005 of the user and the center of the liquid crystal display device 1002 is designated the basic light axis. The liquid crystal display device 1002 is moved in parallel with the light axis of the prism 1003 to enable it to be adjusted to the vision of the user. It is preferable that the faces of the prism 1003 be three-dimensional curved faces that do not have rotation axes so as to provide a telecentric prism system that compensates for the image focusing and image distortion performances. Therefore, the prism 1003 has a curved structure that includes a basic light axis and is symmetric only to a plane that is parallel to the face of a sheet of paper.

The optical operation of the visual axis detection system in the head-mounted display unit 1006 will now be described. Lights are emitted by the infrared light emitting diodes 1060 (two diodes provided to the rear of the face of a sheet of paper) for eyes without corrective lenses and the infrared diodes 1061 (two diodes also provided to the rear of the face of the sheet of paper) for eyes with corrective lenses, are passed through openings 1012, 1013, 1014 and 1015 that are formed in the second optical face b, and illuminate the eyes of the user in a direction that differs from the light axis of the visual axis detection system.

The illuminating lights are reflected by the pupils and scattered. The lights reflected by corneas from reflected corneal images, and the lights scattered at the pupils from pupil images. These lights are passed through an opening 1010 formed in the second optical face b, and are collected on the image sensor 1063 by the focusing lens system 1062.

The eye image obtained by the image sensor 1063 is transmitted to the visual axis detection circuit 1064, which is constituted based on the visual axis detection principle previously mentioned. The visual axis detection circuit 1064 then outputs focusing point data.

The focusing lens system 1062 consists of two lenses 1062a and 1062b. Especially because the lens 1062a is wedge-shaped, only a small number of lenses are required to constitute the focusing lens system, which is appropriate for reducing. When a curvature is provided for the sloping face of the lens, an eccentric aberration that occurs at the second optical face b can effectively be compensated for. Furthermore, when at least one aspheric face is provided for the focusing lens, it can effectively compensate for the image focusing performance in the space surrounding the axis.

When the aperture of the focusing lens system is located closer to the opening 1010 formed in the second optical face b, the size of the opening 1010 can be smaller, and a transfer hollow in the observation system can be prevented. Therefore, it is preferable that the positions of the opening and of the aperture correspond to each other. When the opening 1010 is formed so that it is smaller than 2 mm, it is smaller than the pupil of the eye, and a transfer hollow for the user can be prevented.

Since a low visibility light is adequate as a light for illuminating eyes, the infrared light is employed. At this time, if at least one lens for reducing the visible light is provided for the focusing lens system, the accuracy can be increased for the detection of a visual axis.

Figure 4:
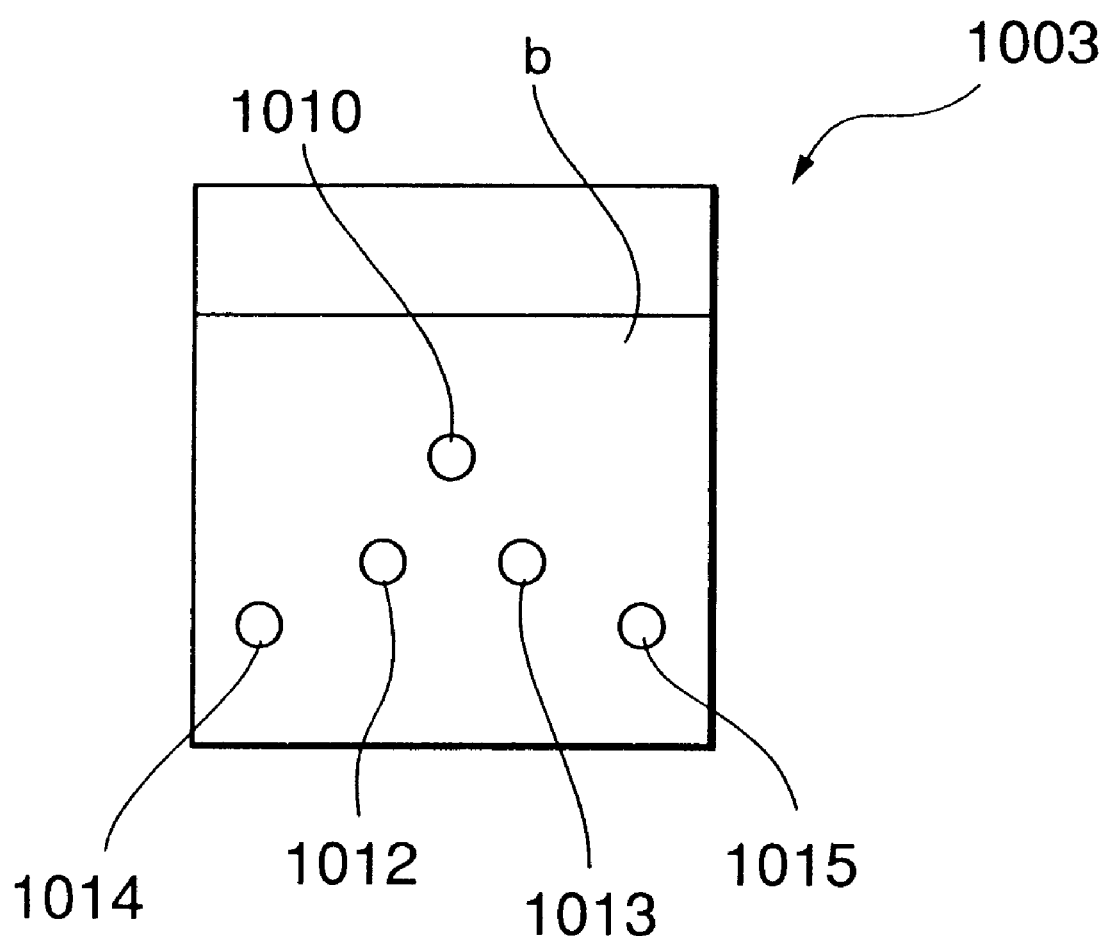
FIG. 4 is a side view of a prism.

FIG. 4 is a side view of the shape of the prism 1003. Reflective mirror coating is applied only to the optical face b and is not applied to the opening 1010 for the focusing lens system 1062 and the openings for the infrared light emitting diodes 1060 and 1061 (the openings 1012 and 1013 for the infrared light emitting diodes for eyes without corrective lenses and the openings 1014 and 1015 for the infrared light emitting diodes for eyes with corrective lenses).

These non-mirror coated sections are too small to affect the viewfinder observation system, and their diameters are preferably equal to or smaller than 2 mm. Since the openings are formed in the mirror coated section, and the prism 1003 is positioned between the eyes and the light sources that are located opposite the eyes, even when the refractivity of the prism 1003 is increased and visibility is enhanced, the light sources can adequately illuminate the eyes when they are located at a position near the height of the eyes.

In this embodiment, the infrared light emitting diodes for eyes without corrective lenses and for eyes with corrective lenses are located at different positions. The two infrared light emitting diodes 1060 for eyes without corrective lenses are located on either side of the optical face b, at the same height, as measured from the lower edge, and slightly separate, by a small interval, from the light axis, and are symmetrically arranged along the light axis. There are three reasons for this. The first reason is that to obtain a better illumination condition in accordance with the distance from the eyeballs, the infrared light emitting diodes are so located that they equally illuminate the eye detection area. The second reason is that the location of the diodes must be higher enough that the reflected corneal images are not obtained at the eyelids, and so that the infrared light emitting diodes for eyes without corrective lenses are positioned higher than the infrared light emitting diodes for eyes with corrective lenses. The third reason is to permit a ghost that is produced when the infrared light is reflected by corrective lenses to appear only at the periphery where its detection will have little effect. The infrared light emitting diodes for eyes with corrective lenses are positioned horizontally and vertically apart from those for eyes without corrective lenses.

The identification of eyes without corrective lenses and eyes with corrective lenses is performed by calculating the distance between the lenses and the prism 1003 using the interval $|0xd'-xe'|$ for the reflected corneal images.

In accordance with the above described principle, which is based on the images of the eyeballs of the operator that are formed on the photoelectric converter 1063, the visual axis detection circuit 1064 ascertains the operator's point of focus on the screen of the liquid crystal display device 1002.

An explanation will now be given for the personal computer unit 1008. The personal computer unit 1008 comprises: a CPU 1814, which performs the program based data computation; a system bus 1813, for connecting the individual devices; a memory controller 1818 for controlling a ROM 1816 and a RAM 1817; a video graphic controller 1812 for displaying data stored in a RAM 1811 on a display screen; an accessory device controller 1815, which controls a pointing device and a keyboard and which is connected to the visual axis detection circuit 1064 of the head-mounted display unit 1006 in this embodiment; and an I/O channel 1819, which controls peripheral devices and which is connected to the liquid crystal display circuit 1007 of the head-mounted display unit 1006 in this embodiment.

As is described above, according to the visual axis entry transmission apparatus in this embodiment, the operator's visual axis location position, which is ascertained by the visual axis detector 1064 of the head-mounted display unit 1006, can be employed as a pointing device by the personal computer unit 1008, and can also be employed to scroll the screen and to make menu selections.

Further, since the computer screen can be displayed on the external monitor 1009, a person other than the operator can view it. A head-mounted display unit for use by a single eye may be employed, and in this case, the operator can also view the external monitor 1009.

Figure 5:
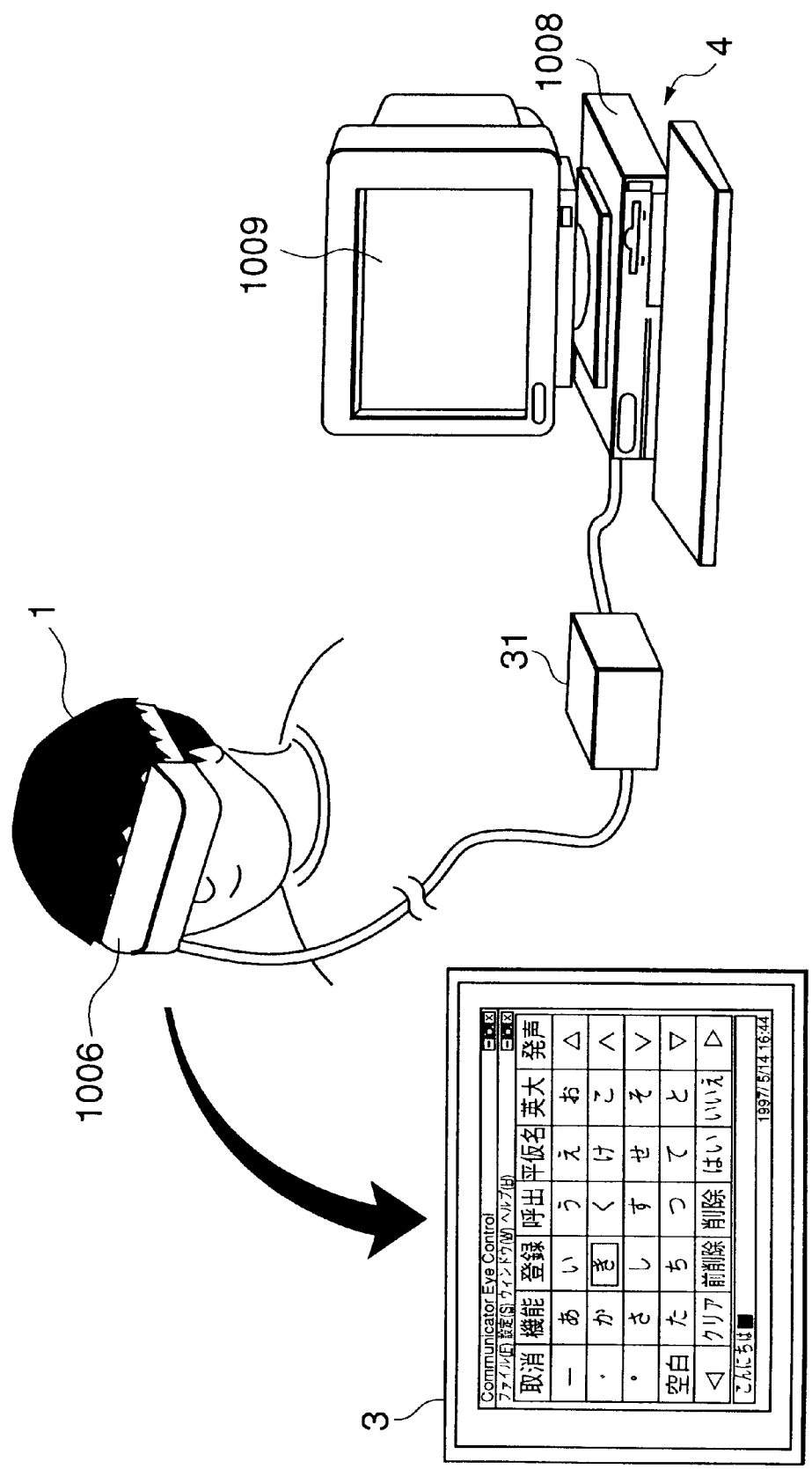
FIG. 5 is a conceptual diagram showing the operation of a visual axis entry transmission apparatus according to a first embodiment of the present invention.

An explanation will be given for the operating state of the thus arranged visual axis entry transmission apparatus. FIG. 5 is a conceptual diagram showing the operating state of the visual axis entry transmission apparatus. In FIG. 5, the head-mounted display unit 1006 incorporates a visual axis detection circuit. As previously described, A computer 4 is constituted by the personal computer unit 1008 and the external monitor 1009. An adaptor 31 is used to connect the head-mounted display unit 1006 and the computer 4, and to supply power to the head-mounted display unit 1006.

A user 1 of the system wears the head-mounted display unit 1006 in the same manner as are glasses, and can view a video image 3 generated by the computer 4.

The visual axis data detected by the visual axis detection circuit in the head-mounted display unit 1006 are transmitted to the computer 4. The user 1 can use the head-mounted display unit 1006 to view the video image 3 generated by the computer 4, and can issue specific instructions using his line of sight (the movement of his eyes). In this embodiment, the video image 3 projected onto the display panel, which comprises hiragana, katakana, alphabetical characters and numerals that are generated by the computer 4, the user 1 can input individual characters by focusing on them, and can create sentences and engage in a conversation.

Figure 6:
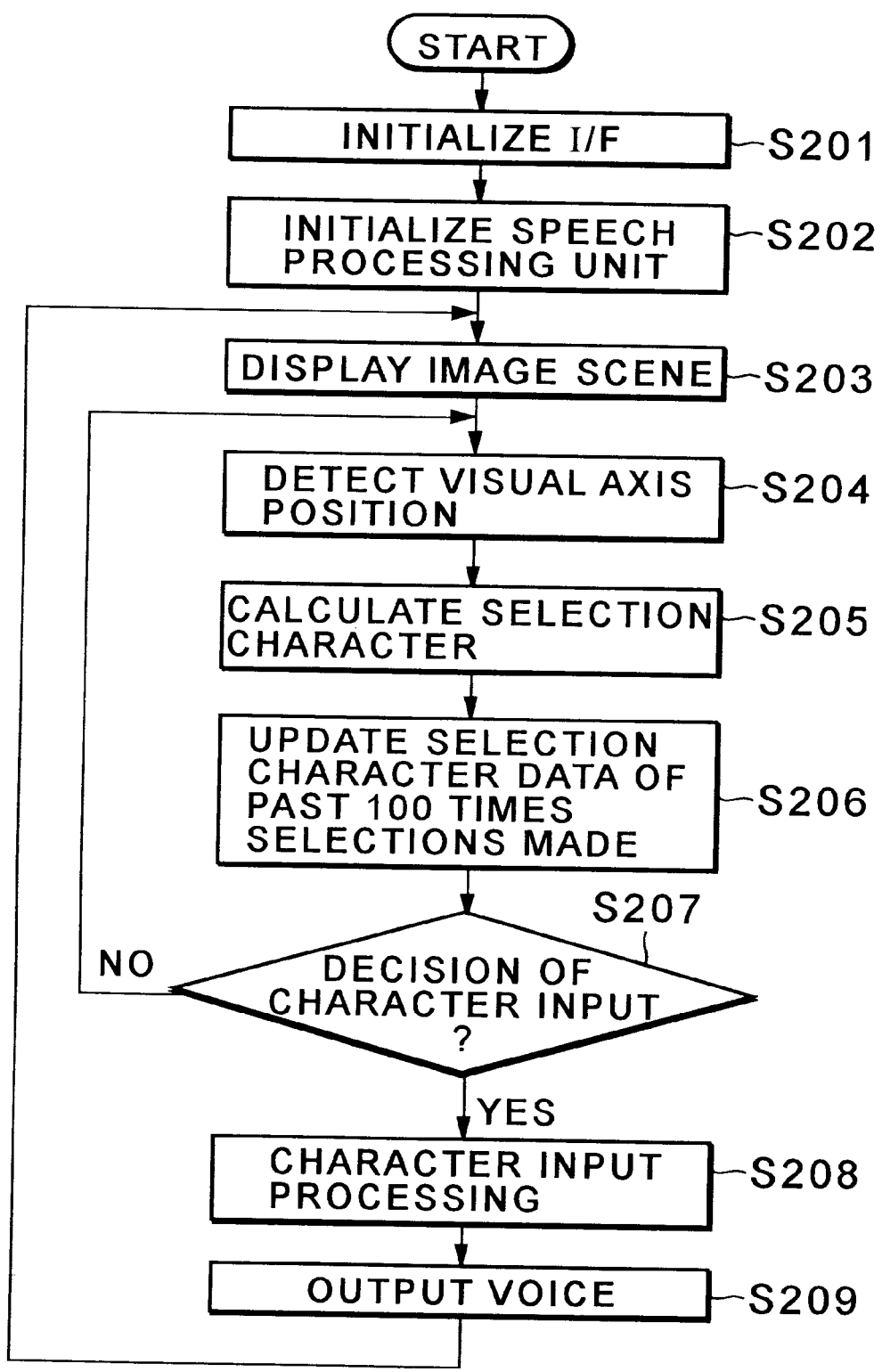
FIG. 6 is a flowchart showing the processing performed by a visual axis entry transmission program.

FIG. 6 is a flowchart showing the processing performed by a visual axis entry transmission program. This program is stored in the ROM 1816 of the personal computer unit 1008, and is executed by the CPU 1814.

When the processing is initiated, first, an I/F for a communication line is initialized (step S201). In this embodiment, a serial port RS232C is opened and is set to the communication enabled state. Then, a speech processing unit is initialized (step S202).

50 hiragana characters (or katakana or alphabetical characters) are displayed, via a display controller 31, on the liquid crystal device 1002 of the head-mounted display unit (visual axis input scouter) 1006 and on the external monitor 1009 (step S203). FIG. 7 is a diagram showing the video image projected onto the display panel provided by the liquid crystal display device 1002 and by the external monitor 1009. The options listed on the display panel will be described later.

Following this, the visual axis position is detected (step S204), and a character at the visual axis position is obtained based on the detected visual axis position data (step S205). Selection character data for the past 100 selections are then updated (step S206).

A check is performed to determine whether the condition for the entry of a character is satisfied by this new character selection (step S207). The character entry condition is that, of the character data in the past 100 selections, the number of selections of pertinent character data equals a number that corresponds to the period of time during which the visual axis must be positioned at the same character in order for it to be entered, or is equal to a number that corresponds to a constant ratio of the length of time during which the visual axis is positioned at the same character to a predetermined period of time.

When, at step S207, the character entry condition is satisfied, a character is added to an input character string (step S208), and the newly input character is pronounced (step S209) to notify the user that the character entry has been completed. Program control thereafter returns to step S203 to display the screen for the selection of a new input character.

When, at step S207, the character entry condition is not satisfied, program control returns to step S204, whereat a new visual axis position is detected to repeat the selection of the character.

As is described above, in the first embodiment, the operator can enter a character regardless of his or her posture, and it is easy for a seriously physically handicapped person to enter a character.

In this embodiment, at step S206, whether or not the character entry condition is satisfied is determined by counting the number of times the visual axis is positioned at the same character. Instead of counting the number of times, however, the timer may be started when the visual axis is positioned at a character and the time length measured. Furthermore, the user may set an arbitrary ratio for the length of time the visual axis remains on a character to a predetermined period of time, so that the useability can be increased.

(b) Second Embodiment

Figure 8:
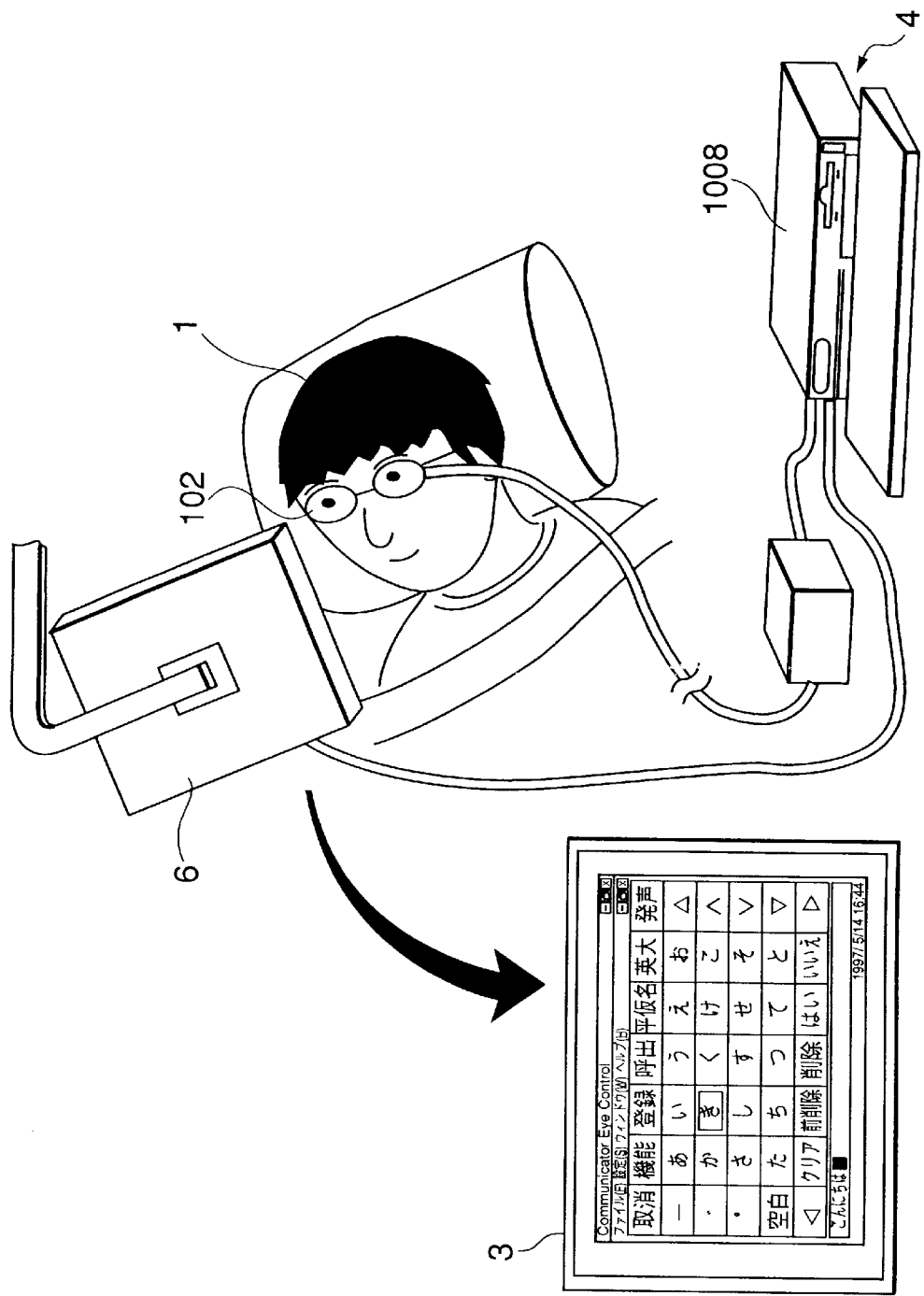
FIG. 8 is a conceptual diagram showing the operation of a visual axis entry transmission apparatus according to a second embodiment of the present invention.

FIG. 8 is a conceptual diagram showing the use of a visual axis entry transmission apparatus according to a second embodiment of the present invention. The same reference numerals as are used for the first embodiment are also used in this embodiment to denote corresponding or identical components.

In FIG. 8, a pair of visual axis entry glasses 102 incorporates a visual axis detection circuit, and has the same internal arrangement as has the previously mentioned head-mounted display unit 1006, with the exception that the portion for displaying a video image 3 is excluded. With this system, a user 1 wears the visual axis entry glasses 102 and views a video image 3 of a display panel using a monitor 6 of a computer 4.

Visual axis position data are detected by the visual axis detection circuit in the visual axis entry glasses 102, and are transmitted to the computer 4. That is, the user 1 can view a video image 3 generated on the monitor 6 by the computer 4, and can instruct a specific operation by moving the visual axis (by moving the eyeballs). In this embodiment, with the display panel video image 3 that is generated by the computer 4 and that consists of hiragana or katakana, alphabetical characters and numerals, the user 1 can input individual characters by focusing on them, and can create sentences and engage in a conversation.

As is described above, in the second embodiment, the user can enter a character, while viewing the video image 3 of the display panel on the monitor 6 with the visual axis entry glasses 102, so that the input operation can be performed in a near to natural manner.

(c) Third Embodiment

Figure 9:
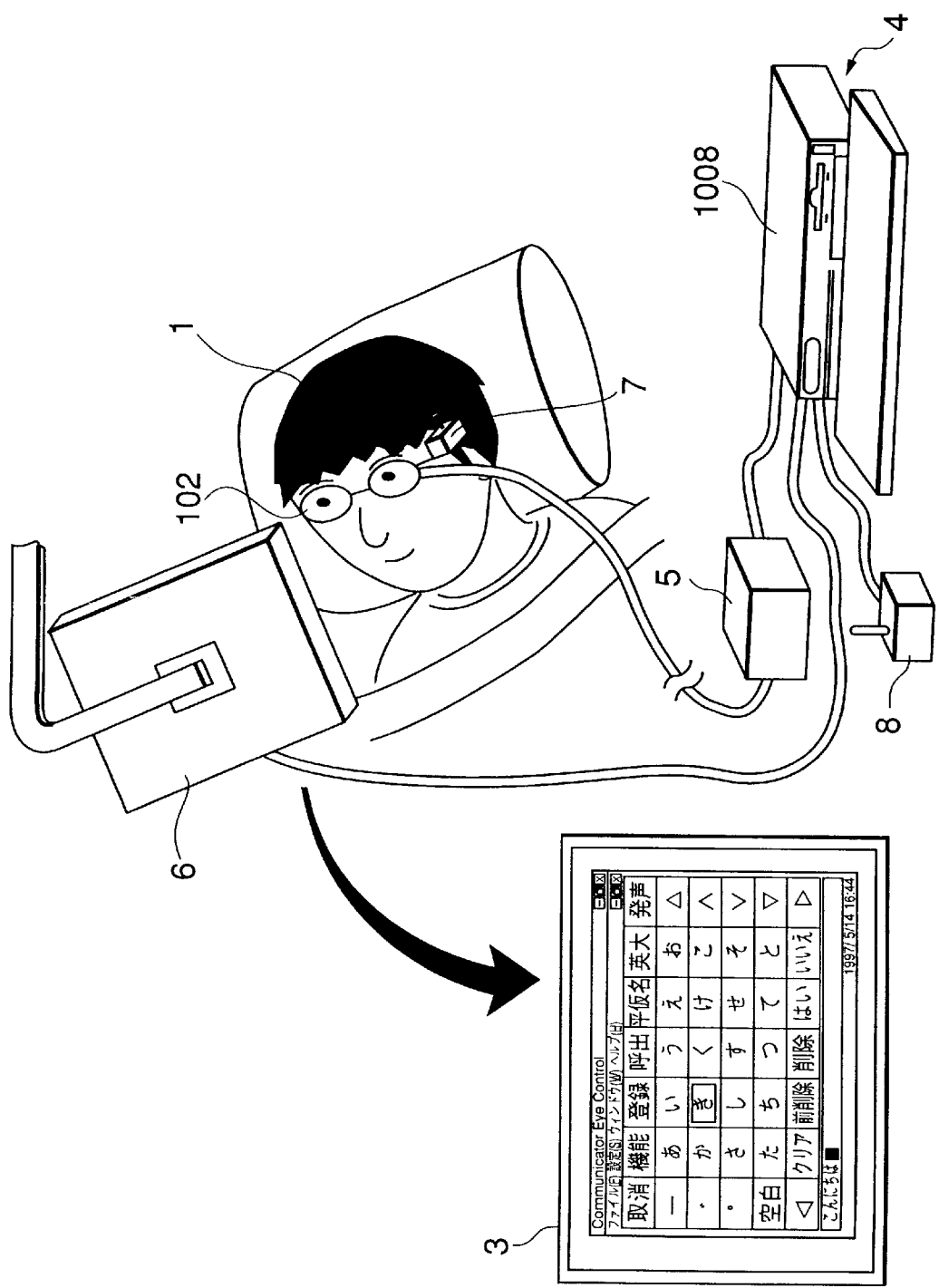
FIG. 9 is a conceptual diagram showing the operation of a visual axis entry transmission apparatus according to a third embodiment of the present invention.

FIG. 9 is a conceptual diagram illustrating the use of a visual axis entry transmission apparatus according to a third embodiment of the present invention. The same reference numerals as are used in the first and the second embodiments are also used in this embodiment to denote corresponding or identical components.

In FIG. 9, a pair of visual axis input glasses 102 incorporates a visual axis detection circuit. Also provided are a magnetic field generator 7, such as a magnet, and a magnetic sensor 8. With this system, a user 1 wears the visual axis entry glasses 102 and the magnetic field generator 7, and views a video image 3 on a monitor 6 of a computer 4.

An induction current is generated at the magnetic sensor 8 by a magnetic field that is produced by the magnetic field generator 7, and as the magnitude of the current is controlled by the computer, data can be obtained for the position and the angle of the head of the user 1.

The visual axis position data, which are detected by the visual axis detection circuit of the visual axis entry glasses 102, and the position and angle data for the head of the user, which are obtained by the magnetic sensor 8, are transmitted to the computer 4. Specifically, the user 1 can view a video image 3 generated on the monitor 6 by the computer 4, and can instruct a specific operation by moving the visual axis (by moving the eyes), while he or she employs the head position and angle data to correct an error in the visual axis position data that is caused by moving the head. In this embodiment, with the display panel video 3 that is generated by the computer 4 and that consists of hiragana or katakana, alphabetical characters and numerals, the user 1 can input individual characters by focusing on them, and can create sentences and engage in a conversation.

In the third embodiment, an error in the visual axis position data that is caused by moving the head can be corrected, and the number of character input errors can be reduced.

(d) Fourth Embodiment

Figure 10:
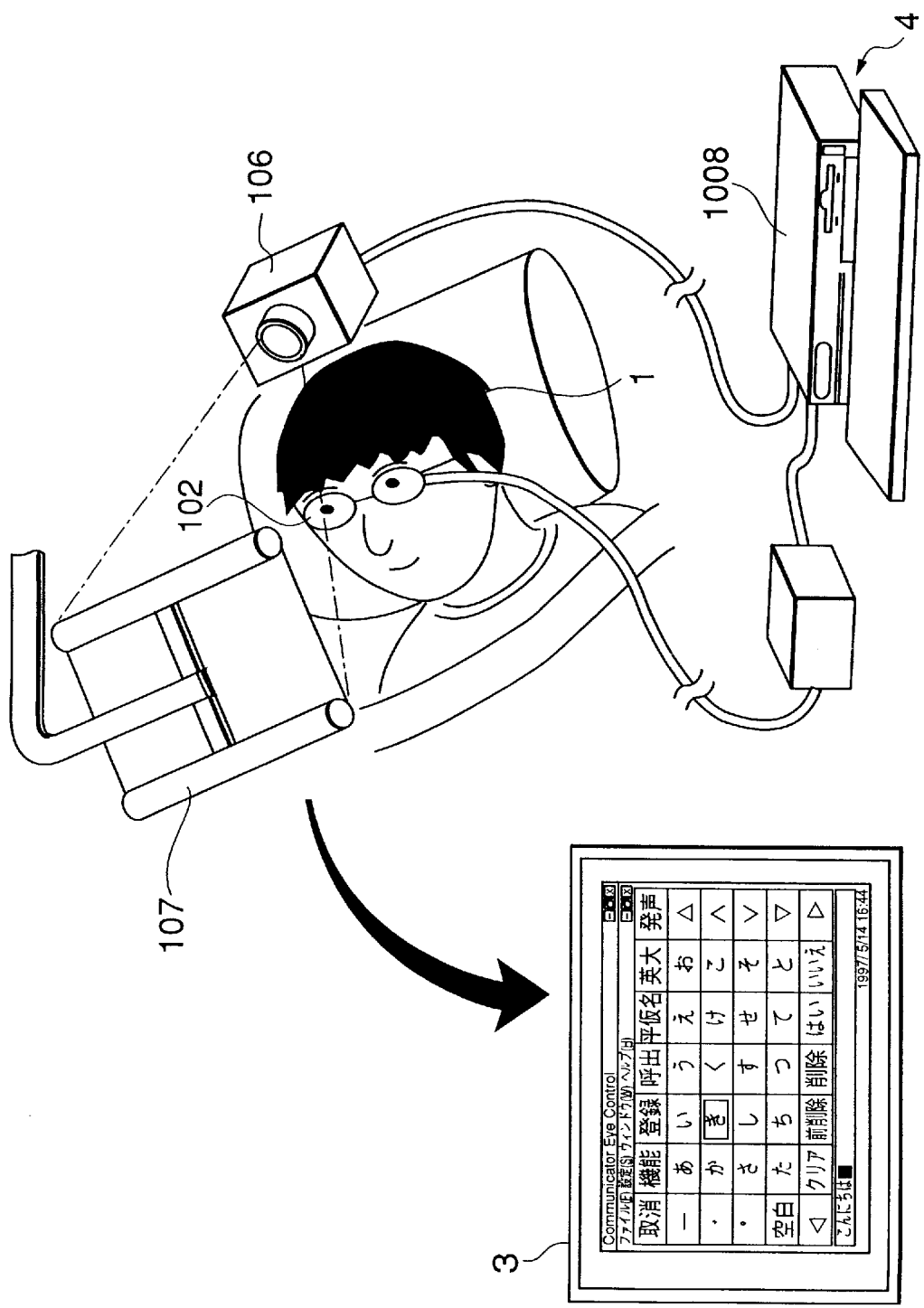
FIG. 10 is a conceptual diagram showing the operation of a visual axis entry transmission apparatus according to a fourth embodiment of the present invention.

FIG. 10 is a conceptual diagram illustrating the use of a visual axis entry transmission apparatus according to a fourth embodiment of the present invention. The same reference numerals as are used for the first and the second embodiments are also used in this embodiment to denote corresponding or identical components.

In FIG. 10, a pair of visual axis entry glasses 102 incorporates a visual axis detection circuit. With the system, a user 1 wears the visual axis entry glasses 102, and views a video image 3 projected onto a screen 107 by a projection device 106.

The visual axis position data are detected by the visual axis detection circuit of the visual axis entry glasses 102 and are transmitted to the computer 4. Specifically, the user 1 can view the video image 3 generated on the screen 107 by the computer 4, and can instruct a specific operation by moving the visual axis (by moving the eyes). In this embodiment, with the display panel video image 3 that is generated by the computer 4 and that consists of hiragana or katakana, alphabetical characters and numerals, the user 1 can input individual characters by focusing on them, and can create sentences and engage in a conversation.

According to the fourth embodiment, since the user 1 views the video image 3 projected onto the screen 107, the eyes of the user 1 do not become very tired, even though the user continues to view the video image 3 for an extended period of time.

(e) Fifth Embodiment

Figure 11:
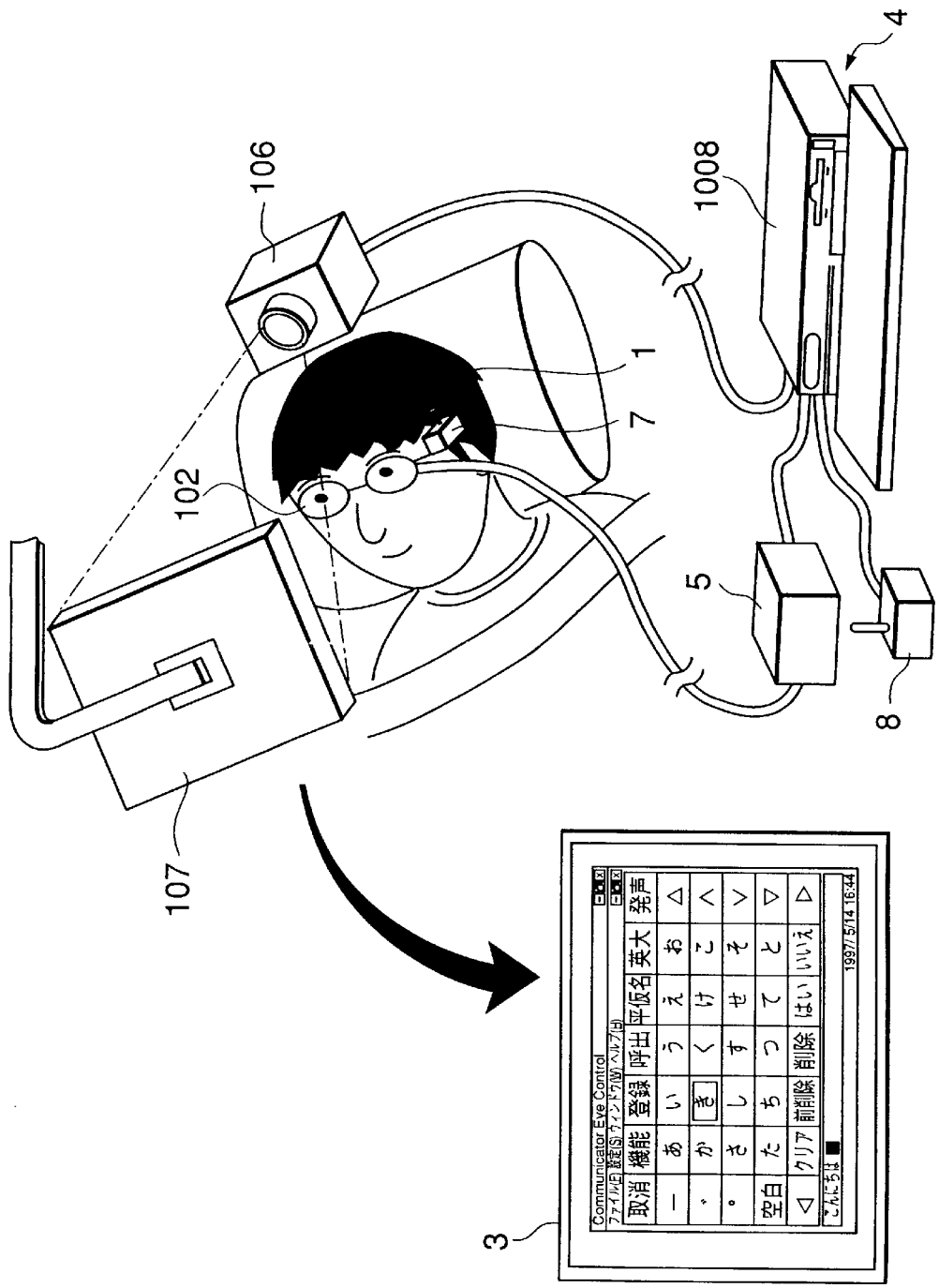
FIG. 11 is a conceptual diagram showing the operation of a visual axis entry transmission apparatus according to a fifth embodiment of the present invention.

FIG. 11 is a conceptual diagram illustrating the use of a visual axis entry transmission apparatus according to a fifth embodiment of the present invention. The same reference numerals as are used in the first, the second and the fourth embodiments are also used in this embodiment to denote corresponding or identical components.

In FIG. 11, a pair of visual axis input glasses 102 incorporates a visual axis detection circuit. Also provided are a magnetic field generator 7, such as a magnet, and a magnetic sensor 8. With this system, a user 1 wears the visual axis entry glasses 102 and the magnetic field generator 7, and views a video image 3 projected onto a screen 107 by a projection device 106.

An induction current is generated at the magnetic sensor 8 by a magnetic field that is produced by the magnetic field generator 7, and as the magnitude of the current is controlled by the computer, data can be obtained for the position and the angle of the head of the user 1.

The visual axis position data, which are detected by the visual axis detection circuit of the visual axis entry glasses 102, and the position and angle data for the head of the user, which are obtained by the magnetic sensor 8, are transmitted to the computer 4. Specifically, the user 1 can view the video image 3 generated on the screen 107 by the computer 4, and can instruct a specific operation by moving the visual axis (by moving the eyes), while he or she employs the head position and angle data to correct an error in the visual axis position data that is caused by moving the head.

In this embodiment, with the display panel video image 3 that is generated by the computer 4 and that consists of hiragana or katakana, alphabetical characters and numerals, the user 1 can input individual characters by focusing on them, and can create sentences and engage in a conversation.

As is described above, in the fifth embodiment, when the user 1 views the video image 3 projected onto the screen 107, an error in the visual axis position data that is caused by moving the head can be corrected, and the number of character input errors can be reduced.

(f) Sixth Embodiment

Figure 12:
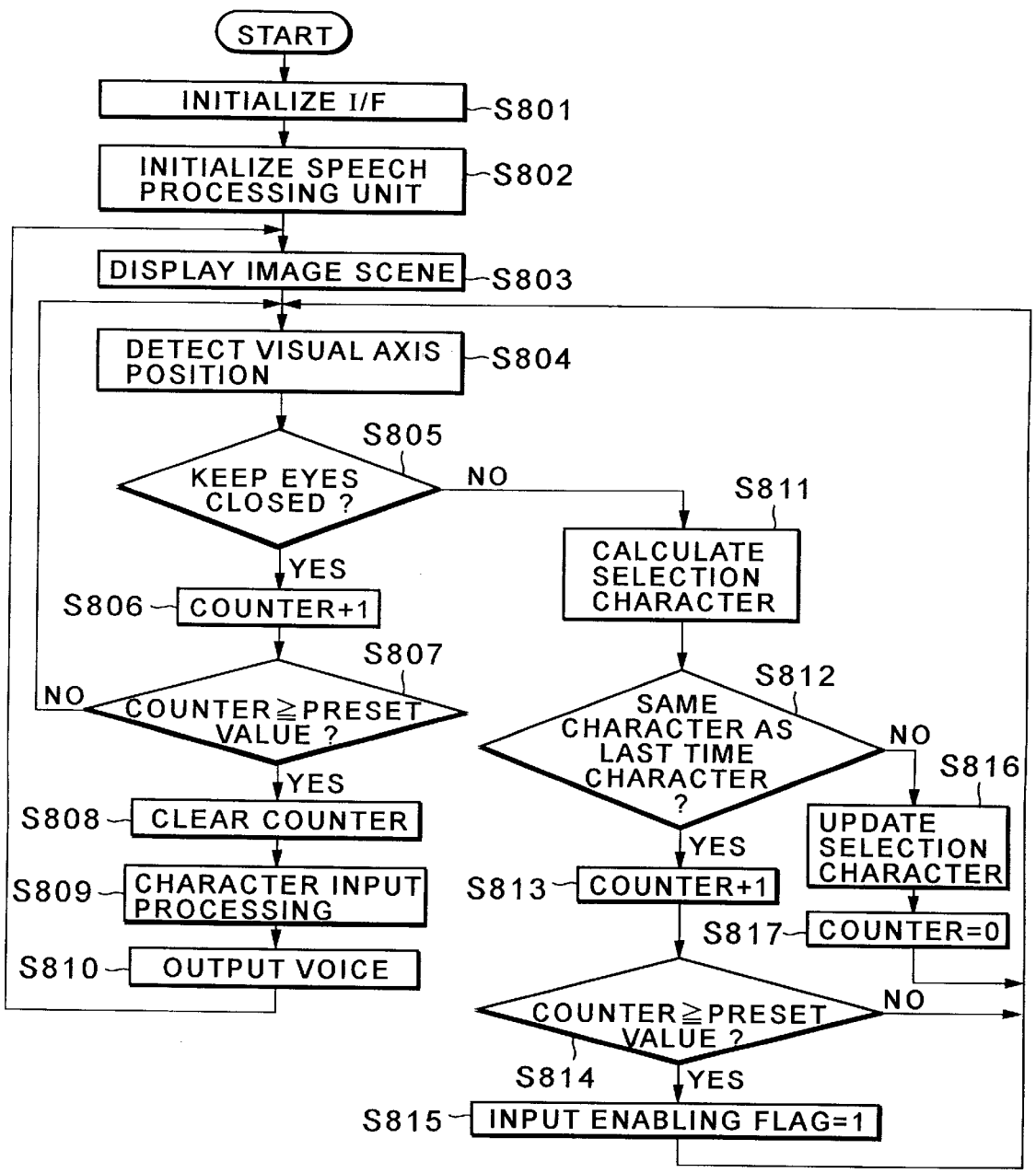
FIG. 12 is a flowchart showing the procedures performed by a visual axis entry transmission program according to a sixth embodiment of the present invention.

The arrangement of an apparatus according to a sixth embodiment is the same as that in the first embodiment. FIG. 12 is a flowchart showing the processing performed by a visual axis entry transmission program according to the sixth embodiment of the present invention. This program is stored in the ROM 1816 of the personal computer unit 1008, and is executed by the CPU 1814.

First, an I/F for a communication line is initialized (step S801). In this embodiment, a serial port RS232C is opened and is set to the communication enabled state.

Then, a speech processing unit is initialized (step S802). Following which 50 hiragana characters (see FIG. 7), or katakana or alphabetical characters, are displayed via a display controller 31 on the liquid crystal device 1002 of the head-mounted display unit (visual axis input scouter) 1006 and on the external monitor 1009 (step S803).

Following this, the visual axis position data are detected (step S804), and are employed to determine whether a user's eyes are closed (step S805). When the visual axis data indicate the user's eyes are not closed, a character at the visual axis position is obtained based on the visual axis position data obtained at step S804 (step S811).

The obtained character is compared with a previously selected character to determine whether the two characters are the same (step S812). When the two characters are the same, a counter value is incremented by one (step S813). Then, a check is performed to determine whether the updated counter value is equal to or greater than a preset value (step S814).

When the counter value is equal to or greater than the preset value, an input enabling flag is set to "1" (step S815). The processes at steps S812, S813, S814 and S815 are performed in order to prevent a visual axis entry at the moment the user closes his or her eyes, and the erroneous input of a character that is not selected by the user. When at step S814 the counter value does not reach the preset value, program control returns to step S804.

When, as a result of the comparison performed at step S812, the recently input character differs from the previously selected character, the selected character is updated (step S816) and the counter is reset (step S817). Program control thereafter returns to step S804.

When at step S805 the visual axis position data indicate the user's eyes are closed, the counter value is incremented by one (step S806).

A check is then performed to determine whether the counter value is equal to or greater than the preset value (step S807). When the counter value is equal to or greater than the preset value, and the input enabling flag is set to "1", the counter is reset (step S808).

A character entry process is performed in the same manner as is the input confirmation method for maintaining the visual axis for a predetermined period of time (step S809), and voice is output (step S810). Program control thereafter returns to step S803.

In the sixth embodiment, since the input data are confirmed by closing the eyes, eye fatigue can be reduced compared with when the input data are confirmed by maintaining the visual axis for a specific period of time. The period during which the eyes are closed, i.e., the blinking period, can be changed, as will be described later.

(g) Seventh Embodiment

Figure 13:
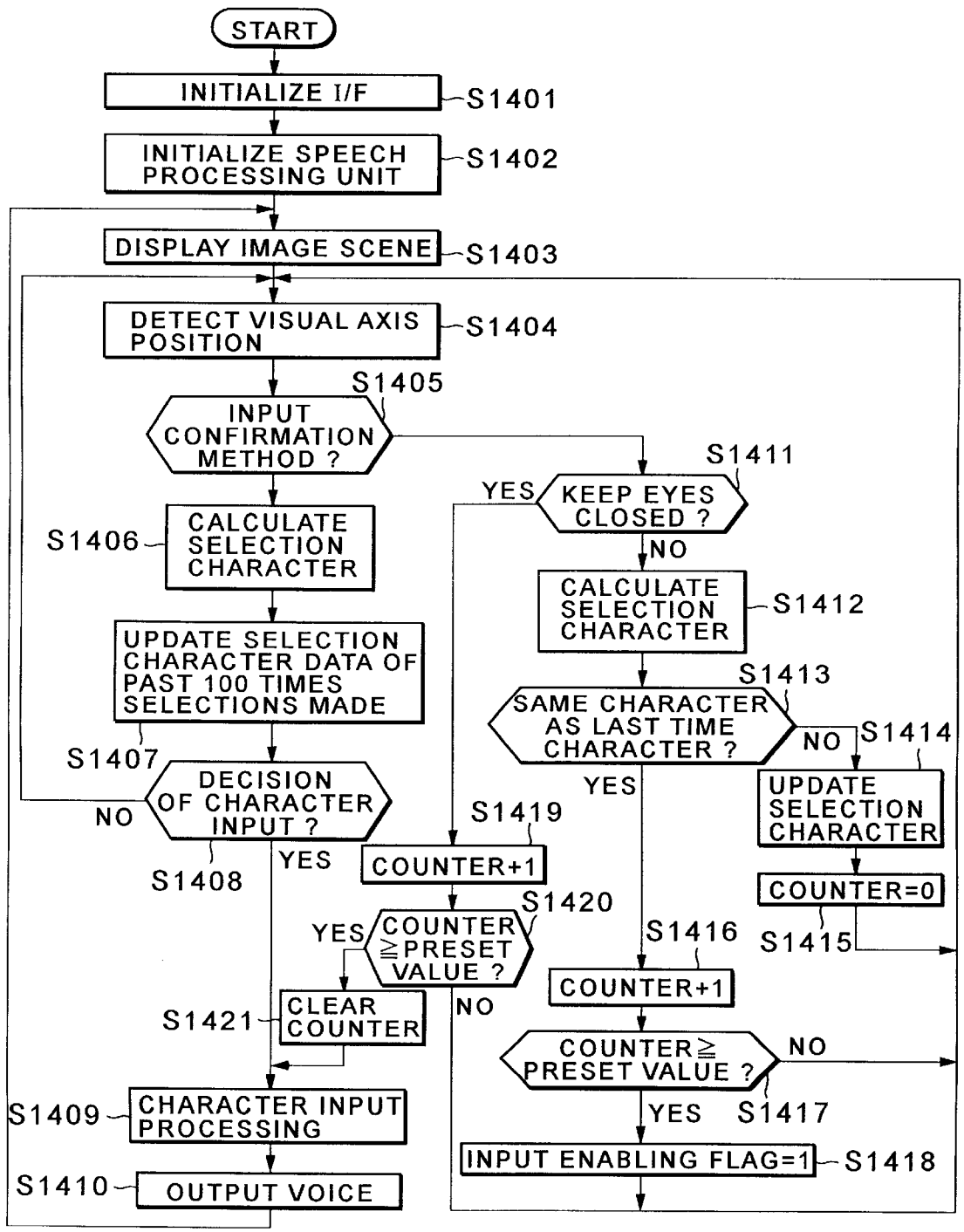
FIG. 13 is a flowchart showing the procedures performed by a visual axis entry transmission program according to a seventh embodiment of the present invention.

The arrangement of an apparatus according to a seventh embodiment is the same as that in the first embodiment. FIG. 13 is a flowchart showing the processing performed by a visual axis entry transmission program according to the seventh embodiment of the present invention. First, an I/F for a communication line is initialized (step S1401). In this embodiment, a serial port RS232C is opened and is set to the communication enabled state. Furthermore, a speech processing unit is initialized (step S1402).

50 hiragana characters (see FIG. 7), or katakana or alphabetical characters are displayed via a display controller 31 on the liquid crystal device 1002 of the head-mounted display unit 1006 and on the external monitor 1009 (step S1403).

Following this, the visual axis position data are detected (step S1404), and a check is performed to determine whether the currently selected input confirmation method is a method that requires the visual axis to be maintained for a specific period of time, or a method that requires the closing of eyes (step S1405).

Figure 14:
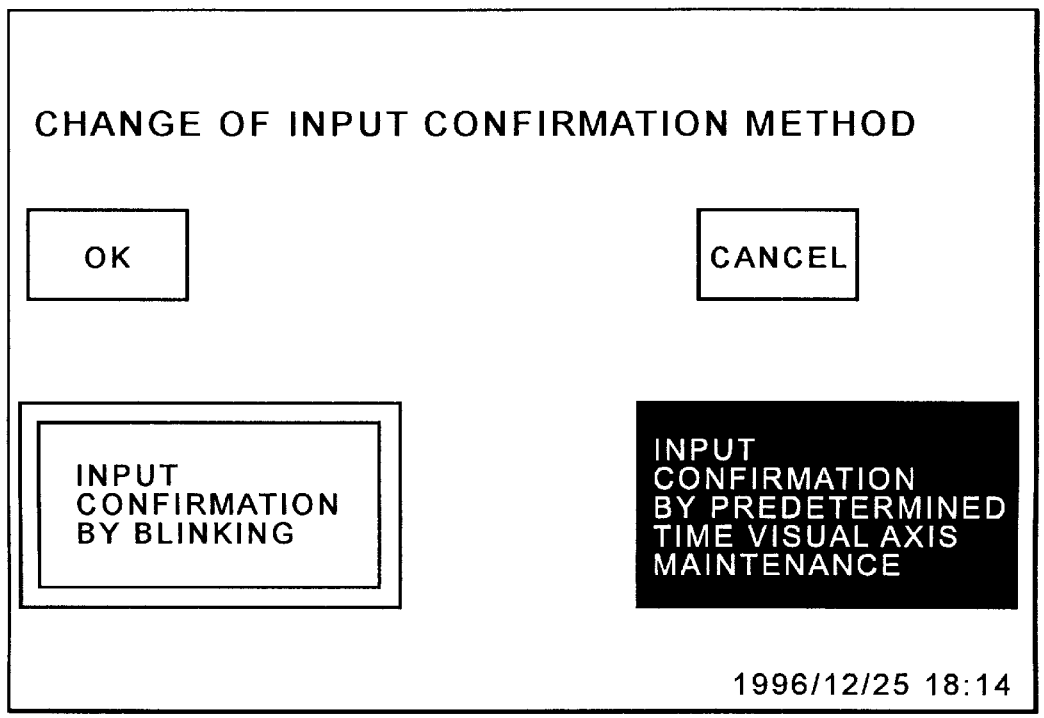
FIG. 14 is a diagram showing a screen (scene) for changing an input confirmation method.

FIG. 14 is a diagram showing a screen for changing the input confirmation method. Using this screen, the user 1 can select the input confirmation method to be used, either the method that requires the closing of eyes (blinking), or the method that requires the maintenance of the visual axis for a specific period of time. It should be noted that one of the input confirmation methods that are already set is selected.

When changing the input confirmation method, a visual axis maintenance period, a blinking time, or the number of characters on the display panel (keyboard) can also be changed.

Figure 15:
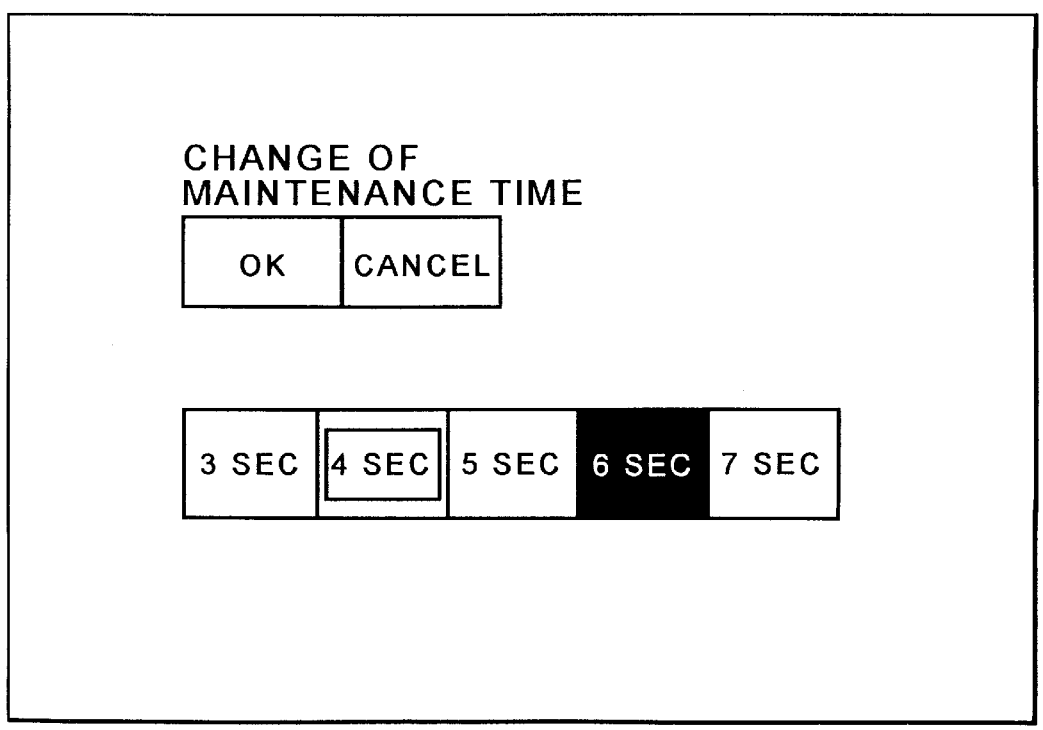
FIG. 15 is a diagram showing a screen for changing a maintenance time for a method for confirming input data by maintaining a visual axis for a predetermined period of time.

FIG. 15 is a screen for changing the maintenance time for the input confirmation method that requires the maintenance of the visual axis for a specific period of time. Using this screen, the user can select the visual axis maintenance period. The visual axis maintenance period can be set as units of seconds, of from 3 to 7 seconds. In this example, the current visual axis maintenance period, displayed with inverse video, is "6 seconds", and a currently selected period, enclosed by a double frame, is "4 seconds". When the enter key on the keyboard is pressed, the visual axis maintenance period will be changed from six seconds to four seconds. In addition, the time can be changed by using an arrow key on the keyboard.

Figure 16:
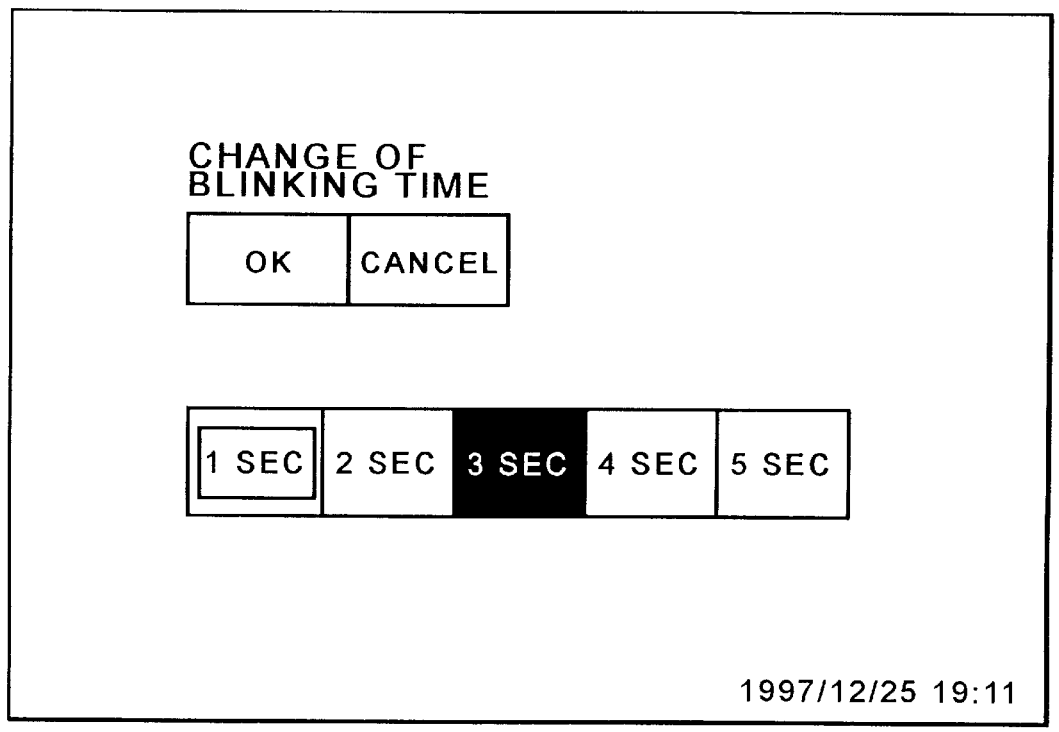
FIG. 16 is a diagram showing a screen for changing a blinking time for a method for confirming input data by the closing of the eyes of a user.
Figure 17:
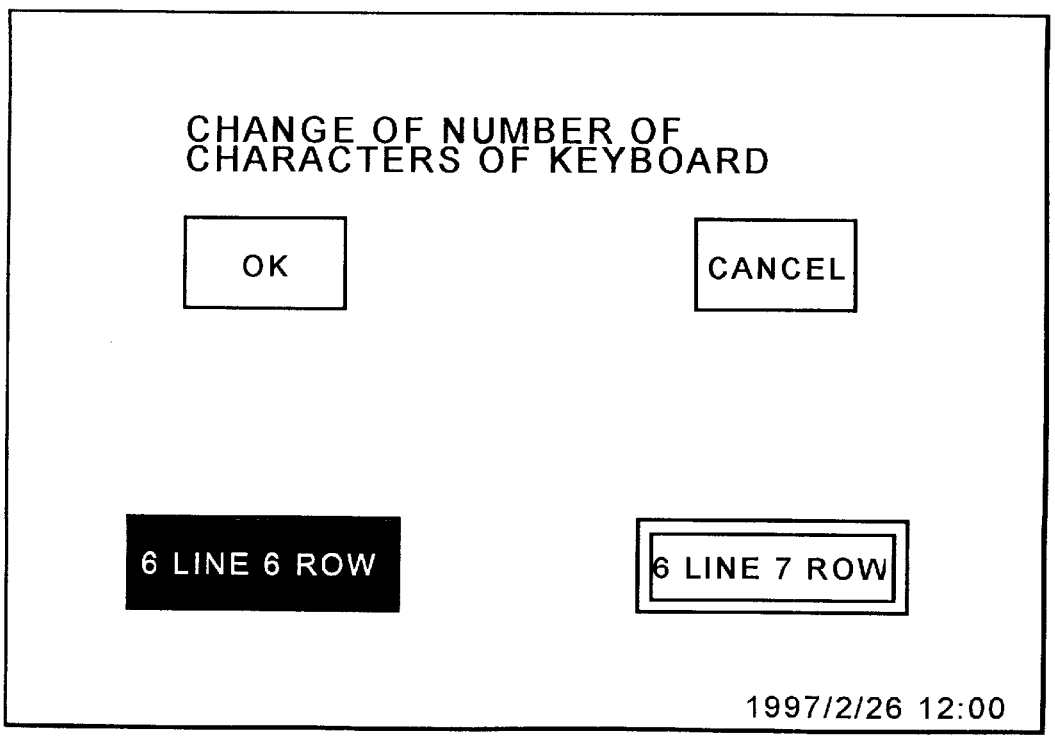
FIG. 17 is a diagram showing a screen for changing the number of characters displayed on a display panel.

FIG. 16 is a diagram showing a screen for changing the blinking time for the input confirmation method that requires the closing of the eyes. The blinking time can be set as units of seconds ranging from 1 to 5 seconds, and the user 1 can use this screen to change the blinking time. FIG. 17 is a diagram showing a screen for changing the number of characters on the display panel. The user 1 can use this screen to select the number of characters to be shown on the display panel (6 lines and 6 rows, or 6 lines and 7 rows). In FIGS. 16 and 17, the options shown in inverse video are the ones that are currently set, and the options that are enclosed in a double frame are the ones that have newly been selected. The same process is applied for the following display examples.

An explanation will now be given for a process where, at step S1405, an input character is confirmed by the method for which the visual axis is maintained for a specific period of time. The visual axis position data obtained at step S1404 are employed to acquire a character at the visual axis position (step S1406).

Data for the selected character are updated when it was one of the last 100 selections (step S1407). A check is performed to determine whether the condition for the entry of a character is satisfied by this new character selection (step S1408). The character entry condition is that, of character data in the last 100 selections, the number of selections of the pertinent character data exceeds the number that corresponds to the period of time the visual axis must be positioned on the same character for it to be entered, or it exceeds the number that corresponds to a constant ratio of the length of time the visual axis is positioned on the same character to a predetermined period of time.

When, at step S1408, the character entry condition is satisfied, a character is added to an input character string (step S1409), and the newly input character is pronounced (step S1410) in order to notify the user that the entry of the character has been completed. Program control thereafter returns to step S1403 to display the screen for a new input character.

When, at step S1408, the character entry condition is not satisfied, program control returns to step S1404, whereat a new visual axis position is detected to repeat the selection of a character.

An explanation will now be given for the method for confirming an input character by the closing of the eyes. When, at step S1405, the method for the closing of the eyes is selected as the input confirmation method, a check is performed to determine whether the visual axis position data obtained at step S1404 are those indicating the user's eyes are closed (step S1411).

When the visual axis data indicate the user's eyes are not closed, a character at the visual axis position is obtained based on the visual axis position data obtained at step S1404 (step S1412). That character is compared with a previously selected character to determine whether the two characters are the same (step S1413). When the two characters are the same, a counter value is incremented by one (step S1416).

Then, a check is performed to determine whether the updated counter value is equal to or greater than a preset value (step S1417). When the counter value is equal to or greater than the preset value, an input enabling flag is set to "1" (step S1418). The processes at steps S1413, S1416, S1417 and S1418 are performed in order to prevent a visual axis entry at the moment the user closes his or her eyes, and the erroneous input of a character that is not selected by the user. When at step S1417 the counter value does not reach the preset value, program control returns to step S1404.

When, as a result of the comparison at step S1413 the currently input character differs from the previously selected character, the selected character is updated (step S1414) and the counter is reset (step S1415). Program control thereafter returns to step S1404.

When at step S1411 the visual axis position data indicate that the user's eyes are closed, the counter value is incremented by one (step S1419). A check is performed to determine whether the counter value updated at step S1419 is equal to or greater than the preset value and whether the input enabling flag was set to "1" at step S1418 (step S1420).

When the counter value is equal to or greater than the preset value and the input enabling flag is set to "1", the counter is reset (step S1421). Program control moves to step S1409, whereat a character entry process is performed in the same manner as the input confirmation method whereby the visual axis must be maintained for a predetermined period of time.

When, at step S1420, the counter value is smaller than the preset value and the input enabling flag is not set to "1", program control returns to step S1404.

In the seventh embodiment, since the user can select either the input confirmation method for maintaining the visual axis for a specific period of time, or the input confirmation method for closing the eyes, the usability can be increased.

(h) Eighth Embodiment

A visual axis entry transmission apparatus according to an eighth embodiment can change from a character selection screen to a TV broadcast scene by selecting an option on a character selection screen, and is applied to the first to the seventh embodiments.

Figure 18:
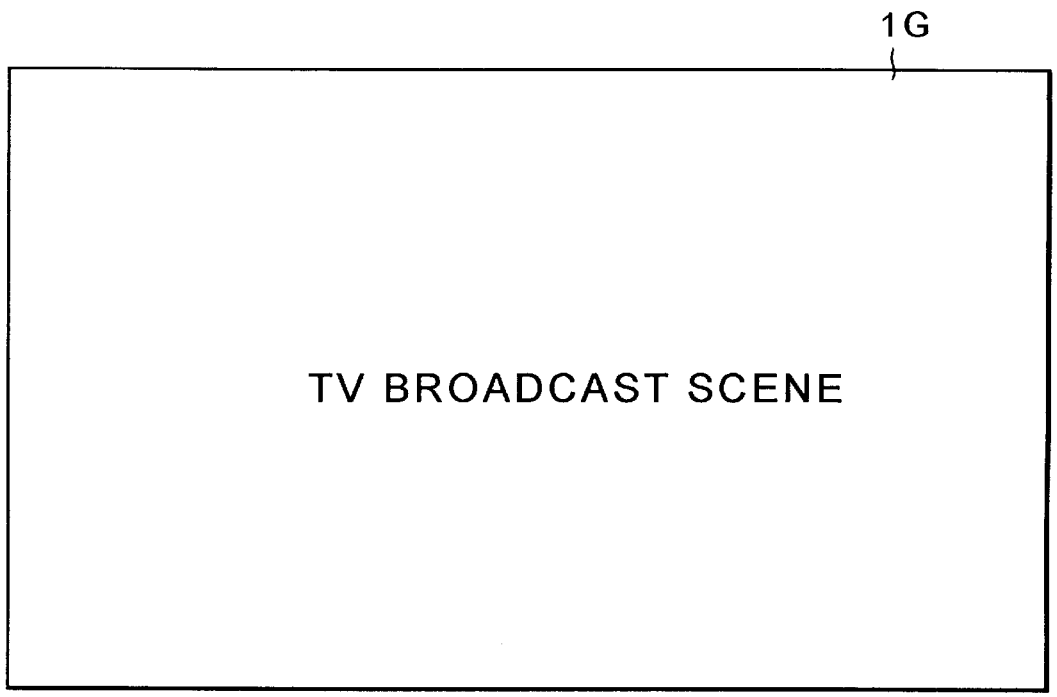
FIG. 18 is a diagram showing a TV broadcast scene when a TV is selected on a character selection screen.
Figure 19:
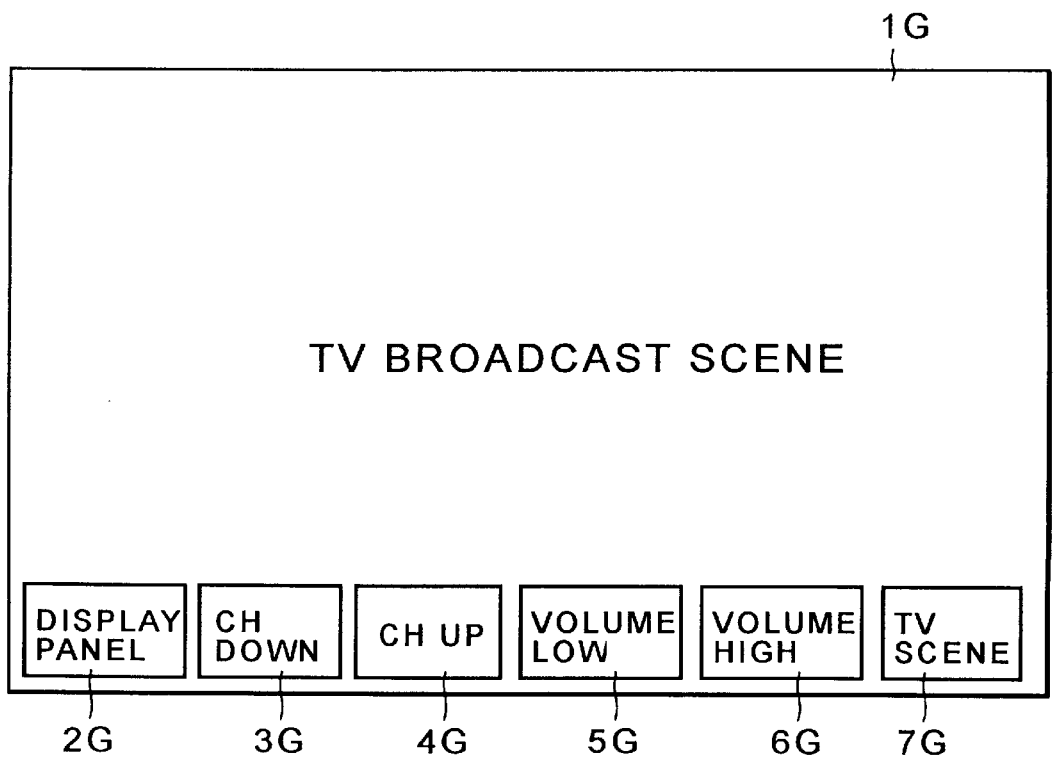
FIG. 19 is a diagram showing a TV broadcast scene in which options are displayed.

FIG. 18 is a diagram showing a TV broadcast scene when an option for a TV is selected on the character selection screen. When the TV is selected, the TV broadcast scene is displayed as a video for the first to the seventh embodiments. When the user gazes at the left upper corner (the left lower corner, the right upper corner or the right lower corner) on the screen for a predetermined period of time, options 2G to 7G (see FIG. 19) are displayed. FIG. 19 is a diagram showing the TV broadcast scene with the options displayed.

When the option 2G is selected, the screen is returned to the character selection screen in FIG. 7. When the option 3G is selected, the TV broadcast scene is changed to that at a smaller channel number. When the option 4G is selected, the TV broadcast scene is changed to that at a greater channel number. When the option 5G is selected, the volume is lowered. When the option 6G is selected, the volume is increased. When the option 7G is selected, the TV video is displayed on the entire monitor screen.

In the eighth embodiment, the user can select a desired screen by changing the display panel for character entry and the TV broadcast screen.

Not only the TV video, but also an externally input video image from a video recorder, a computer, a video-on-demand device, a clock, a crime prevention device or a video telephone, may be selected, so that the user can freely select various types of videos.

In addition, an external environment control screen may be provided to control an external environment device. With this screen, the user can freely control external environment devices, such as lighting apparatuses, televisions, audio devices, video recorders, computers, video-on-demand devices, telephones, video telephones, clocks, electric blinds, electric curtains, electric window opening/closing devices, air conditioners, crime prevention devices, electric reclining beds, excretion devices, lifters and nurse calling devices.

(i) Ninth Embodiment

The arrangement of an apparatus according to a ninth embodiment is the same as that in the first embodiment. For the visual axis entry transmission apparatus in the ninth embodiment, the user can adjust the visibility: the user moves the visual axis upward on the screen in order to increase the visibility, and moves the visual axis downward on the screen in order to reduce the visibility. To terminate the adjustment of the visibility, the user moves the visual axis to the center on the screen.

Figure 20:
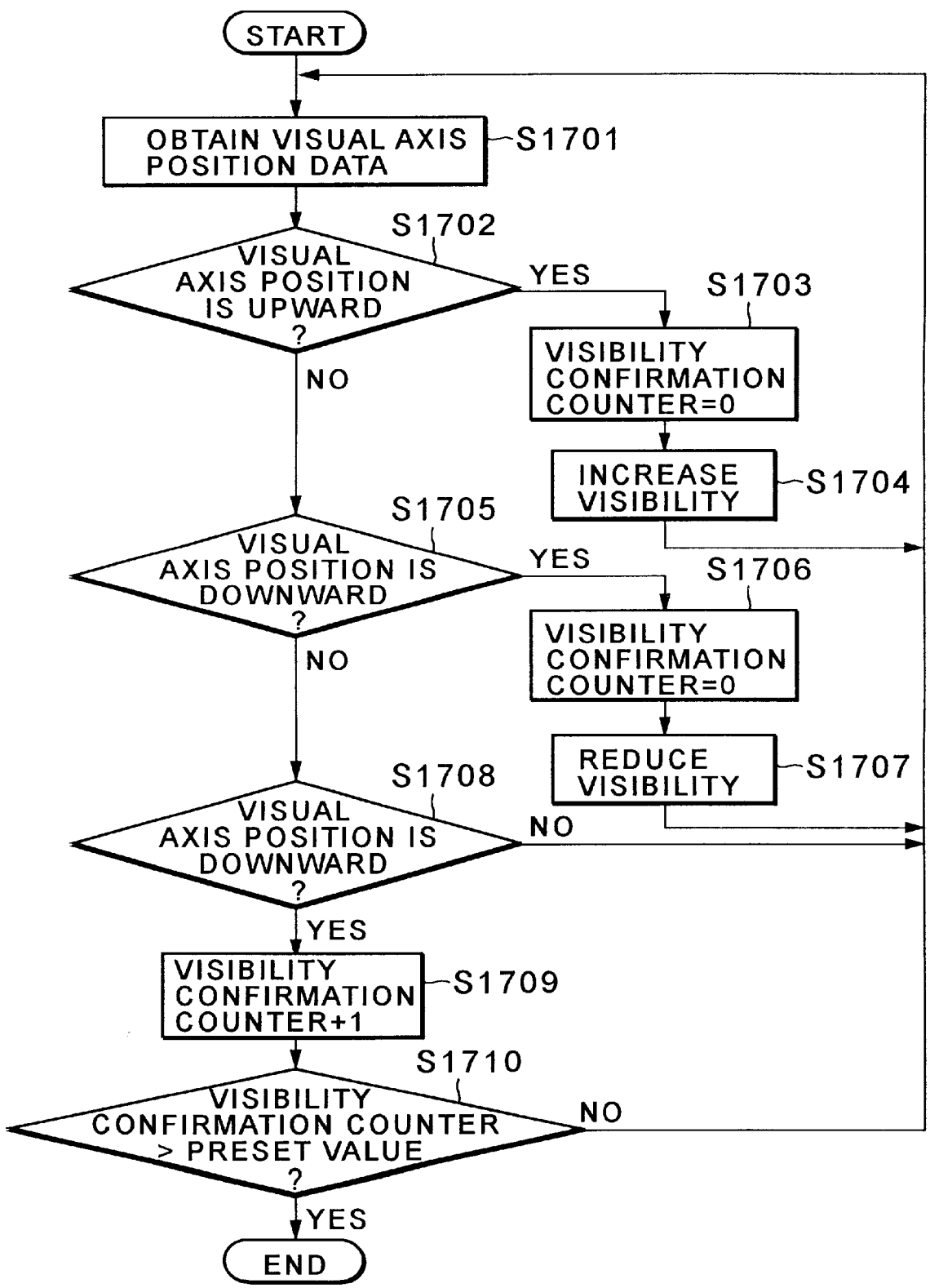
FIG. 20 is a flowchart showing visibility adjustment processing performed according to a ninth embodiment of the present invention.

FIG. 20 is a flowchart showing the visibility adjustment processing according to the ninth embodiment. The program is stored in a ROM 1816 and is executed by a CPU 1814. First, visual axis position data are acquired by a visual axis detection circuit (step S1701). A check is then performed to determine whether the visual axis position data obtained at step S1701 indicate a value higher than the preset value (step S1702).

When the visual axis position data indicate a value higher than the preset value, the visibility counter used for establishing the visibility is set to "0" (step S1703). Thereafter a computer 4 transmits a command to a head-mounted display unit 1006 to increase the visibility (step S1704). Program control thereafter returns to step S1701.

When, at step S1702, the visual axis position data are not higher than the preset value, a check is performed to determine whether the visual axis position data are lower than the preset value (step S1705). When the visual axis position data are lower than the preset value, the visibility counter used for establishing the visibility is set to "0" (step S1706), and the computer 4 issues a command to the head-mounted display unit 1006 to reduce the visibility (step S1707). Program control thereafter returns to step S1701.

When, at step S1705, visual axis position data below the preset value are not present, a check is performed to determine whether the visual axis position data are in a preset area in the center on the screen (step S1708).

When the visual axis position data are located in the preset area in the center on the screen, the visibility counter value is incremented by one (step S1709). Then, a check is performed to determine whether the visibility counter value is greater than the preset value (step S1710). When the visibility counter value is greater than the preset value, it is assumed that the visibility has been adjusted, and the processing is thereafter terminated.

When, at step S1710, the visibility counter value is equal to or smaller than the preset value, program control returns to step S1701. And when, at step S1708, the visual axis position data are not located in the preset area in the center on the screen, program control also returns to step S1701.

In the ninth embodiment, the visibility can be adjusted to suit the user.

(j) Tenth Embodiment

The arrangement of an apparatus according to a tenth embodiment is the same as that in the first embodiment, except that in the tenth embodiment a switch (not shown) used to confirm an input character is connected to an I/O channel 1819. This program is stored in the ROM 1816 of the personal computer unit 1008 and is executed by the CPU 1814.

Figure 21:
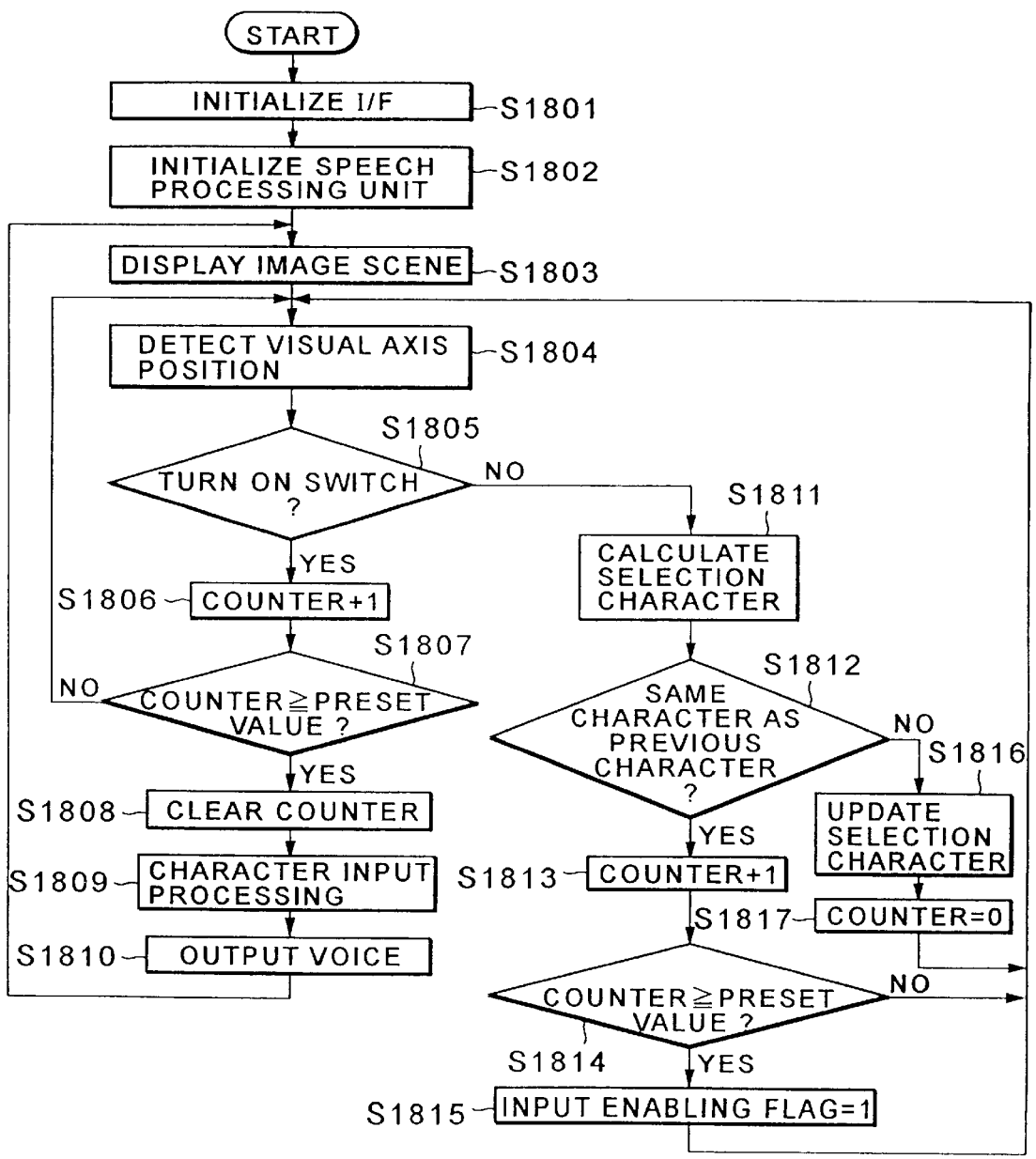
FIG. 21 is a flowchart showing the procedures performed by a visual axis entry transmission program according to a tenth embodiment of the present invention.

FIG. 21 is a flowchart showing the processing of a visual axis entry transmission program according to the sixth embodiment of the present invention.

First, an I/F for a communication line is initialized (step S1801). In this embodiment, a serial port RS232C is opened and is set to the communication enabled state. Then, a speech processing unit is initialized (step S1802). 50 hiragana characters (see FIG. 7), or katakana or alphabetical characters, are displayed via a display controller 31 on the liquid crystal device 1002 of the head-mounted display unit (visual axis input scouter) 1006 and on the external monitor 1009 (step S1803).

Following this, the visual axis position data are detected (step S1804). A check is performed to determine whether a switch for confirming the entry has been depressed (step S1805). When the switch for confirming the data entry has not been depressed, a character at the visual axis position is obtained based on the visual axis position data (step S1811).

That character is compared with the previously selected character to determine whether the two characters are the same (step S1812). When the two characters are the same, a counter value is incremented by one (step S1813). Then, a check is performed to determine whether the updated counter value is equal to or greater than a preset value (step S1814). When the counter value is equal to or greater than the preset value, an input enabling flag is set to "1" (step S1815).

When at step S1814 the counter value does not equal the preset value, program control returns to step S1804. When, as the result of the comparison at step S1812, the currently input character differs from the previously selected character, the selected character is updated (step S1816) and the counter is reset (step S1817). Program control thereafter returns to step S1804.

When at step S1805 the switch for confirming the entry has been depressed, the counter value is incremented by one (step S1806). A check is then performed to determine whether the counter value incremented at step S1806 is equal to or greater than the preset value and whether the input enabling flag is set to "1" (step S1807). When the counter value is equal to or greater than the preset value and the input enabling flag is set to "1", the counter is reset (step S1808). A character entry process is performed in the same manner as the input confirmation method for which the visual axis is maintained for a predetermined period of time (step S1809), and voice is output (step S1810). Program control thereafter returns to step S1803.

When at step S1807 the counter value is smaller than the preset value, program control returns to step S1804.

In the tenth embodiment, since the user can confirm the input data only by moving his or her eyes and slightly depressing the switch, the operation requiring the use of the eyes can be reduced. The switch may be worn on the head, or may be held in a hand. The user may set an arbitrary period of time during which the switch must be depressed before the selected character is confirmed. Since an adequate on-time period for the switch is set for each user, the useability can be enhanced.

An explanation will now be given for the character selection screen, which is the video image shown on the display panel according to the first to the tenth embodiments, and the functions of the individual options.

FIG. 22 is a diagram showing the first page for the hiragana character selection screen; FIG. 23 is a diagram showing the second page for the hiragana character selection screen; and FIG. 24 is a diagram showing the third page for the hiragana character selection screen. The individual options on the character selection screen are as follows:

"Cancellation": Cancels a character that was previously entered; cancels "dots" or "semi-dots" that were previously entered; cancels the movement of a cursor in a sentence display portion that was previously input; cancels the clearing, the last character deletion or the performance of a deletion that was previously entered; cancels a "Yes" or "No" that was previously entered; or cancels a "cancel" that was previously entered.

"Function": Displays a function item selection screen for selecting various functions of the visual axis entry transmission apparatus.

"Registration": Registers a created sentence and deletes a registered sentence.

"Call": Retrieves a registered sentence.

"Utterance": Pronounces a created sentence.

"‒": Entered to indicate a prolonged sound in a hiragana or katakana input mode, and to indicate a hyphen in an upper case and in a lower case alphabetical mode.

"ゞ (dots)": Entered to indicate a voiced consonant. First, a character to which dots can be added (the か,さ,た or は, or う column) is entered and then "dots" are entered.

"゜ (semi-dots)": Entered to indicate a plosive sound. First, a character to which semi-dots can be added (the は column) is entered and then "semi-dots" are entered.

"Δ": Changes from the second or third page for the character selection screen to the first page. No shift is performed on the first page for the character selection screen.

"Λ": Changes from the second page for the character selection screen to the first page, or changes from the third page for the character selection screen to the second page. No shift is performed on the first page for the character selection screen.

"V": Changes from the second page for the character selection screen to the third page, or changes from the first page for the character selection screen to the second page. No shift is performed on the third page for the character selection screen.

"▽": Changes from the first or second page for the character selection screen to the third page. No shift is performed on the third page for the character selection screen.

"◁": Moves the cursor in the sentence display portion to the left one space.

"Clear": Clears a created sentence.

"Preceding last character deletion": Deletes a character immediately to the left of the cursor in the sentence display portion.

"Deletion": Deletes a character at the position of the cursor in the sentence display portion.

"Yes"/"No": Enters "Yes" or "No". These keys are used by a user for an immediate response upon receipt of a query from a third party.

"▷": Moves the cursor in the sentence display portion to the right one space.

As is described, since many options are provided on the character selection screen by changing the page, various functions can be selected by the user.

Figure 26:
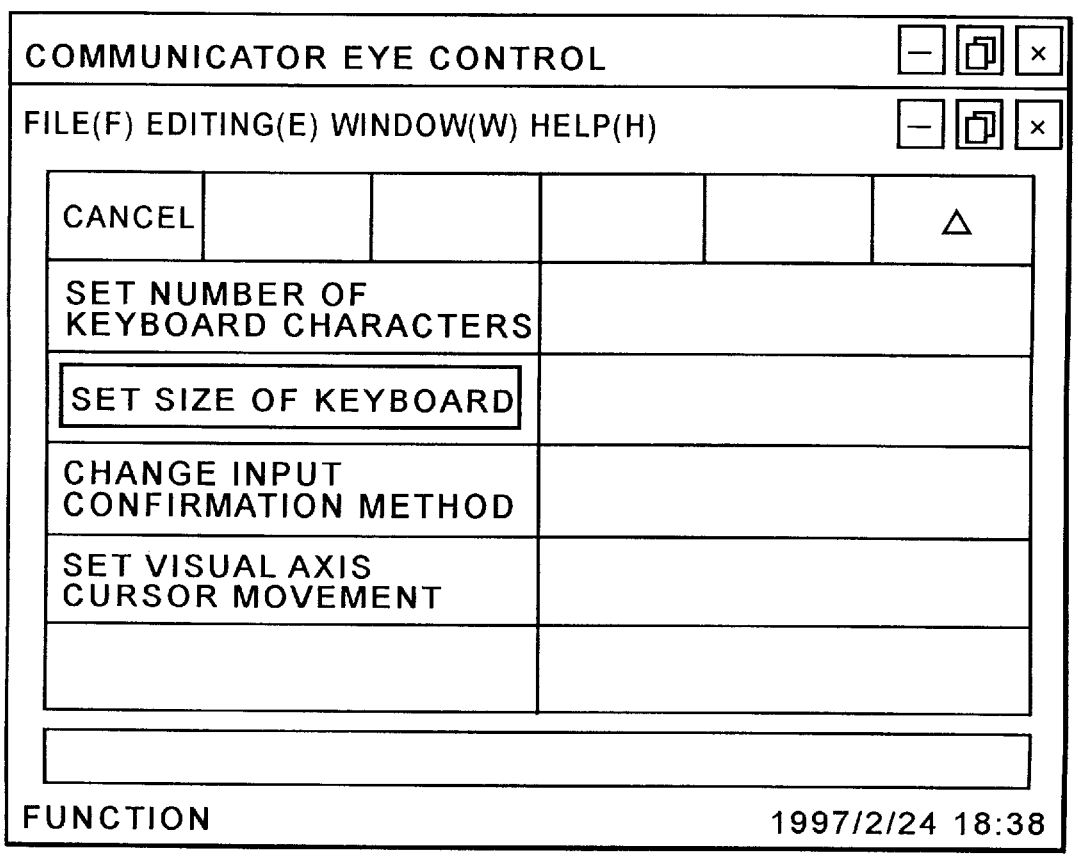
FIG. 26 is a diagram showing function selection screen 2.

FIG. 25 is a diagram showing function selection screen 1 displayed when the user selects "Function" on the character selection screen, and FIG. 26 is a diagram showing function selection screen 2.

The user selects options to change various preset values for the visual axis entry transmission apparatus. When the user selects "Cancellation", the screen is returned to the character selection screen (see FIG. 22). The shift from the function selection screen 1 to the function selection screen 2 can be performed by selecting "▽" on the function selection screen 1. The shift from the function selection screen 2 to the function selection screen 1 can be performed by selecting "Δ".

Figure 27:
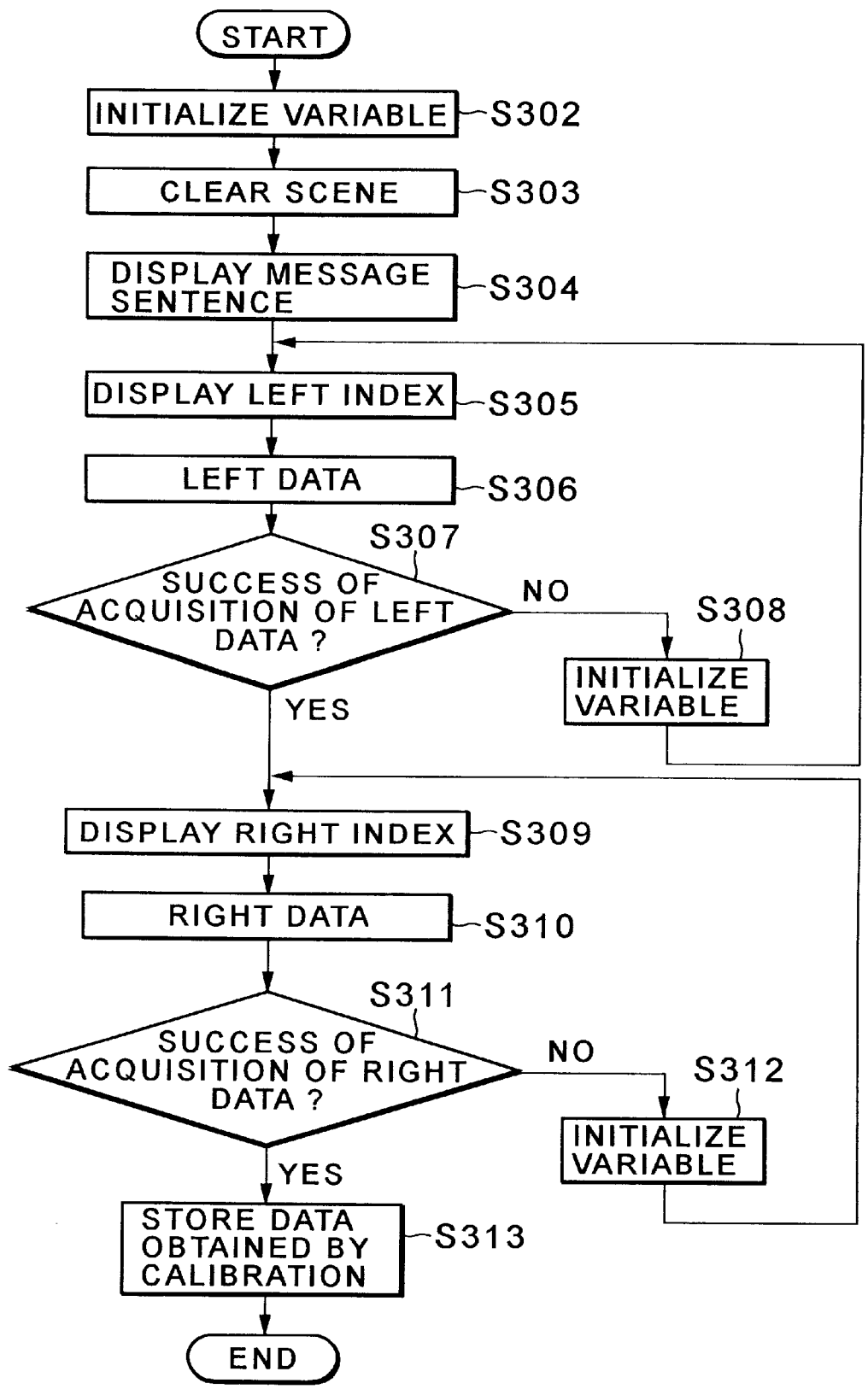
FIG. 27 is a flowchart showing calibration processing.

"Calibration" on the function selection screen 1 will now be explained. FIG. 27 is a flowchart showing the calibration processing. First, a status variable (NAC_STAT) for calibration is initialized (step S302). When the screen is cleared (step S303), the message for performing calibration is displayed (step S304).

The left index is displayed at a position where theoretically the eyeball is inclined six degrees from the front to the left (step S305), and the left calibration data are acquired (step S306). A check is performed to determine whether the acquisition of the left calibration data was successful (step S307). When the acquisition of the left calibration data failed, the status variable (NAC_STAT) is initialized again (step S308). Program control thereafter returns to step S305.

When the acquisition of the left calibration data was successful, a statement to that effect is displayed, and the right index is displayed at a position where theoretically the eyeball is inclined six degrees from the front to the right (step S309), and the right calibration data are acquired (step S310). A check is performed to determine whether the acquisition of the right calibration data was successful (step S311). When the acquisition of the right calibration data failed, the status variable (NAC_STAT) is initialized again (step S312). Program control thereafter returns to step S309.

When the acquisition of the right calibration data was successful, a statement to that effect is displayed. Since theoretically the acquisition of the left and right calibration data was successful, these data are written to the EEPROM of the head-mounted display unit 1006, or the glasses, with the visual axis detection function, and a calibration data output message is displayed (step S313). The processing is thereafter terminated.

The calibration is performed when the visual axis entry transmission apparatus is activated, or when "Calibration" on the function selection screen 1 is selected.

Figure 28:
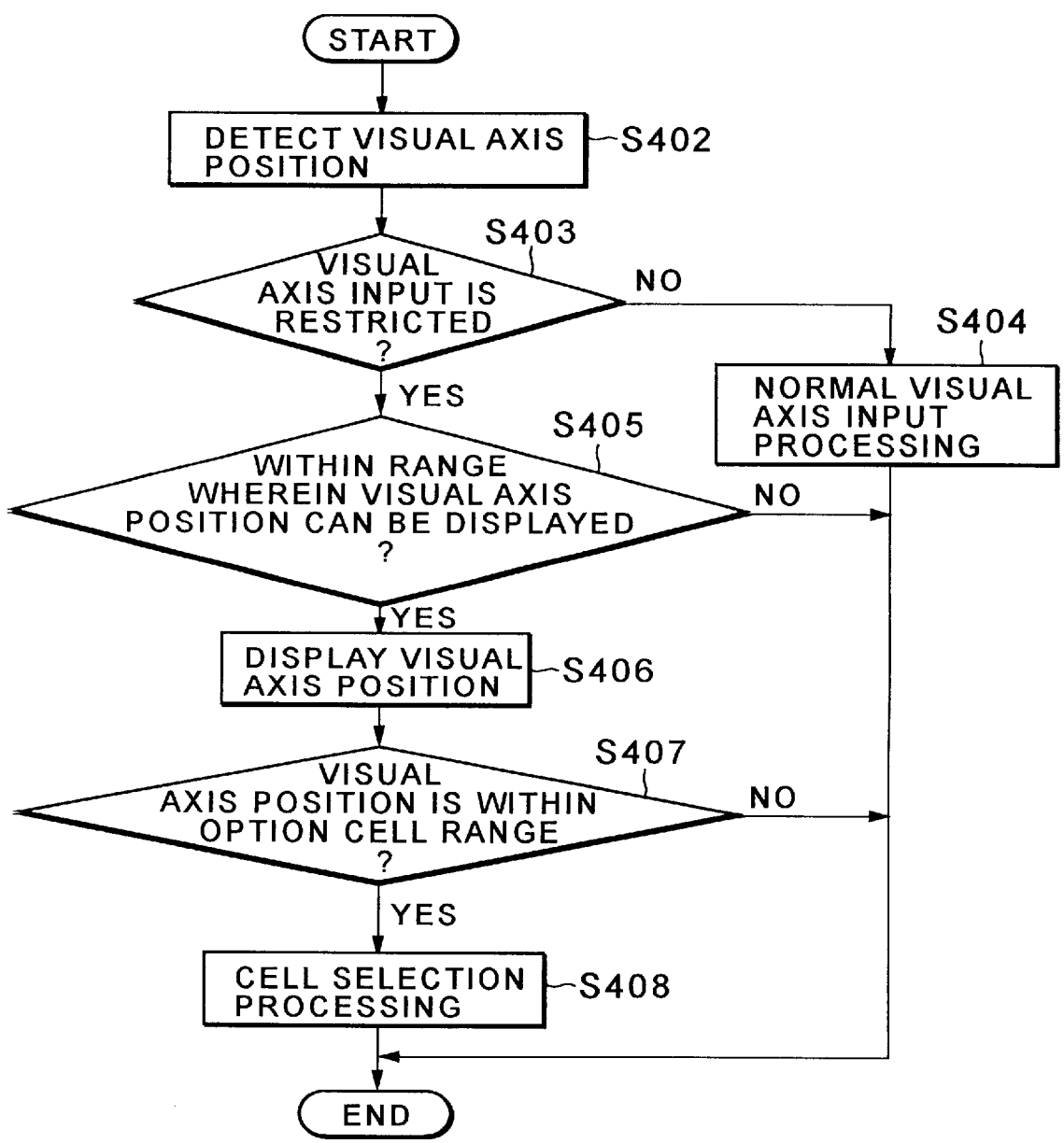
FIG. 28 is a flowchart showing the processing concerning the entry of data when, before taking a recess, a user erases a screen display and reduces an available range for visual axis entry.

"Recess" on the function selection screen 1 will now be described. FIG. 28 is a flowchart showing the entry processing when, to take a recess, a user clears the screen and narrows a visual axis entry available range. First, visual axis position data are acquired in synchronization with the timer (step S402). A check is then performed to determine whether the visual axis entry is restricted (step S403).

When the visual axis entry is not restricted, the normal visual axis entry process is performed (step S404). When the visual axis entry is restricted, a check is performed to determine whether the visual axis position is within a range wherein the visual axis position can be displayed (step S405). When the visual axis position is outside that range, the processing is terminated.

If the visual axis position is within the range where the visual axis position can be displayed, that position is displayed (step S406). A check is then performed to determine whether the visual axis position is within an option cell (step S407). When the visual axis position is outside the option cell, the processing is terminated.

If the visual axis position is within the option cell, the cell selection processing is performed (step S408). Thereafter, the processing is terminated.

Figure 29:
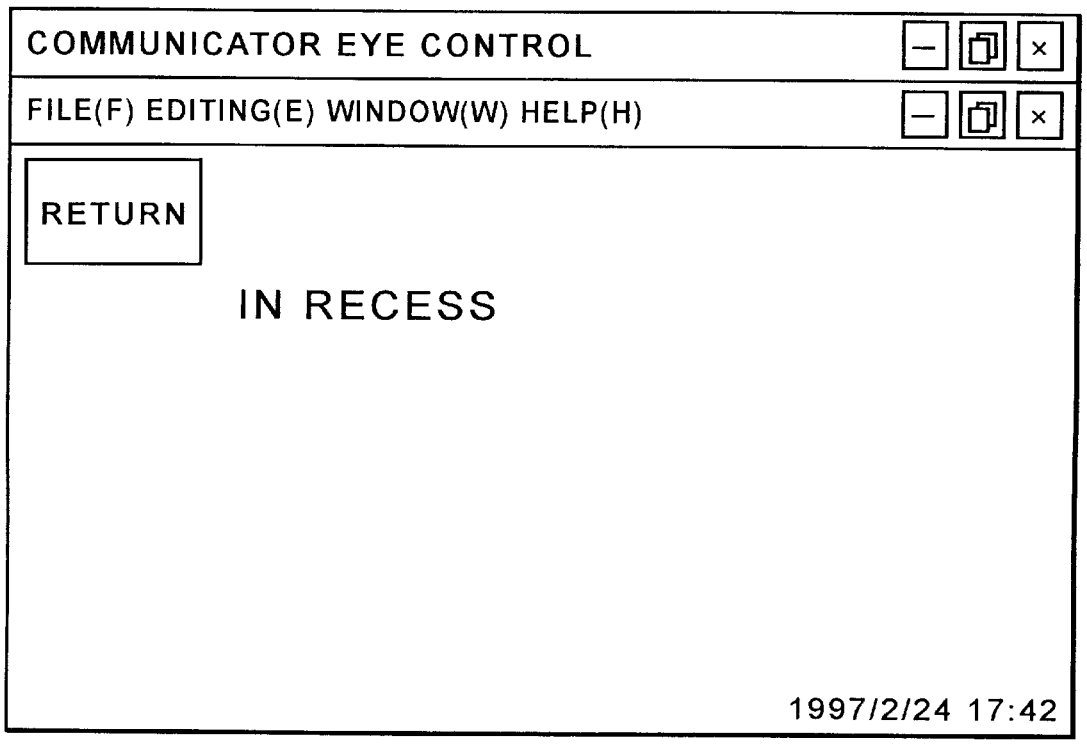
FIG. 29 is a diagram showing a normal input screen in a recess mode.

The visual axis position display range at step S405 and the option cell range at step S407 do not always match. FIG. 29 is a diagram showing the normal input screen in the recess mode. In the recess mode, option cells are not displayed, except for a "Return" cell for returning to the normal input screen.

When the user desires to select "Return" to return to the normal selection screen, if for a specific reason the actual visual axis position of the user is shifted away from the visual axis position detected by the visual axis detection circuit (the visual axis position displayed on the display device), and if the visual axis position is displayed only when it is located within the option cell "Return", the user does not know how far the detected visual axis position is from the actual position and does not know how to control the visual axis in order to move the detected visual axis position into the "Return" cell. In order to avoid such a situation, the visual axis position is displayed as it approaches the "Return" cell.

The user can recess a session by selecting "Recess" on the function selection screen 1, by closing his, or her, eyes for a predetermined period of time, by staring at one of the corners on the screen, or by entering data using the input confirmation condition process. Further, the direction in which the user's line of sight is directed may be arbitrarily changed, so that usability can be improved.

Figure 30:
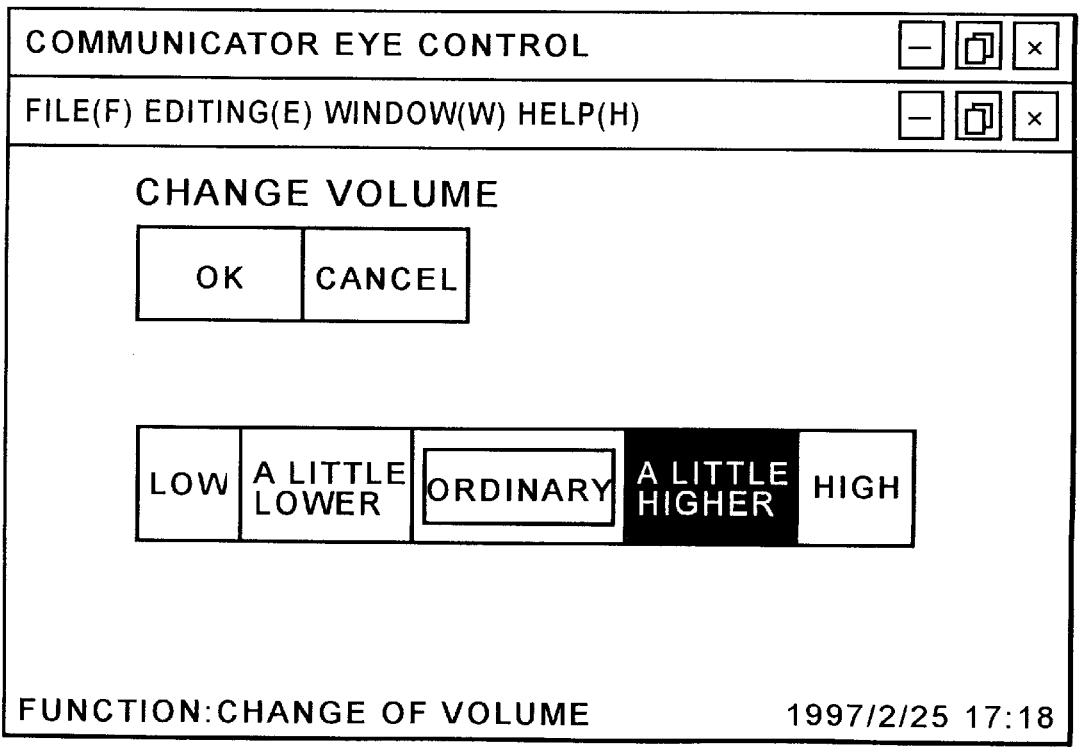
FIG. 30 is a diagram showing a screen for changing volume.

The "Change of volume" function on the function selection screen 1 will now be explained. FIG. 30 is a diagram showing a screen that the user can employ for changing the volume. When "Low" is selected, the amplitude of a speech waveform is ⅕ times that of the "Ordinary" level. Similarly, when "A Little Lower" is selected, the amplitude of the waveform is reduced to ½ times that of the "Ordinary" level. When "A Little Higher" is selected, the amplitude of the waveform is doubled, and when "High" is selected, the amplitude of the waveform is increased five times. To change the volume, the user selects "Change volume" on the function selection screen 1.

Figure 31:
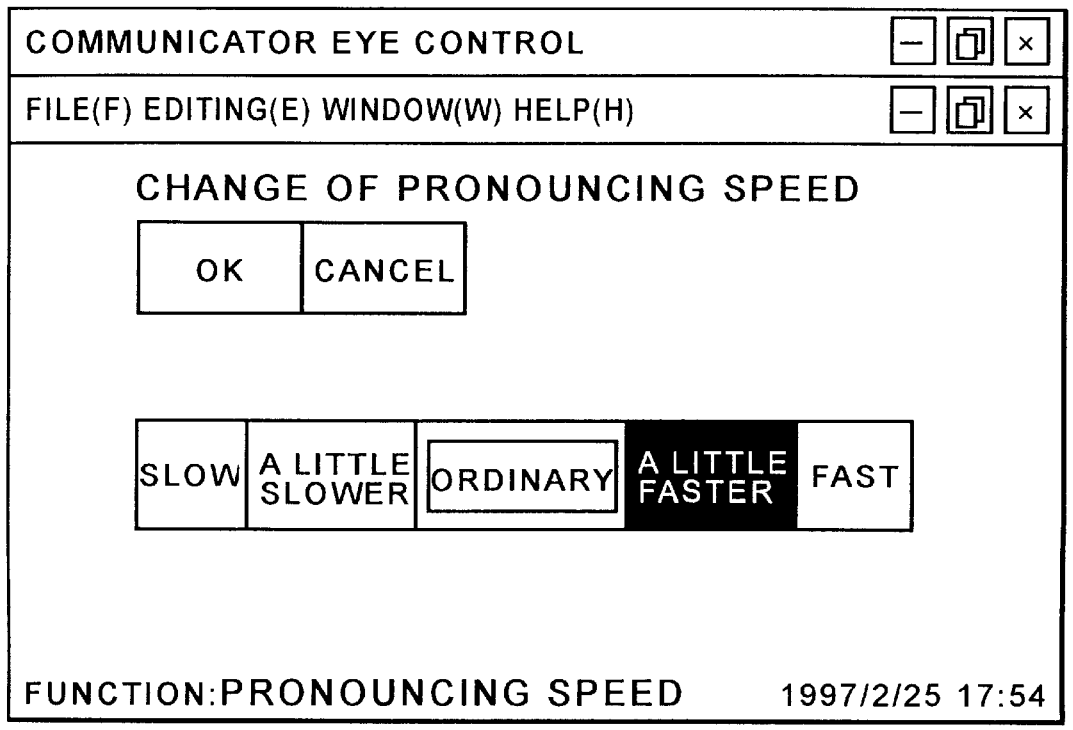
FIG. 31 is a diagram showing a screen for changing pronouncing speed.

The "Change pronouncing speed" function on the function selection screen 1 will now be explained. FIG. 31 is a diagram showing a screen the user can employ to change the pronouncing speed. When "Slow" is selected, the speed is 170 msec/mora; when "A Little slow" is selected, the speed is 150 msec/mora; when "Ordinary" is selected, the speed is 130 msec/mora; when "A Little Fast" is selected, the speed is 110 msec/mora; and when "Fast" is selected, the speed is 90 msec/mora. To change the pronouncing speed, "Change Pronouncing Speed" is selected on the function selection screen 1.

Figure 32:
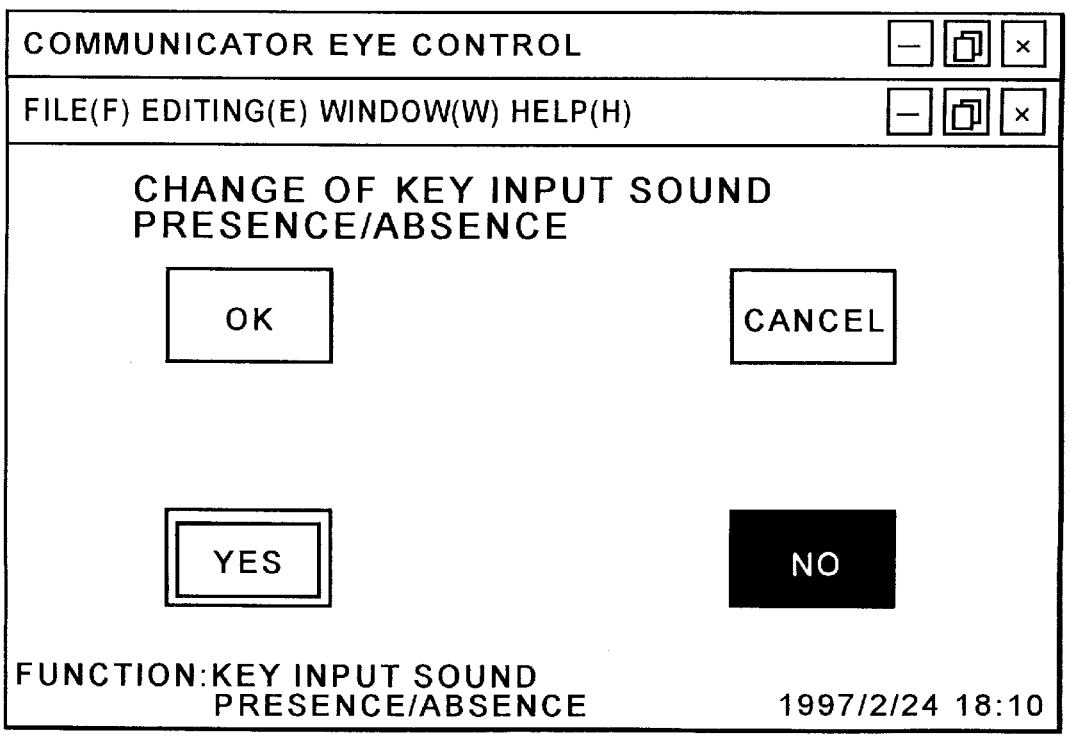
FIG. 32 is a diagram showing a screen for setting or canceling a function for reading the name of an option that is selected by a user.

The "Set key volume" function on the function selection screen 1 will now be described. FIG. 32 is a diagram showing a screen for setting or canceling the function for uttering the name of a choice (option) when it is selected. When "Yes" is selected, the name of a choice is uttered at the time it is selected. When "No" is selected, the name of a choice is not uttered, even when it is selected. In either case, a sentence that has been created is uttered when "Utterance" is selected.

Figure 33:
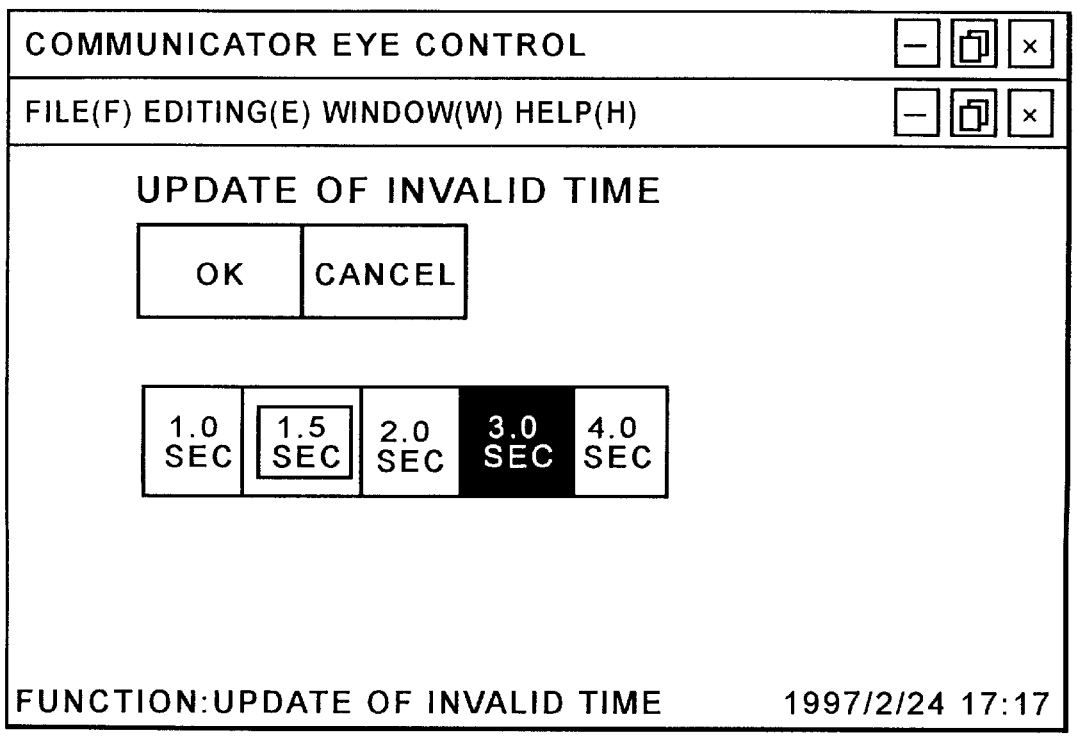
FIG. 33 is a diagram showing a screen for changing an invalid time.

The "Change maintenance time" function on the function selection screen 1 will now be described. FIG. 33 is a diagram showing a screen for changing the invalid time. On this screen the user can select the timing for the invalid time. To change the invalid time, "Change maintenance time" is selected on the function selection screen 1.

Figure 34:
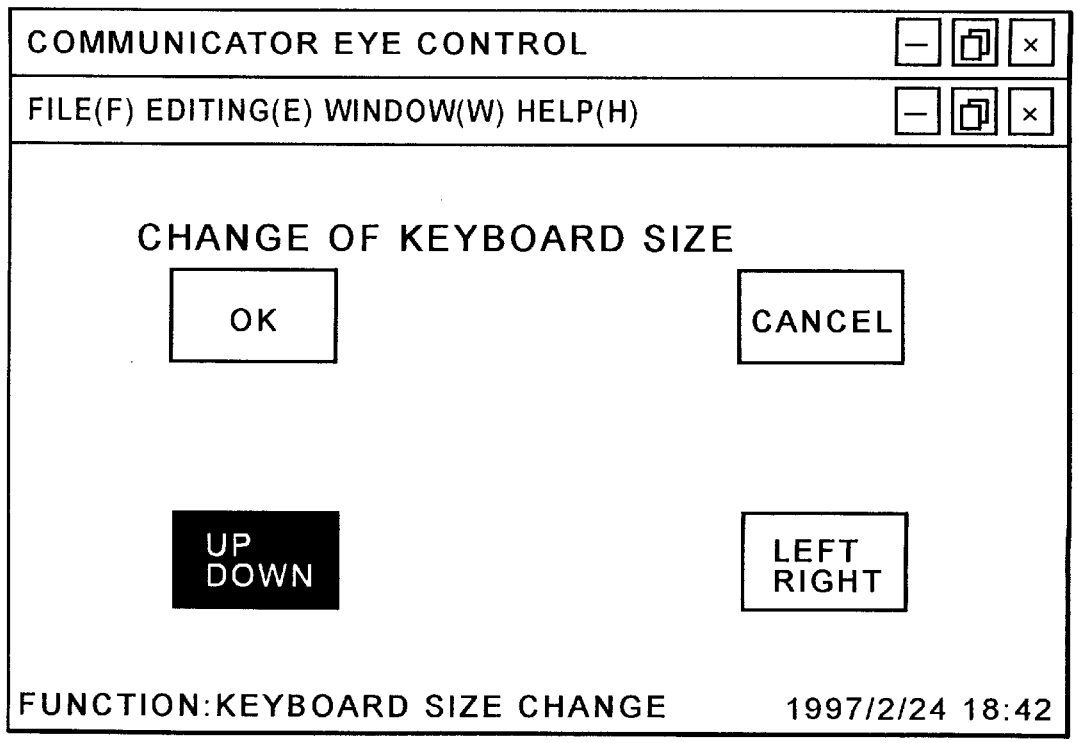
FIG. 34 is a diagram showing a screen for changing the size of a keyboard.
Figure 35:
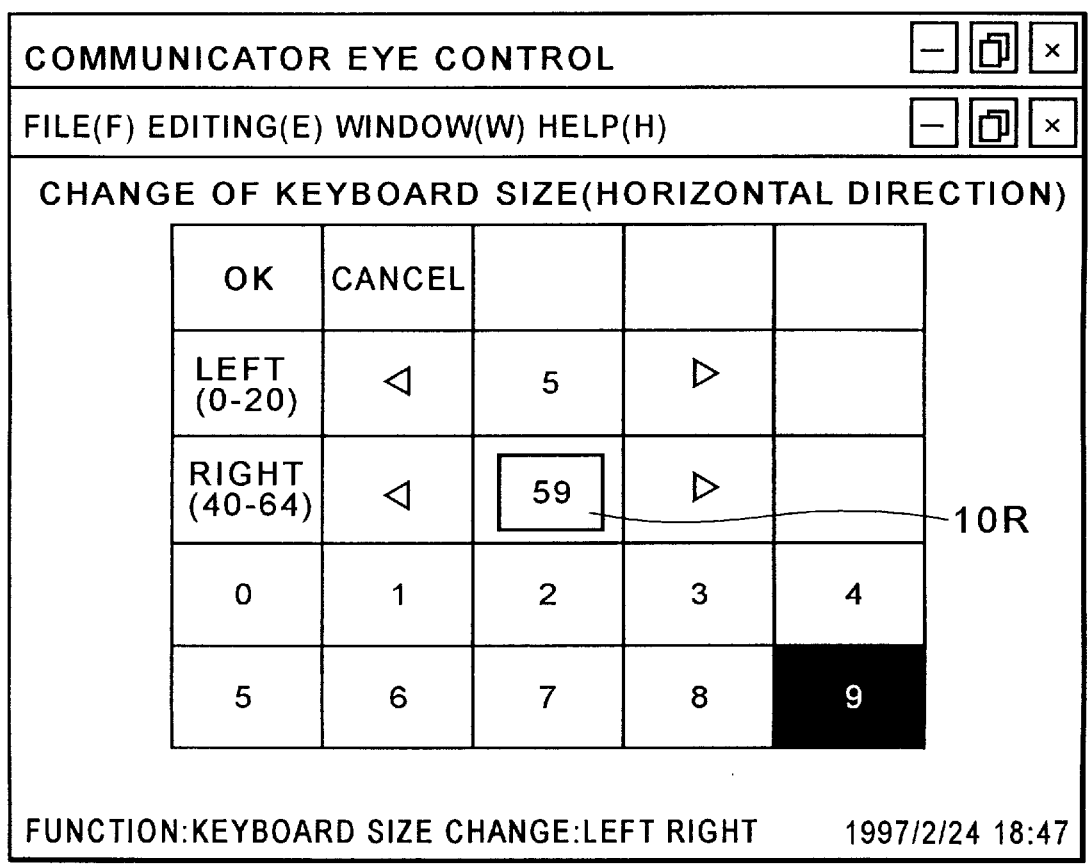
FIG. 35 is a diagram showing a screen for changing the transverse (horizontal) size of a keyboard.

The "Set size of keyboard" function on the function selection screen 2 will now be described. FIG. 34 is a diagram showing a screen for changing the overall size of a keyboard, and FIG. 35 is a diagram showing a screen for changing the size of a keyboard in the horizontal direction. When the user selects "Set size of keyboard" on the function selection screen 2, the screen is switched to that one shown in FIG. 34.

The user selects "Up/Down" or "Left/Right" to change the size of the keyboard (display panel) in either the vertical direction or the horizontal direction.

An explanation will be given for changing the size of the keyboard in the horizontal direction. When the user selects "Left/Right" in FIG. 34, the screen in FIG. 35 is displayed. The second numeral from the top in the third column from the left is the margin between the left edge of the screen and the left edge of the keyboard.

The third numeral from the top in the third column from the left in FIG. 35 is the distance between the right edge of the screen and the right edge of the keyboard (assuming this numeral is A, the margin from the right edge of the screen and to the right edge of the keyboard is represented as 64—A).

Two methods are provided for changing these numerals. According to the first method, a numeral is changed by selecting an arrow on the left or right side of the numeral. According to the second method, a numeral is selected (a red frame 10R is displayed when it is selected) and an option of "0" to "9" is chosen to directly input the numeral. The numeral is determined and the "OK" cell is selected to confirm the setup.

Similarly, an explanation will be given for the change in the size of the keyboard in the vertical direction. FIG. 36 is a diagram showing a screen for changing the size of the keyboard in the vertical direction. When "Up/Down" is selected in FIG. 34, the screen in FIG. 36 is displayed. In the table, the third numeral from the top in the second column from the left is the margin between the lower edge of the menu bar of a window provided by Windows95 (Microsoft Corp.) and the upper edge of the keyboard. And in the table, the third numeral from the top in the fifth column from the left is the distance between the lower edge of the menu bar and the lower edge of the keyboard (assuming this numeral is A, the margin between the upper edge of the input character display portion and the lower edge of the keyboard is represented as 37—A).

Two methods are provided for changing these numerals. According to the first method, a numeral is changed by selecting an arrow above or below the numeral. According to the second method, a numeral is selected (a red frame 20R is displayed when it is selected) and an option of "0" to "9" is selected to directly input the numeral. The numeral is determined and the "OK" cell is selected to confirm the setup.

FIG. 37 is a diagram showing the character selection screen after the size of the keyboard has been changed. This character selection screen is provided by selecting the numerals in the horizontal direction and in the vertical direction as left, 5, and right, 59, and up, 5, and down, 32. The setting of the numerals "1" in the vertical and in the horizontal direction is equivalent to a change of 10 dots on the screen.

Figure 38:
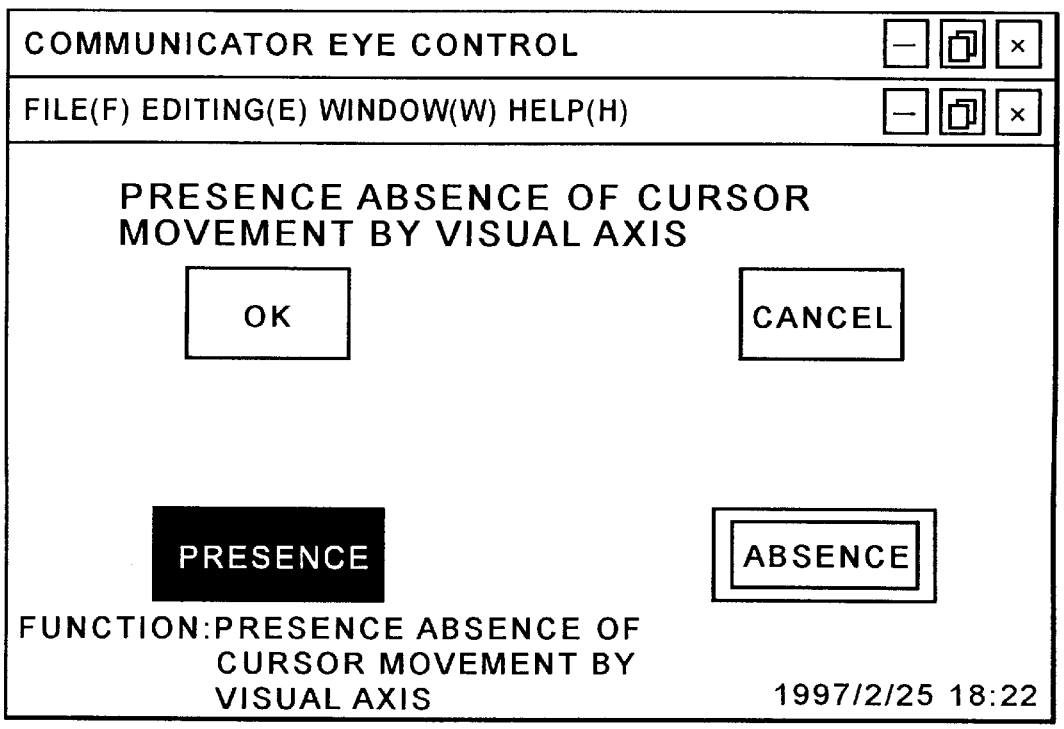
FIG. 38 is a diagram showing a screen for setting or canceling a cursor to move to the visual axis position of a user when the user focuses on a created sentence display portion of the character selection screen.

The "Set visual axis cursor movement" function on the function selection screen 2 will now be explained. FIG. 38 is a diagram showing a screen for changing the setup when determining whether the cursor should be moved to a visual axis position when the visual axis is positioned on the sentence display portion on the character selection screen. When "Presence" is selected, the visual axis is positioned at an arbitrary location in the sentence display portion on the character selection screen. And when the entry is confirmed by the input confirmation method, the cursor can be moved to the visual axis position.

Figure 39:
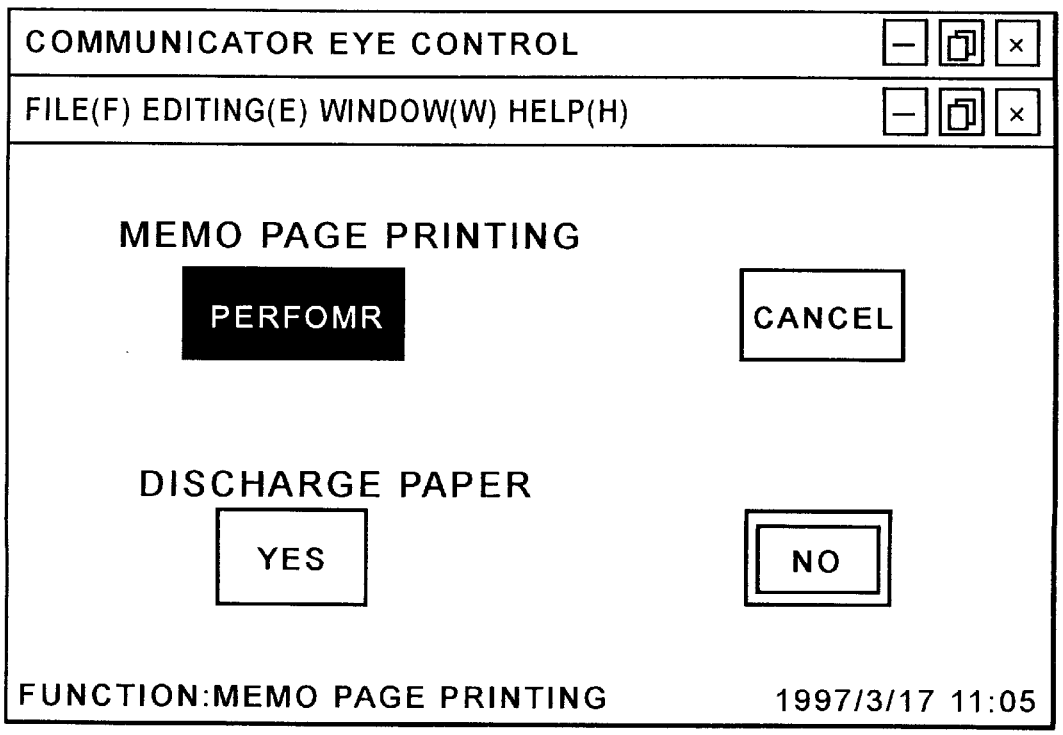
FIG. 39 is a diagram showing a screen for executing the printing of a created sentence.

An explanation will now be given for the "Memo page printing" function on the function selection screen 1. FIG. 39 is a diagram showing a screen for printing a sentence that has been created. Whether a sheet of paper will be discharged can be set by selecting "Yes" or "No" on this screen. This is effective when printing short sentences. When "No" is selected, paper need not be fully discharged from the printer each time printing occurs; only the portion that has been printed is fed out of the printer, and the paper discharge function of the printer is halted to permit a third party to read the printed portion. Since the next printing is initiated at the point the discharge of paper is halted, paper can be saved.

Figure 40:
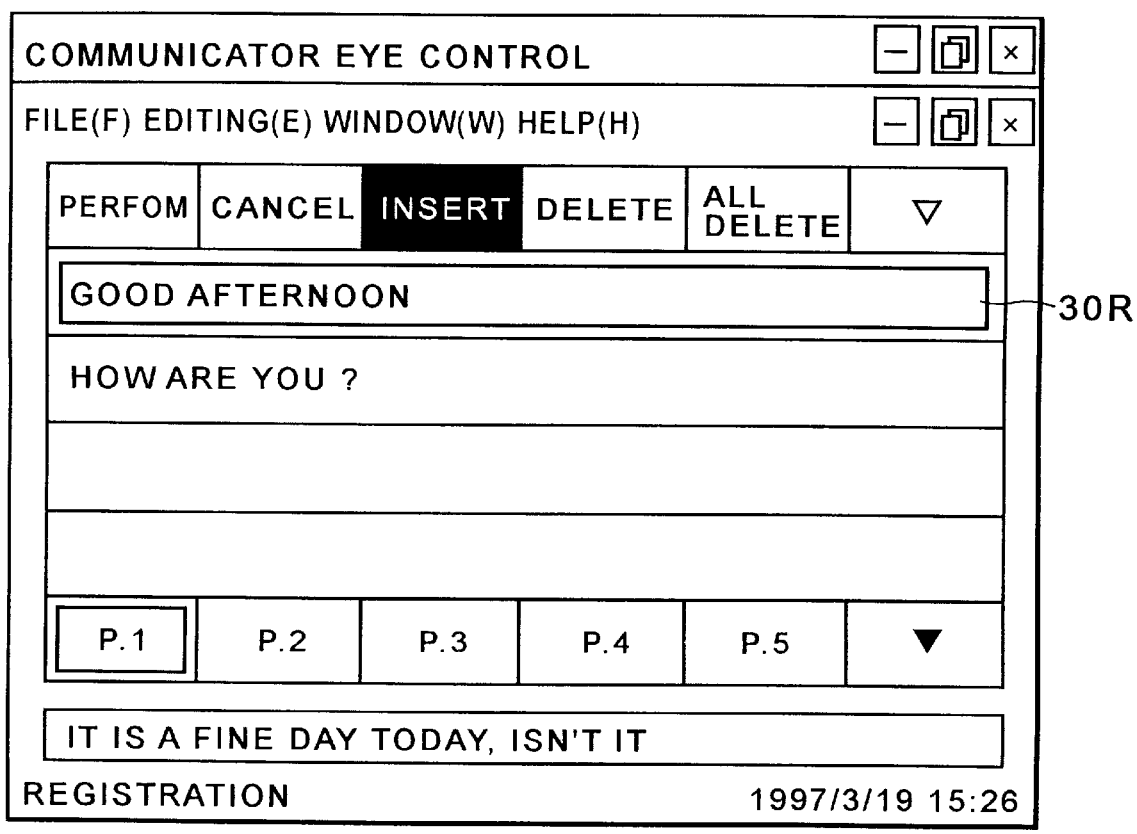
FIG. 40 is a diagram showing a registration screen for storing the created sentence in memory.

The "Registration" function on the character selection screen will now be described. FIG. 40 is a diagram showing a registration screen for storing in a memory a sentence that has been created. With this screen, the user can register and store at an arbitrary location a sentence created on the character selection screen. The registration screen is displayed by selecting "Registration" on the character selection screen. The topmost function keys are keys for registration options, and the second through the fifth rows are registered sentence display portions.

The page of a registered sentence is displayed in the bottom row of the display portion. A maximum of eight sentences can be registered for one registered sentence page. Since there are 10 registered sentence pages, a total of 80 sentences can be registered.

A sentence created on the character selection screen is displayed directly below the option display portion, and a description the effect on this sentence of the registration function keys in the topmost row will be given first.

"Perform": Confirms the results of "Insert", "Delete" or "Preceding character delete" performed in the registration mode, and terminates that mode.

"Cancel": Cancels all the results obtained by "Insert", "Delete" or "Preceding character delete" performed in the registration mode, and terminates that mode.

"Insert": Inserts a sentence created on the character selection screen into a registered sentence display location (the first row, enclosed by a red frame 30R in the registered sentence display portion in FIG. 40) and registers the sentence.

Figure 41:
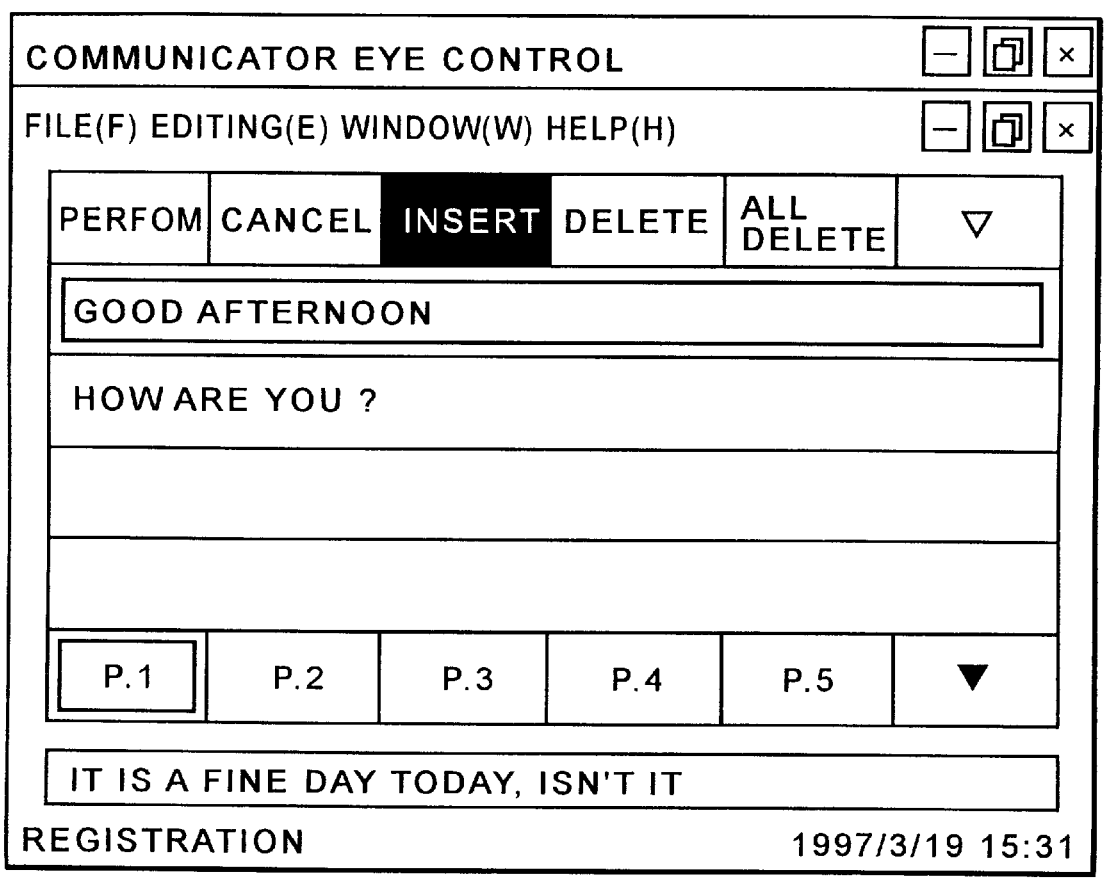
FIG. 41 is a diagram showing a screen for displaying the result of the registration of the sentence.

FIG. 41 is a diagram of the screen on which the results of sentence registration are shown. In this case, the sentences "Good afternoon" and "How are you?" are respectively moved from the first and the second rows in the registered sentence display portion to the second and the third rows, and a sentence "It is a fine day today, isn't it?", which was created on the character selection screen is registered and is inserted into the first row of the registered sentence display portion.

When the registration mode is terminated by the selection of "Cancel" in FIG. 41, the registration of the sentence that was inserted is nullified, and the screen is returned to the character selection screen.

Figure 42:
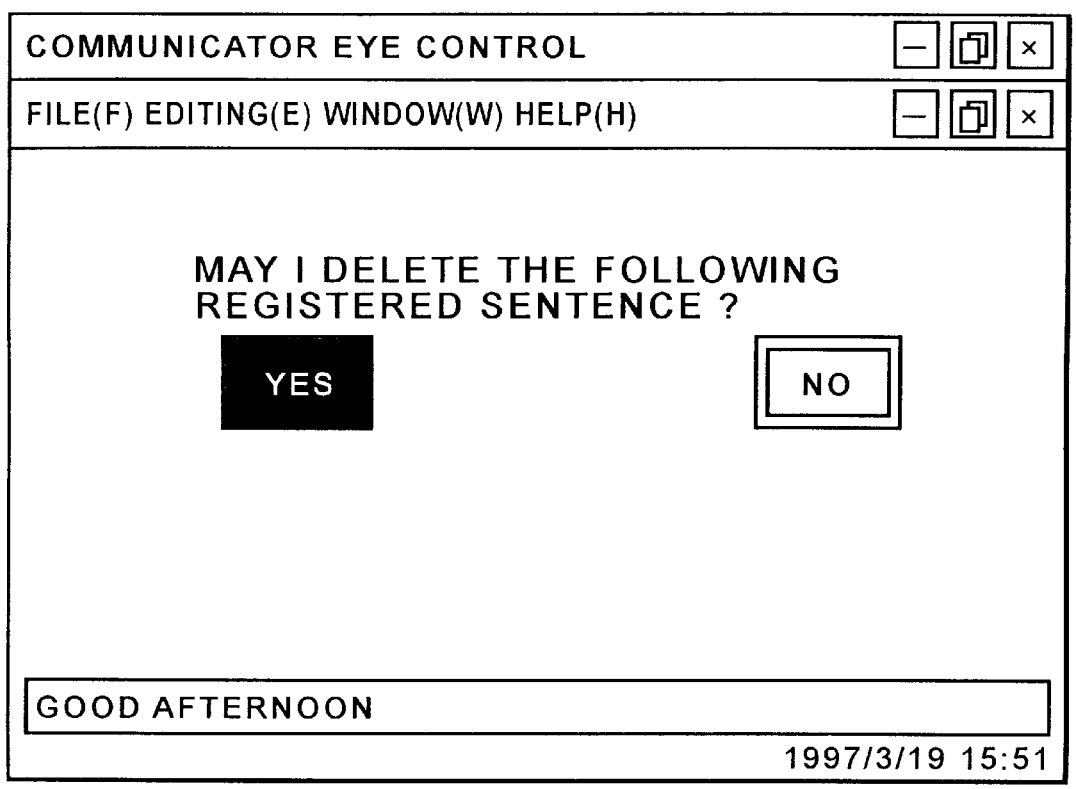
FIG. 42 is a diagram showing the screen for confirming the intent of a user when "delete" is entered.
Figure 43:
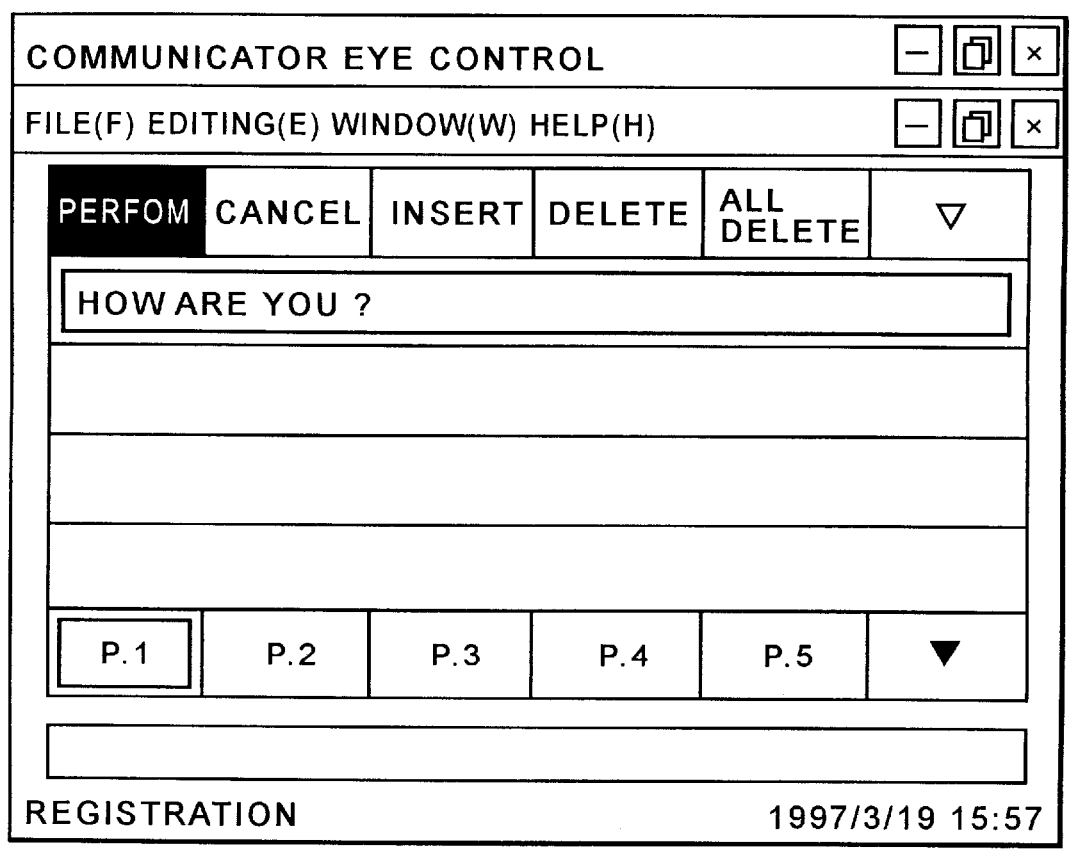
FIG. 43 is a diagram showing a screen for the result of a deletion.

"Delete": Deletes a sentence at a currently selected registered sentence display position (the first row, enclosed by the red frame 30R in the registered sentence display portion in FIG. 40). When "Delete" is entered, confirmation of the intent of the user is effected. FIG. 42 is a diagram showing a screen for confirming the intent of the user in response to the selection of "Delete". When "Yes" is selected, the entry is deleted. FIG. 43 is a diagram showing a screen for displaying the results of the deletion. It should, however, be noted, that when in FIG. 43 "Cancel" is entered in the registration mode, the deletion of the entry is not final, and the screen is returned to the character selection screen.

Figure 44:
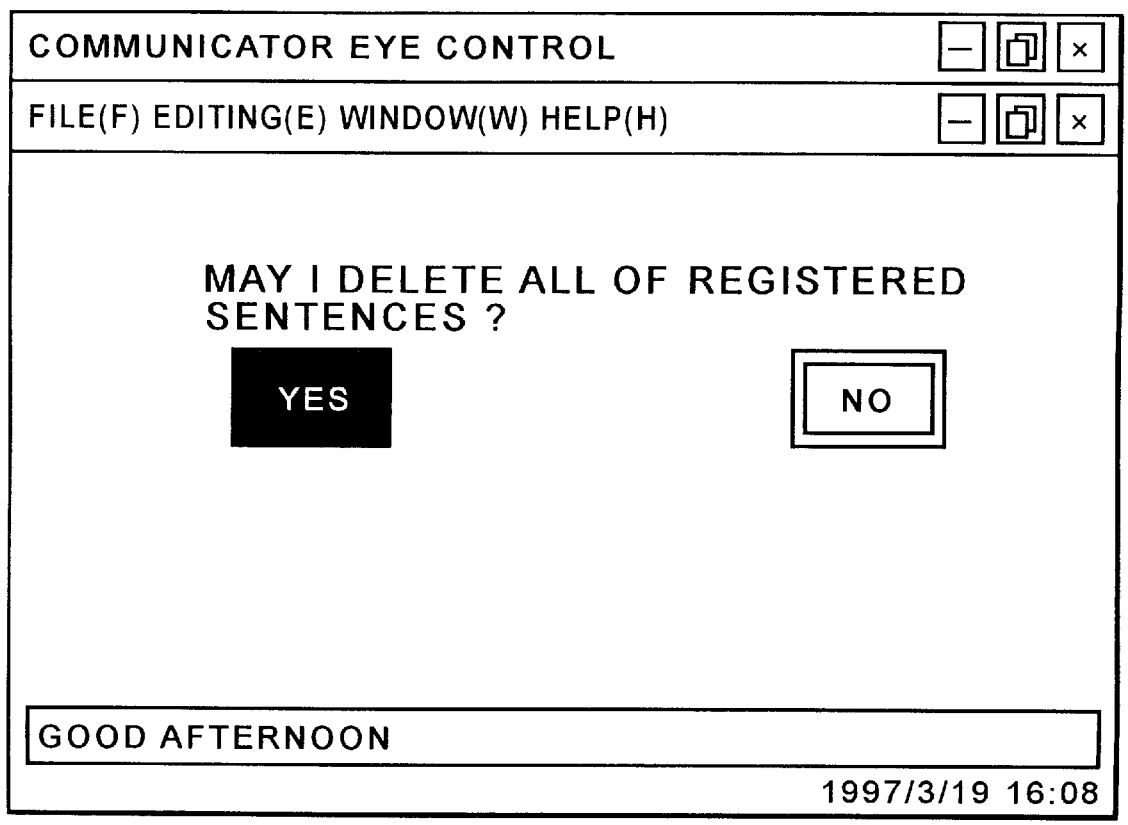
FIG. 44 is a diagram showing a screen for confirming the intent of a user when "delete all" is entered.

"All delete": Delete all the sentences that are currently registered. When "All delete" is entered, confirmation of the intent of the user is effected. FIG. 44 is a diagram showing a screen for confirming the intent of the user when "All delete" is entered.

When "Yes" is selected, all the entries are deleted. It should be noted, however, that when "Cancel" is entered in the registration mode, the deletion of all entries is not final, and the screen is returned to the character selection screen.

Figure 45:
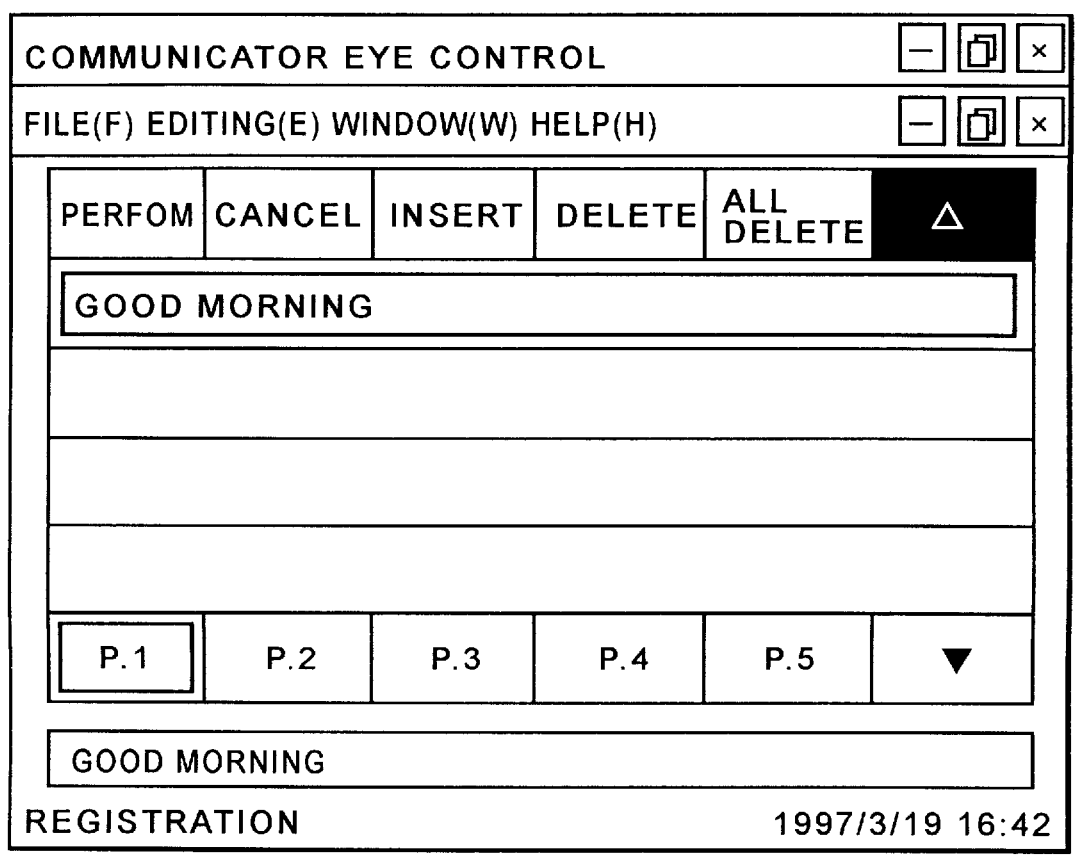
FIG. 45 is a diagram showing a screen on which "∇" is changed to "Δ"

"∇" ("Δ"): The first through the fourth sentences on the first registered sentence page are displayed in the registered sentence display portion in FIG. 40. When "∇" is selected, the fifth through the eighth sentences on the first registered sentence page are displayed in the registered sentence display portion. Also, the mark "∇" is changed to "Δ". FIG. 45 is a diagram showing a screen whereon the mark "∇" has been changed to "Δ". When "Δ" is selected, the sentences on the first registered sentence page that are displayed in the registered sentence display portion are changed from the fifth through the eighth sentences to the first through the fourth registered sentences.

Figure 46:
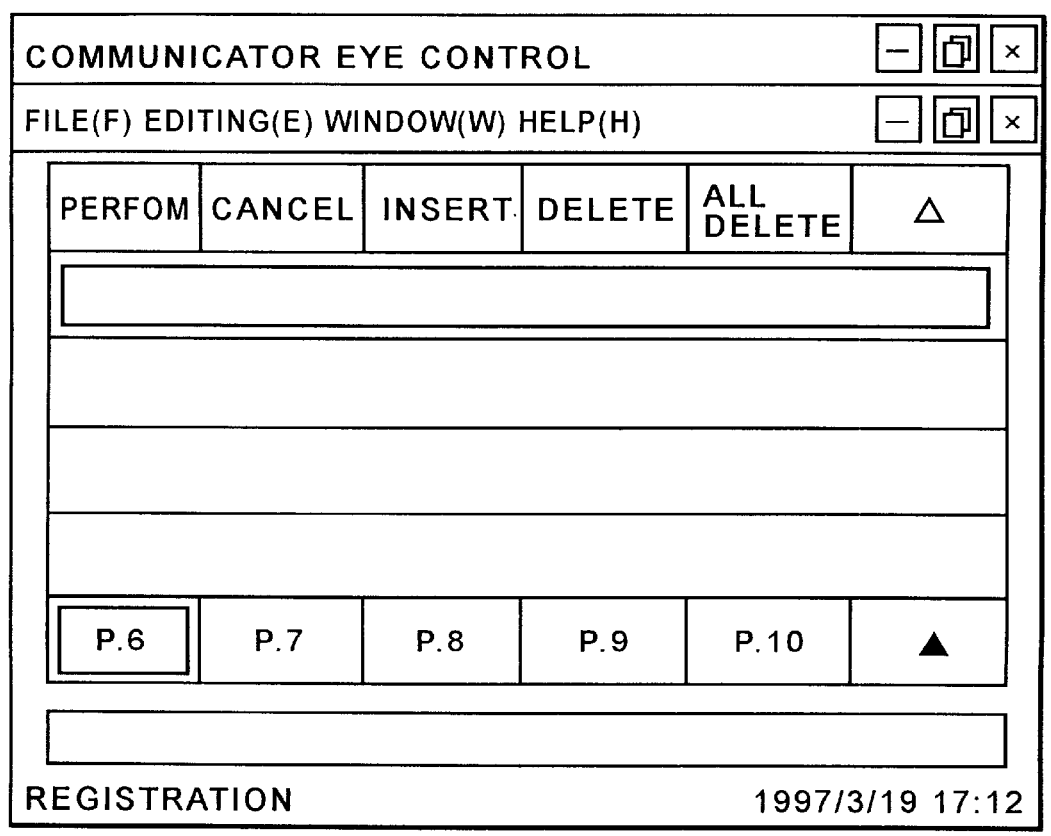
FIG. 46 is a diagram showing a screen on which "▼" is changed to "▲"

Now, the registered sentence page display portion at the bottom will be described. "P.1" to "P.5" corresponds to the registered sentence pages 1 to 5. When one of the "P.1" to "P.5" options is designated, registered sentences on the corresponding page are displayed in the registered sentence display portion. When "▼" is entered, "P.6" to "P.10" (the registered sentence pages 6 to 10) are displayed in the registered sentence display portion, and the registered sentence pages 6 to 10 can be selected. In addition, the mark "▼" is changed to "▲". FIG. 46 is a diagram showing a screen wherein the "▼" has been changed to "▲".

The registered sentences are managed in a TXT file when the application is not in use, and are managed in a registered sentence control arrangement when the application is in use. The registered sentence control arrangement is two-dimensional, with the first element number being represented using the registered sentence page, and the second element number indicating the position among the ten sentences on each registered sentence page.

Figure 47:
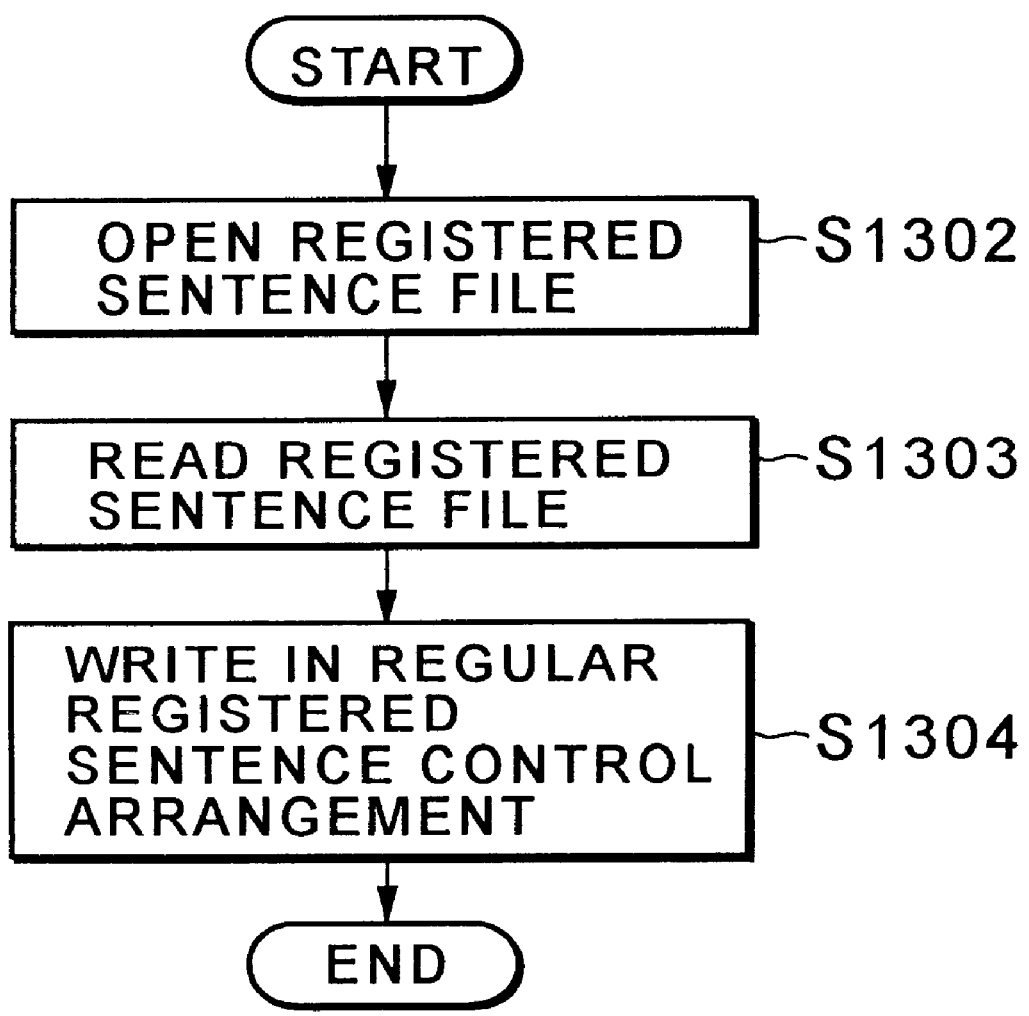
FIG. 47 is a flowchart showing the processing for reading a TXT file to which a registered sentence was written when an application was activated.

FIG. 47 is a flowchart showing the reading processing, when the application is activated, for a TXT file in which registered sentences are written. First, a file in which registered sentences are written is opened (step S1302). Then, all the registered sentences are read, as a single sentence string, from the file in which they are written (step S1303). FIG. 48 is a diagram showing the string in a file where the registered sentences are written. A registered sentence string is divided using a return code (¥n), and from the beginning, the separate sentences are written, in order, into the registered sentence control arrangement (step S1304).

Figure 49:
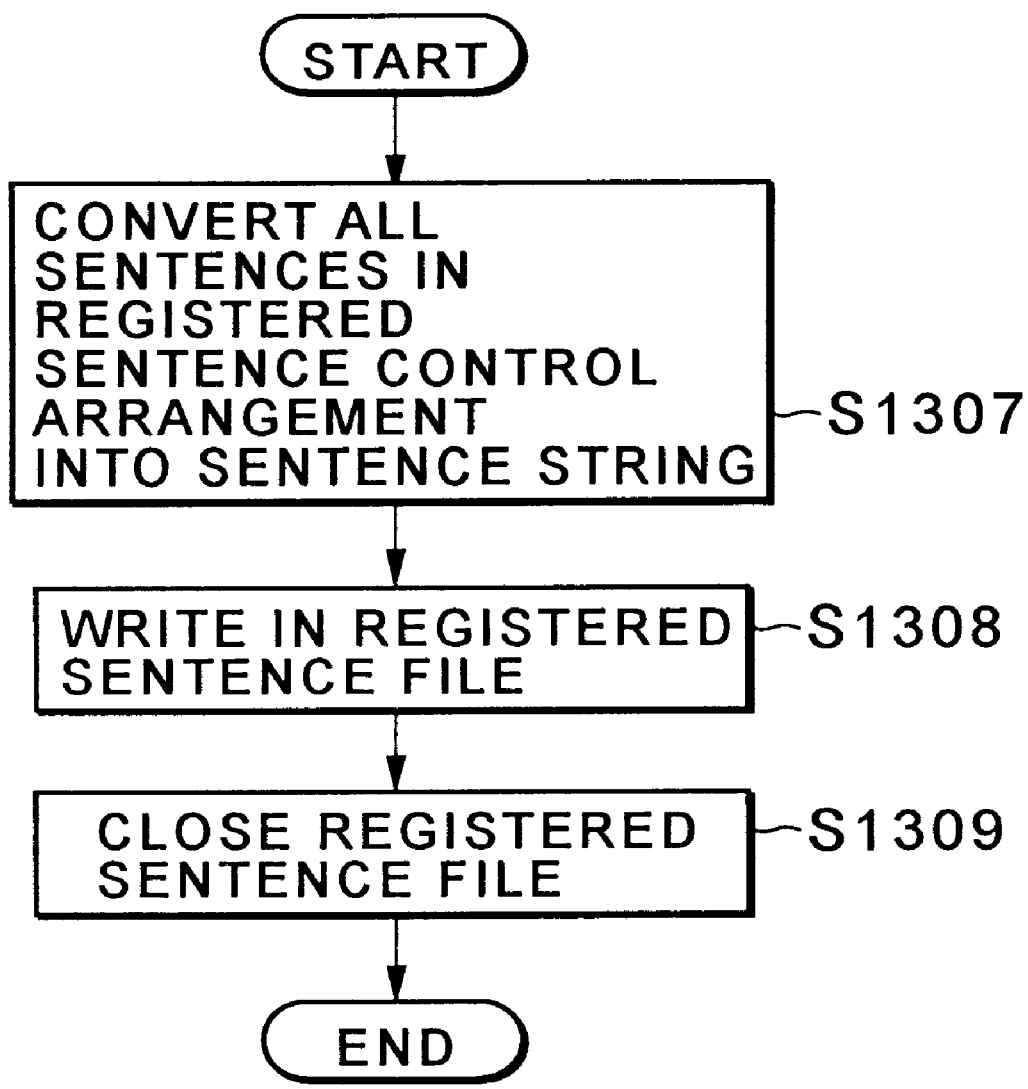
FIG. 49 is a flowchart showing the processing for writing a registered sentence to a file when an application is terminated.

FIG. 49 is a flowchart showing the processing for writing a registered sentence to a TXT file when an application is terminated. All the sentences in the registered sentence control arrangement are converted into a sentence string (step S1307). Then the obtained sentence string (see FIG. 48) is written into the registered sentence TXT file (step S1308). The TXT file is then closed (step S1309).

Figure 50:
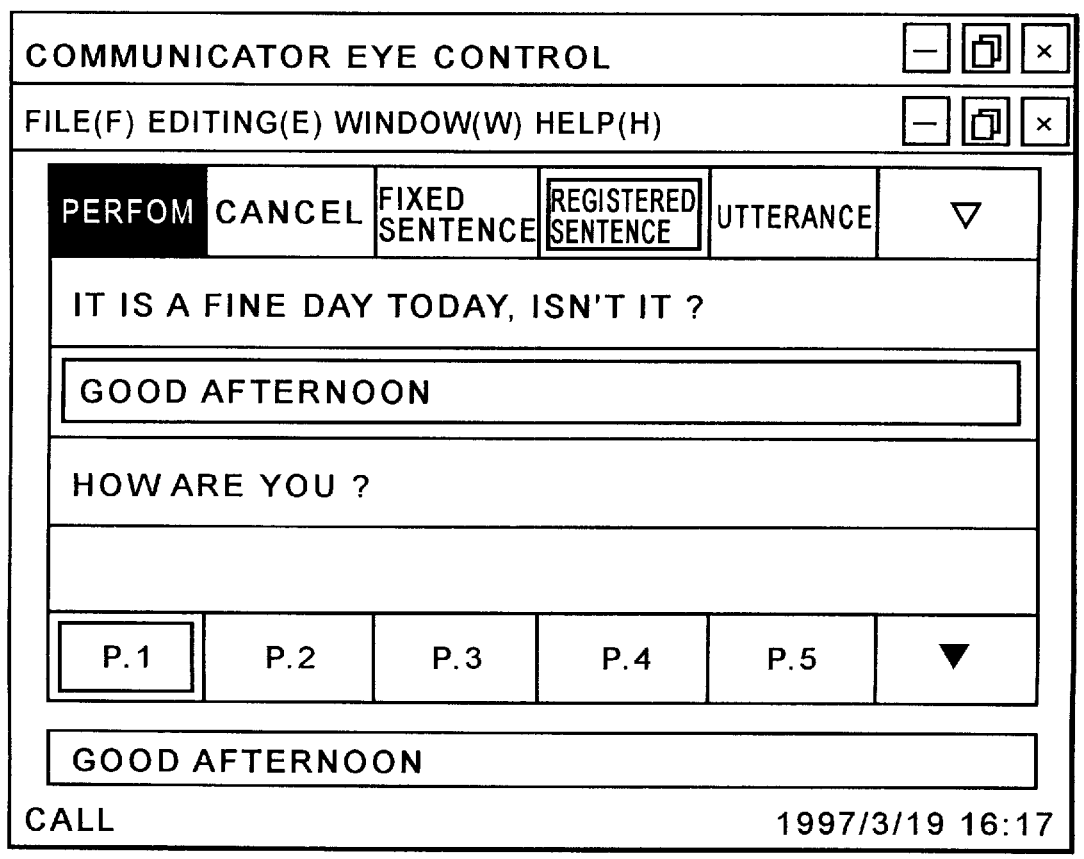
FIG. 50 is a diagram showing a retrieval screen for retrieving a registered sentence and displaying it in the created sentence display portion of the character selection screen.

The "Call" function on the character selection screen will now be described. FIG. 50 is a diagram showing a call screen for retrieving registered sentences and inserting them into the sentence display portion on the character selection screen. With this function, the user can retrieve a registered sentence and insert it into a desired position in the sentence display portion on the character selection screen.

The call screen is displayed by selecting "Call" on the character selection screen. In the topmost row are displayed function keys relative to call, and the second to the fifth rows are a called sentence display portion. The bottommost row displays the page of the called sentences.

Two types of sentences are called: a registered sentence that is created by the user and is registered in the registration mode, and a common fixed sentence that is employed daily and is supplied as part of in the application. A total of 80 fixed sentences are prepared for 10 pages in addition to the previously mentioned registered sentences. A sentence when selected and called is displayed below the option display portion.

First, the function keys in the topmost row concerning the call will be explained.

"Perform": Calls and inserts a selected sentence into the sentence that is created on the character selection screen, and then terminates the call mode. The sentence is inserted at the cursor's position in the sentence display portion on the character selection screen. FIG. 51 is a diagram showing a screen reflecting the result of a call. In the created sentence, "Good afternoon" has been called.

"Cancel": Cancels a call and the insertion of a selected sentence into a sentence that has been created on the character selection screen, and then terminates the call mode.

"Fixed sentence": Enables the selection of a common fixed sentence that is employed daily and is provided with the application. When "Fixed sentence" is selected, a fixed sentence is displayed in the called sentence display portion, and the fixed sentence pages are displayed in the called sentence page display portion. FIG. 52 is a table showing the fixed sentences and the names of the fixed sentence pages.

"Registered sentence": Enables the selection of a sentence that has been created by the user and has been registered in the registration mode. When "Registered sentence" is selected, a registered sentence is displayed in the called sentenced display portion, and the registered sentence pages ("P.1" to "P.10") are displayed in the called sentence page display portion.

"Utterance": Utters a currently selected sentence. The user can hold a conversation by repeating the selection and the utterance of a called sentence in the call mode, without each time retrieving the sentence into the sentence display portion on the character selection screen.

Figure 53:
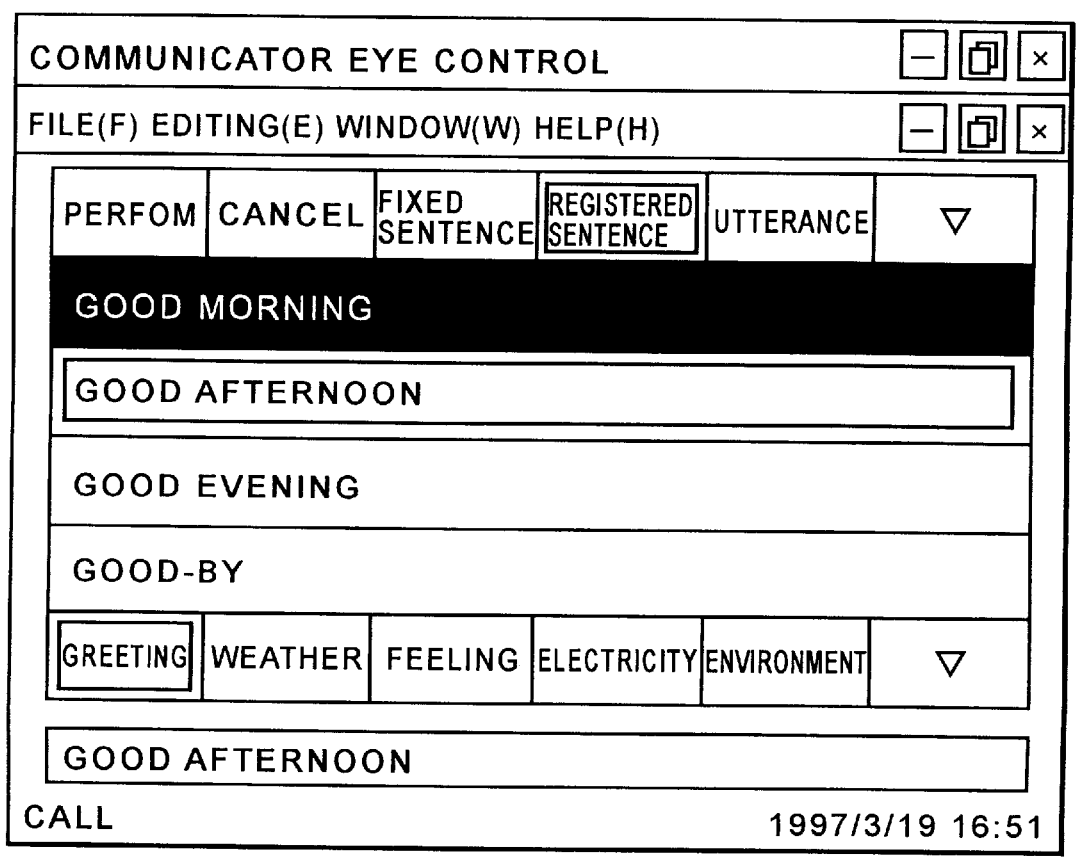
FIG. 53 is a diagram showing a screen whereon the first fixed sentence to the fourth fixed sentence on the first page are displayed in a retrieved sentence display portion.

"▽" ("△"): FIG. 53 is a diagram showing a screen wherein the first through the fourth sentences on the first fixed sentence page are displayed in the called sentence display portion. When "▽" is selected, the fifth to the eighth sentences on the first fixed sentence page are displayed in the called sentence display portion.

Figure 54:
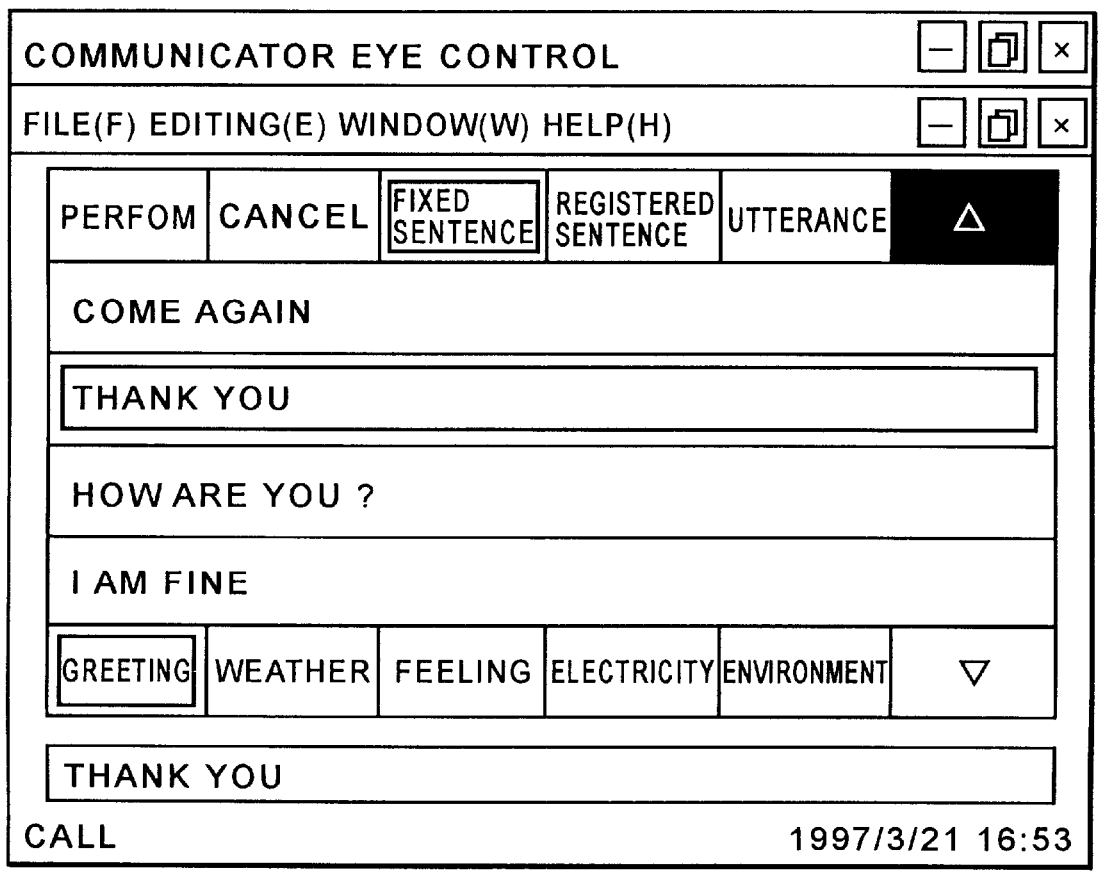
FIG. 54 is a diagram showing a screen on which "∇" is changed to "Δ"

Also, the mark "▽"is changed to "△". FIG. 54 is a diagram showing a screen wherein the mark "▽" has been is changed to "△". When "△" is selected, the sentences displayed in the called sentence display portion for the first fixed sentence page are changed from the fifth through the eighth sentences to the first through the fourth.

Following this, the called sentence page display portion at the lowermost row will be explained. The processing for this is the same as that for the registered sentence pages. When a fixed sentence is called, the fixed sentence pages are displayed in the called sentence display portion, and the names of the fixed sentence pages are as shown in FIG. 52. When a registered sentence is called, the registered sentence pages are displayed in the called sentence page display portion, and the names of the registered sentence pages that are displayed are "P.1" to "P.10," as was previously described.

The "Change input confirmation method" function on the function selection screen 2 may switch the method for establishing an entry when the visual axis position is held on the same option for a predetermined period of time or longer, the method for establishing an entry for which a user looks at the same choice and then closes the eyes for a predetermined period of time, and the method for establishing an entry for which a user stares at the same character and then depresses a switch for a predetermined period of time.

According to the first to the tenth embodiments, a user can select an option by moving his, or her, eyes. Therefore, it is easy for a seriously physically handicapped person who can not depress a foot button to establish which character is to be input.

In addition, even when the position of the user's head is changed, the user can correctly enter a choice by moving his, or her, eyes.

Furthermore, since the display panel video is projected on a screen, imposing an excessive load on the eyes when selecting an option can be prevented.

Further, since the display panel video is projected on the screen, the load applied on the eyes when selecting an option can be reduced, and a user can select a correct option choice by moving his, or her, eyes even when the position of the head is changed.

Moreover, a user can enter a character simply by viewing the video.

Furthermore, since a user can select an option by closing his, or her, eyes, the load imposed on the eyes can be reduced, compared with when to select an option the position of the visual axis is sustained for a specific period of time.

And then, a user can select an option by moving his, or her, eyes, and using a slight body movement to confirm the selection.

Since a user can select an input determination method option that is suitable for his, or her, physical condition, useability can be improved.

And usability is further enhanced because a user can adjust the time required to verify the selection of an option and select one that is suitable for his, or her, condition.

As is described above, according to the first to the tenth embodiments, provided is a visual axis entry transmission apparatus that provides on a computer screen a display panel consisting of a plurality of characters, such as hiragana or alphabetical characters, detects the visual axis of a user who is viewing the display panel, employs the result of the detection of the visual axis of the user to identify a character the user selects, and accepts the identified character. In addition, provided are a visual axis entry transmission apparatus that can switch television channels, and a visual axis entry transmission apparatus with which the user, while monitoring a computer screen, can exchange a display panel video image displayed on the computer screen for one that is input to the computer.

According to the first to the tenth embodiment, for the visual axis entry transmission apparatus, a method is employed for verifying a selected character whereby a user by looking at the character and closing his, or her, eyes. This method, closing one's eyes, for verifying an entry is also employed when instructing a television channel change.

However, with the above visual axis entry transmission apparatus that employs the method whereby the eyes are closed to verify the selection of an option, when the eyes are closed too early, a selection will not be verified. Thus, training for a user must be provided until he, or she, has acquired the sense of timing required for the closing of the eyes. In addition, since the apparatus does not include means for notifying a user of the frequent occurrences of visual axis detection errors, such as input errors that are caused by the eyes being closed too early or visual axis detection failures that occur when the eyes of a user are incorrectly captured, when such detection errors occur there is no means by which a user can be notified. As a result, a user who is unaware of the operating conditions may input a useless operation. And, as is described above, when a user does not know whether or not the detection of the visual axis has been successful and thus inputs a useless operation, since the user can not be notified that the entry using the visual axis was unsuccessful, he, or she, may repeat the operation many times.

When there are many options available on the display panel, the display areas for the options are reduced and it is difficult to select a desired choice.

A visual axis entry transmission apparatus that resolves the above shortcomings will now be described according to an eleventh through a twenty-first embodiment of the present invention.

(k) Eleventh Embodiment

According to an eleventh embodiment of the present invention, the personal computer 1008 in FIG. 5 performs a video display process, for supplying video data to be viewed by a user to the liquid crystal display circuit 1007 in the head-mounted display unit 1006, and an option input process, for acquiring through the accessory device controller 1815 focusing point data that are obtained by the visual axis detection circuit 1064 of the head-mounted display unit 1006; and for employing the focusing point data to identify and enter an option that is selected from among those displayed in the video image on the liquid crystal display device 1002. In addition, a detection result notification process for the operating condition can be performed whereby focusing point data are employed to determine whether or not the detection of the visual axis was successful, whether the user's eyes are blinking, or whether the same choice has been selected; and whereby, in accordance with the result obtained by the determination, information concerning the detected condition can be provided to the user. Whether or not this detection result notification process is selected by the user, in this embodiment the user is provided detection result information by changing the selection frame colors for options displayed in the video image that the user is viewing.

These processes are initiated when a program for building a visual axis entry transmission system is read from a memory medium, such as a hard disk (not shown), and is executed by CPU 1814.

Figure 55:
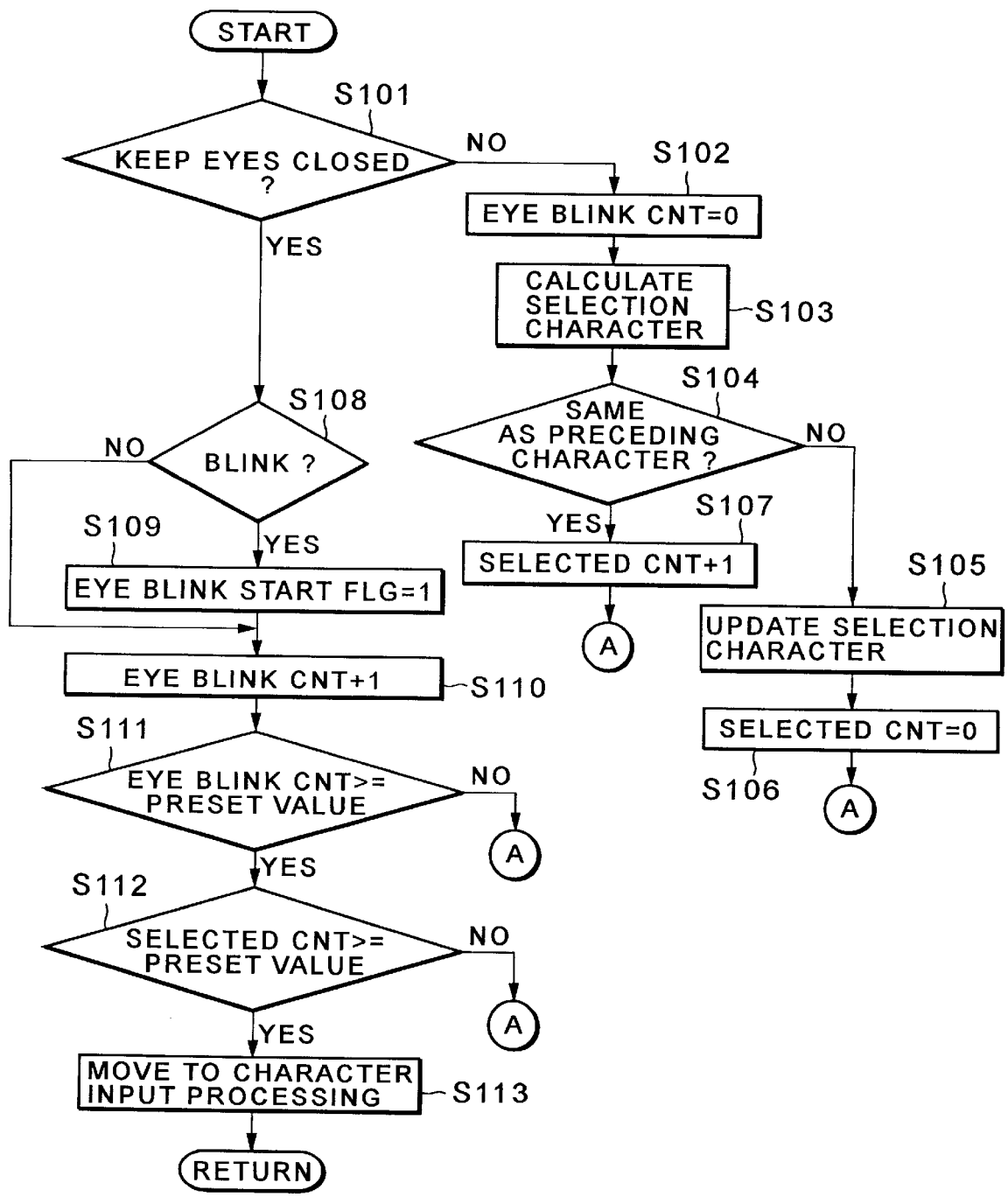
FIG. 55 is a flowchart showing visual axis detection result information notification processing performed by the visual axis entry transmission apparatus in FIG. 3 according to an eleventh embodiment of the present invention.
Figure 56:
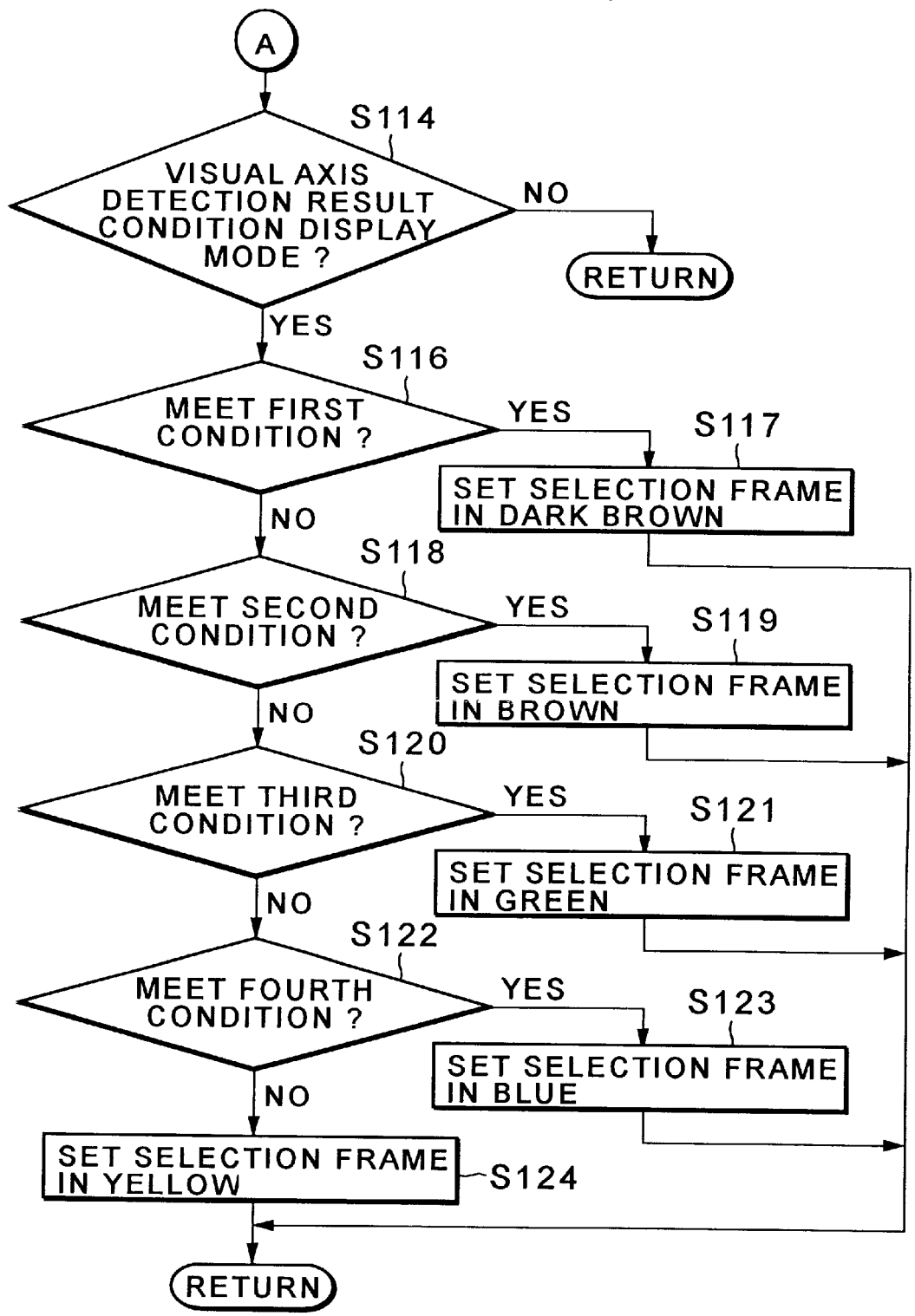
FIG. 56 is a flowchart showing the visual axis detection result information notification processing performed by the visual axis entry transmission apparatus in FIG. 3 according to the eleventh embodiment of the present invention.

An explanation will now be given for the visual detection result information notification processing according to the eleventh embodiment while referring to FIGS. 55 and 56. FIGS. 55 and 56 are flowcharts showing the visual axis detection result information notification processing performed by the visual axis entry transmission apparatus in FIG. 3.

In FIG. 55, first, at step S101 visual axis position data that are obtained by the visual axis detection circuit 1064 of the head-mounted display unit 1006 are employed to determine whether the user's eyes were kept closed. When the user's eyes were not closed, program control moves to step S102, whereat counter EyeBlinkCnt for measuring the time period during which the user's eyes were closed is reset. And then, at step S103, a character at the visual axis position is acquired as a selected character based on the visual axis position data that were obtained by the visual axis detection circuit 1064. Following this, at step S104, a check is performed to determine whether the currently selected character is the same as a preceding character that was selected. When the two characters are the same, program control moves to step S107, whereat the value at counter SelectedCnt, which is an up-counter, is incremented by one. Program control then goes to step S114 in FIG. 56. If the currently selected character is not the same as the previously selected character, program control moves to step S105, whereat data for the selected character are updated to those for the currently selected character. Then, at step S106, the counter SelectedCnt is reset, and program control goes to step S114.

When at step S101 the user's eyes were kept closed, at step S108 whether or not the closing of the eyes was a blink is determined, based on whether detection data that indicate blinking were received from the visual axis detection circuit 1064. If the closing of the eyes was a blink, at step S109 flag EyeBlinkStartFlg is set to "1", and program control advances to step S110. When at step S108 the closing of the eyes was not a blink, program control skips step S109 and goes to step S110, whereat the value at the counter EyeBlinkCnt for measuring the time the eyes are closed is incremented by one. Sequentially, at step S111, a check is performed to determine whether the count value of the counter EyeBlinkCnt is equal to or greater than a preset value. When the count value of the counter EyeBlinkCnt is not equal to or greater than the preset value, program control goes to step S114 in FIG. 56.

When the count value of the counter EyeBlinkCnt is equal to or greater than the preset value, at step S112 a check is performed to determine whether the count value of the counter SelectedCnt is equal to or greater than a preset value. The preset value for the counter SelectedCnt differs from that for the counter EyeBlinkCnt. When the count value of the counter SelectedCnt is not equal to or greater than the preset value, program control moves to step S114 in FIG. 56. When the count value of the counter SelectedCnt is equal to or greater than the preset value, it is assumed that the values of the counter EyeBlinkCnt and the counter SelectedCnt satisfy the corresponding preset values and that a character input condition has been established. Program control then moves to step S113, whereat the processing is advanced to the character input processing.

After the process at step S106 or S107, or upon receiving a negative response at step S111 or S112, program control goes to step S114. At step S114, as is shown in FIG. 56, a check is performed to determine whether the visual axis detection result condition display mode has been set. When the visual axis detection result condition display mode has not been set, program control exits this processing sequence. When the visual axis detection result condition display mode has been set, at step S116 a check is performed to determine whether the count value of the counter EyeBlinkCnt and the value of the flag EyeBlinkStartFlg satisfy the values that are specified under the first condition. When the values satisfy the first condition, this means that it has been established that the count value of the counter EyeBlinkcnt≧1 and that the value of the flag EyeBlinkStartFlg=0. When the first condition is satisfied, i.e., when the count value of the counter EyeBlinkCnt is equal to or greater than "1" and the value of the flag EyeBlinkStartFlg is "0", it is assumed that the user's eyes were closed and no blink was detected. Then, at step S117, the color of a selection frame for the corresponding option in the video image on the liquid crystal display device 1002 that the user is viewing is changed to a color indicating that the eyes were closed and that no blinking was detected. Program control thereafter exits this processing sequence. In this embodiment, dark brown is used to indicate that no blinking was detected.

When the first condition is not satisfied, at step S118 a check is performed to determine whether the count value of the counter EyeBlinkCnt, the value of the flag EyeBlinkStartFlg and the count value of the counter SelectedCnt satisfy the values that are specified under the second condition. When the values satisfy the second condition, this means that it has been established that the count value of the counter EyeBlinkCnt≧1, that the value of the flag EyeBlinkStartFlg=1, and that the count value of the counter SelectedCnt<the preset value. When the second condition is satisfied, i.e., when the count value of the counter EyeBlinkCnt is equal to or greater than "1" and the value of the flag EyeBlinkStartFlg is "1", it is assumed that the entry of the selected character has not yet been established because the count value of the counter SelectedCnt did not equal the preset value while blinking to specify the selected character was detected. Then, at step S119, the color of a selection frame for the corresponding option in the video image on the liquid crystal display device 1002 that the user is viewing is changed to a color indicating that the entry of a selected character has not yet been established. Program control thereafter exits this processing sequence. In this embodiment, brown is the color used to indicate that the entry of a selected character has not been established.

When the second condition is not satisfied, at step S120 a check is performed to determine whether the count value of the counter EyeBlinkCnt, the value of the flag EyeBlinkStartFlg and the count value of the counter SelectedCnt satisfy the values that are specified under the third condition. When the values satisfy the third condition, this means it has been established that the count value of the counter EyeBlinkCnt≧1, that the value of the flag EyeBlinkStartFlg=1, and that the count value of the counter SelectedCnt≧the preset value. When the third condition is satisfied, i.e., when the count value of the counter SelectedCnt equals the preset value, it is assumed that the selection of the character was established by the eyes being kept closed for a predetermined period of time because, while the selected character was confirmed, the count value of the counter EyeBlinkCnt was equal to or greater than "1" and the value of the flag EyeBlinkStartFlg was "1". Then, at step S121 the color of a selection frame for the corresponding choice in the video image on the liquid crystal display device 1002 that the user is viewing is changed to a color indicating that the entry of a selected character was effected by the eyes being kept closed for a predetermined period of time. Program control thereafter exits this processing sequence. In this embodiment, green is used to indicate that the entry of a selected character was effected by the eyes being closed for a predetermined period of time.

When the third condition is not satisfied, at step S122 a check is performed to determine whether the count value of the counter SelectedCnt satisfies the value that is specified under the fourth condition. When the count value satisfies the fourth condition, this means that it has been established that the count value of the counter SelectedCnt≧the preset value. When the fourth condition is satisfied, i.e., when the count value of the counter SelectedCnt has equaled the preset value, it is assumed that the user's eyes were not closed because, although the selected character has been confirmed, the current condition does not correspond to the first through the third conditions. Then, at step S123 the color of a selection frame for the corresponding option in the video image on the liquid crystal display device 1002 that the user is viewing is changed to a color indicating that a character has been confirmed. Program control thereafter exits this processing sequence. In this embodiment, blue is used to indicate that a character has been confirmed.

When the fourth condition is not satisfied, i.e., when the condition does not correspond to the first to the fourth condition, it is assumed that the user's eyes are open and a character has not yet been selected because it has been established that the count value of the counter SelectedCnt<the preset value. Then, at step S124, the color of a selection frame for the corresponding option in the video image on the liquid crystal display device 1002 that the user is viewing is changed to a color indicating that no character has been selected. Program control thereafter exits this processing. In this embodiment, yellow is used to indicate that no character has been selected.

As is described above, in this embodiment the user is provided detection result information by changing the color of the selection frame for a selectable character in the video image that the user is viewing. Therefore, the user can confirm the result of the detection of the visual axis, and the possibility that the user will repeat a useless operation can be eliminated.

In this embodiment, the user is provided detection result information by changing the color of the selection frame for a selectable character in the video image that the user is viewing; however, the color of a selected character or the background of a selected character may also be changed to provide detection result information for the user. In addition, in this embodiment the selection of characters is employed, but the same system that is used to provide a user the visual axis detection result can be employed to make a selection consisting of a figure other than a character.

(l) Twelfth Embodiment

Figure 57:
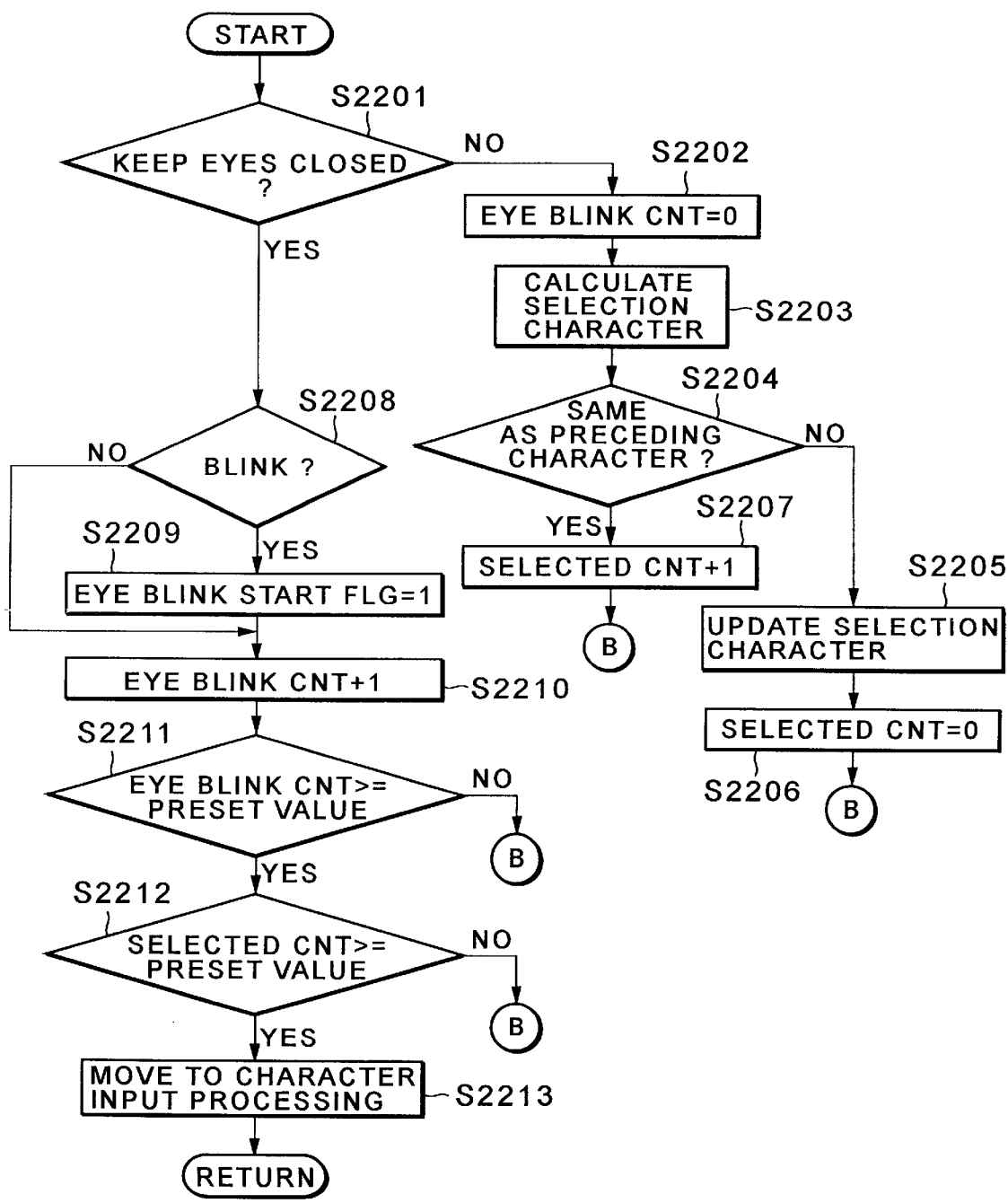
FIG. 57 is a flowchart showing visual axis detection result information notification processing performed by the visual axis entry transmission apparatus according to a twelfth embodiment of the present invention.
Figure 58:
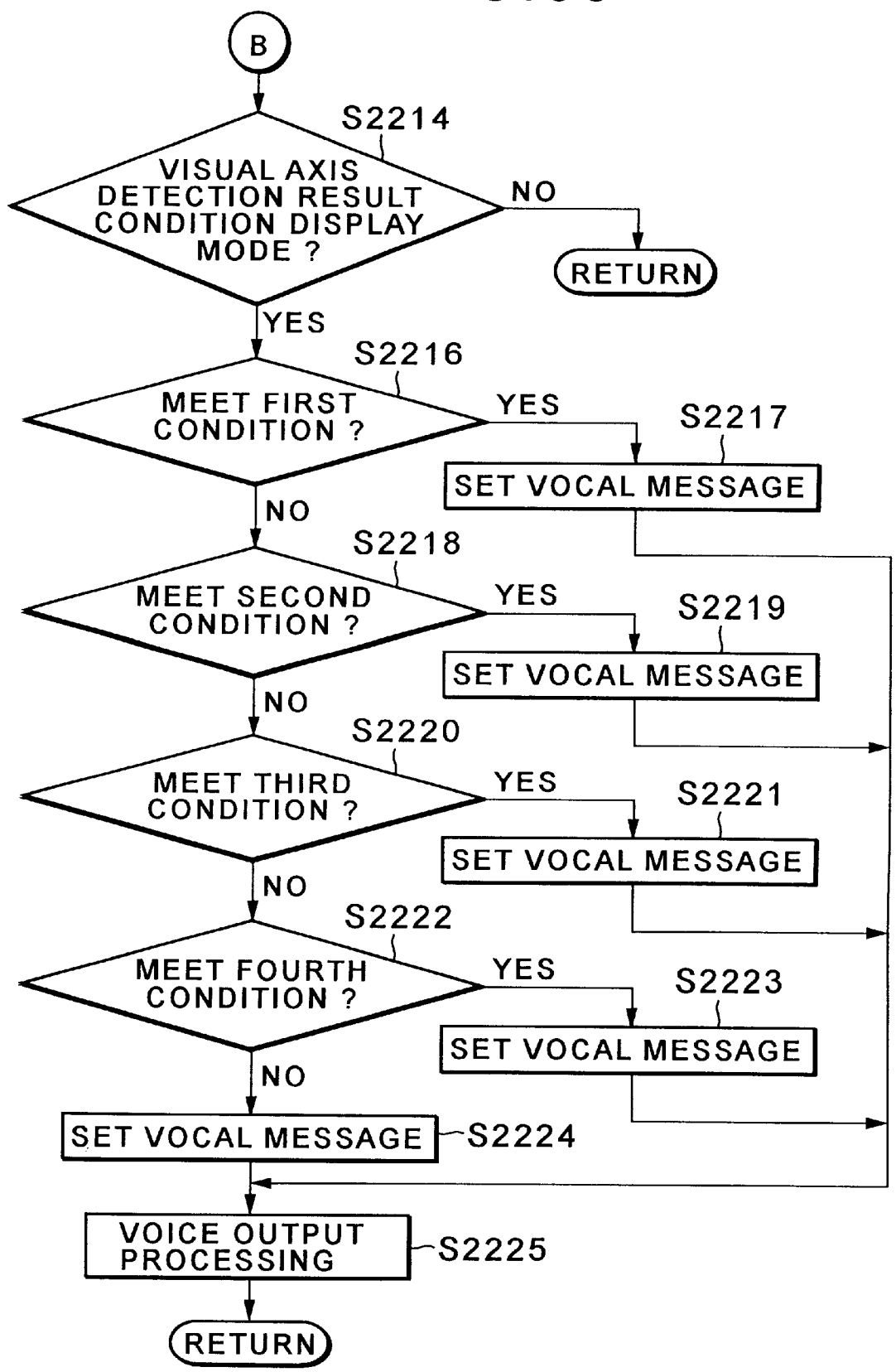
FIG. 58 is a flowchart showing the visual axis detection result information notification processing performed by the visual axis entry transmission apparatus according to the twelfth embodiment of the present invention.

An explanation will now be given for the visual axis detection result information notification processing according to a twelfth embodiment while referring to FIGS. 57 and 58. FIGS. 57 and 58 are flowcharts showing the visual axis detection result information notification processing performed by the visual axis entry transmission apparatus according to the twelfth embodiment.

The arrangement for this embodiment is the same as that for the eleventh embodiment, except that a user is notified of detection result information by receiving an audio message that is generated through a loudspeaker incorporated in a personal computer 1008. Therefore, no explanation for the arrangement will be given.

The visual axis detection result information notification processing will now be described while referring to FIGS. 57 and 58.

In FIG. 57, first at step S2201 visual axis position data that are obtained by the visual axis detection circuit 1064 of the head-mounted display unit 1006 are employed to determine whether the user keeps the eyes closed. When the user does not close the eyes, program control moves to step S2202, whereat counter EyeBlinkCnt is reset. And at step S2203 a character at the visual axis position is obtained as a selected character based on the visual axis position data that are obtained by the visual axis detection circuit 1064. Following this, at step S2204, a check is performed to determine whether the currently selected character is the same as a preceding character that was selected. When the two characters are the same, program control moves to step S2207, whereat the value at counter SelectedCnt is incremented by one. Program control then goes to step S2214 in FIG. 58. If the currently selected character is not the same as the previously selected character, program control moves to step S2205, whereat data for the selected character are updated to those for the currently selected character. Then, at step S2206 the counter SelectedCnt is reset, and program control goes to step S2214.

When at step S2201 the user keeps the eyes closed, at step S2208 whether the closing of the eyes is a blink is determined depending on whether detection data that indicate blinking are received from the visual axis detection circuit 1064. If the closing of the eyes is a blink, at step S2209 flag EyeBlinkStartFlg is set to "1", and program control advances to step S2210. When at step S2208 the closing of the eyes is not a blink, program control skips step S2209 and goes to step S2210, whereat the value at the counter EyeBlinkCnt is incremented by one. Sequentially, at step S2211 a check is performed to determine whether the count value of the counter EyeBlinkCnt is equal to or greater than a preset value. When the count value of the counter EyeBlinkCnt is not equal to or greater than the preset value, program control goes to step S2214 in FIG. 58.

When the count value of the counter EyeBlinkCnt is equal to or greater than the preset value, at step S2212 a check is performed to determine the count value of the counter SelectedCnt is equal to or greater than a preset value. The preset value for the counter SelectedCnt differs from that for the counter EyeBlinkCnt. When the count value of the counter SelectedCnt is not equal to or greater than the preset value, program control moves to step S2214 in FIG. 58. When the count value of the counter SelectedCnt is equal to or greater than the preset value, it is assumed that the values of the counter EyeBlinkCnt and the counter SelectedCnt satisfy the corresponding preset values and that the character input condition is established. Program control then moves to step S2213, whereat the processing is moved to the character input processing.

After the process at step S2206 or S2207, or upon receipt of a negative response at step S2211 or S2212, program control goes to step S2214. At step S2214, as is shown in FIG. 58, a check is performed to determine whether the visual axis detection result condition display mode is set. When the visual axis detection result condition display mode is not set, program control exits from this processing sequence. When the visual axis detection result condition display mode is set, at step S2216 a check is performed to determine whether the count value of the counter EyeBlinkCnt and the value of the flag EyeBlinkStartFlg satisfy the values that are specified under the first condition. When the values satisfy the first condition, this means that the count value of the counter EyeBlinkCnt≧1 and the value of the flag EyeBlinkStartFlg=0 are established. When the first condition is satisfied, i.e., when the count value of the counter EyeBlinkCnt is equal to or greater than "1" and the value of the flag EyeBlinkStartFlg is "0", it is assumed that the eyes are closed and no blinks are detected. Then, at step S2217 a vocal message indicating that no blinking was detected while the user's eyes were closed is stored in a vocal output memory. Then, at step S2225, a vocal output process is performed to release the vocal message stored in the vocal output memory. Program control thereafter exists this processing sequence.

When the first condition is not satisfied, at step S2218 a check is performed to determine whether the count value of the counter EyeBlinkCnt, the value of the flag EyeBlinkStartFlg and the count value of the counter SelectedCnt satisfy the values that are specified under the second condition. When the values satisfy the second condition, this means that the count value of the counter EyeBlinkCnt≧1, the value of the flag EyeBlinkStartFlg=1 and the count value of the counter SelectedCnt<the preset value are established. When the second condition is satisfied, i.e., when the count value of the counter EyeBlinkCnt is equal to or greater than "1" and the value of the flag EyeBlinkStartFlg is "1", it is assumed that the entry of the selected character is not yet established because the count value of the counter SelectedCnt does not reach the preset value while the blinks are detected to specify the selected character. Then, at step S2219 a vocal message indicating that the entry of the selected character is not yet established is stored in a vocal output memory. Then, at step S2225, a vocal output process is performed to release the vocal message stored in the vocal output memory. Program control thereafter exists this processing sequence.

When the second condition is not satisfied, at step S2220 a check is performed to determine whether the count value of the counter EyeBlinkCnt, the value of the flag EyeBlinkStartFlg and the count value of the counter SelectedCnt satisfy the values that are specified under the third condition. When the values satisfy the third condition, this means that the count value of the counter EyeBlinkCnt≧1, the value of the flag EyeBlinkStartFlg=1 and the count value of the counter SelectedCnt≧the preset value are established. When the third condition is satisfied, i.e., when the count value of the counter SelectedCnt has reached the preset value, it is assumed that the selected character can be established by keeping the eyes closed for a predetermined period of time because, while the selected character is confirmed, the count value of the counter EyeBlinkCnt is equal to or greater than "1" and the value of the flag EyeBlinkStartFlg is "1". Then, at step S2221 a vocal message indicating that the selected character can be established by keeping the eyes closed for a predetermined period of time is stored in a vocal output memory. Then, at step S2225, a vocal output process is performed to release the vocal message stored in the vocal output memory. Program control thereafter exists this processing sequence.

When the third condition is not satisfied, at step S2222 a check is performed to determine whether the count value of the counter SelectedCnt satisfies the value that is specified under the fourth condition. When the count value satisfies the fourth condition, this means that the count value of the counter SelectedCnt≧the preset value is established. When the fourth condition is satisfied, i.e., when the count value of the counter SelectedCnt has reached the preset value, it is assumed that the eyes are not closed because the selected character is confirmed but the current condition does not correspond to the first to the third condition. Then, at step S2223 a vocal message indicating that the selected character is confirmed is stored in a vocal output memory. Then, at step S2225, a vocal output process is performed to release the vocal message stored in the vocal output memory. Program control thereafter exists this processing sequence.

When the fourth condition is not satisfied, i.e., when the condition does not corresponds to the first to the fourth condition, it is assumed that the eyes are opened and a character is not yet selected because the count value of the counter SelectedCnt<the preset value is established. Then, at step S2224 a vocal message indicating that a character is not yet selected is stored in a vocal output memory. Then, at step S2225, a vocal output process is performed to release the vocal message stored in the vocal output memory. Program control thereafter exists this processing sequence.

As is described above, in this embodiment, since the user is provided detection result information by the use of a vocal message, the same effect can be acquired as that provided by the eleventh embodiment.

(m) Thirteenth Embodiment

Figure 59:
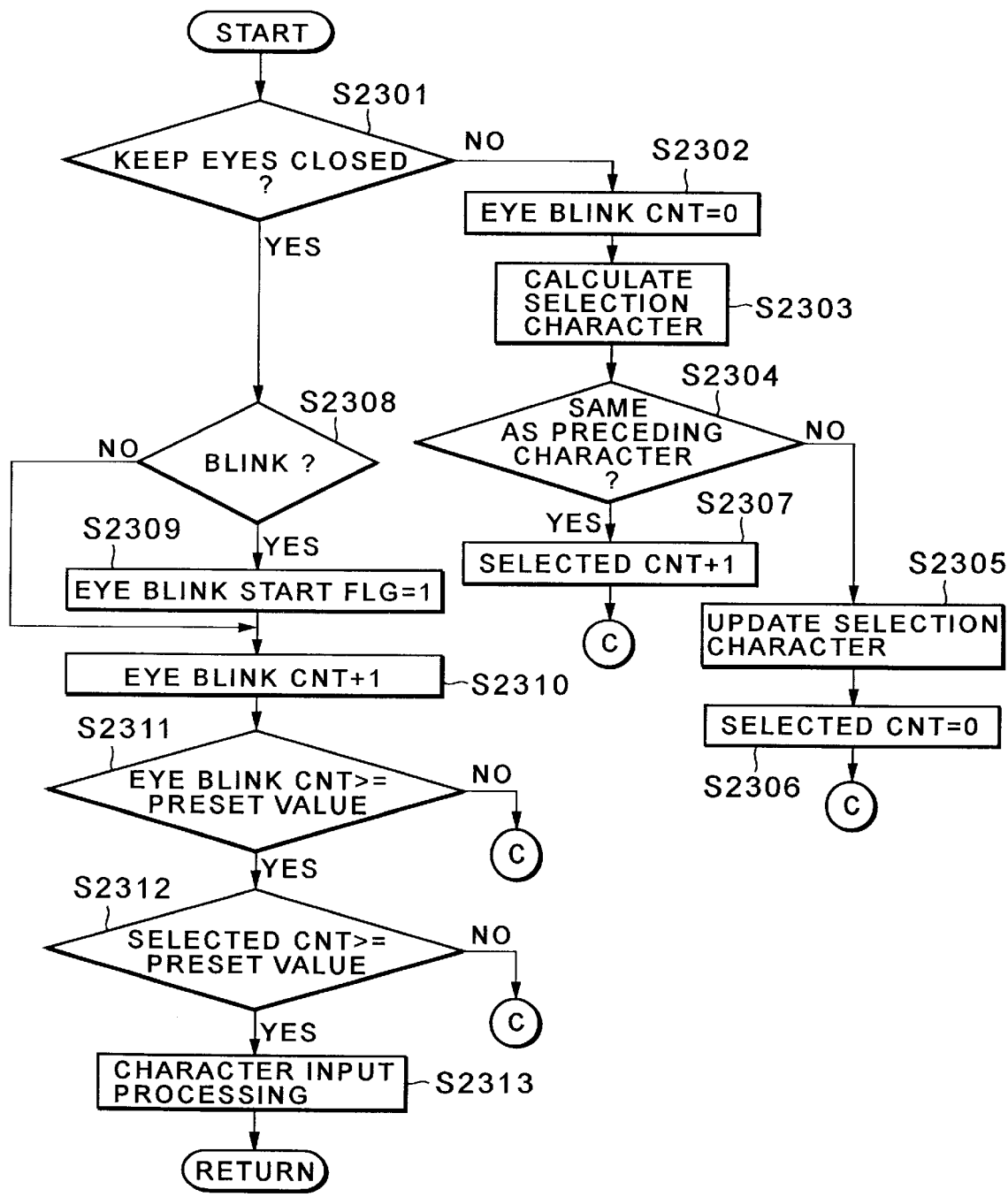
FIG. 59 is a flowchart showing visual axis detection result information notification processing performed by the visual axis entry transmission apparatus according to a thirteenth embodiment of the present invention.
Figure 60:
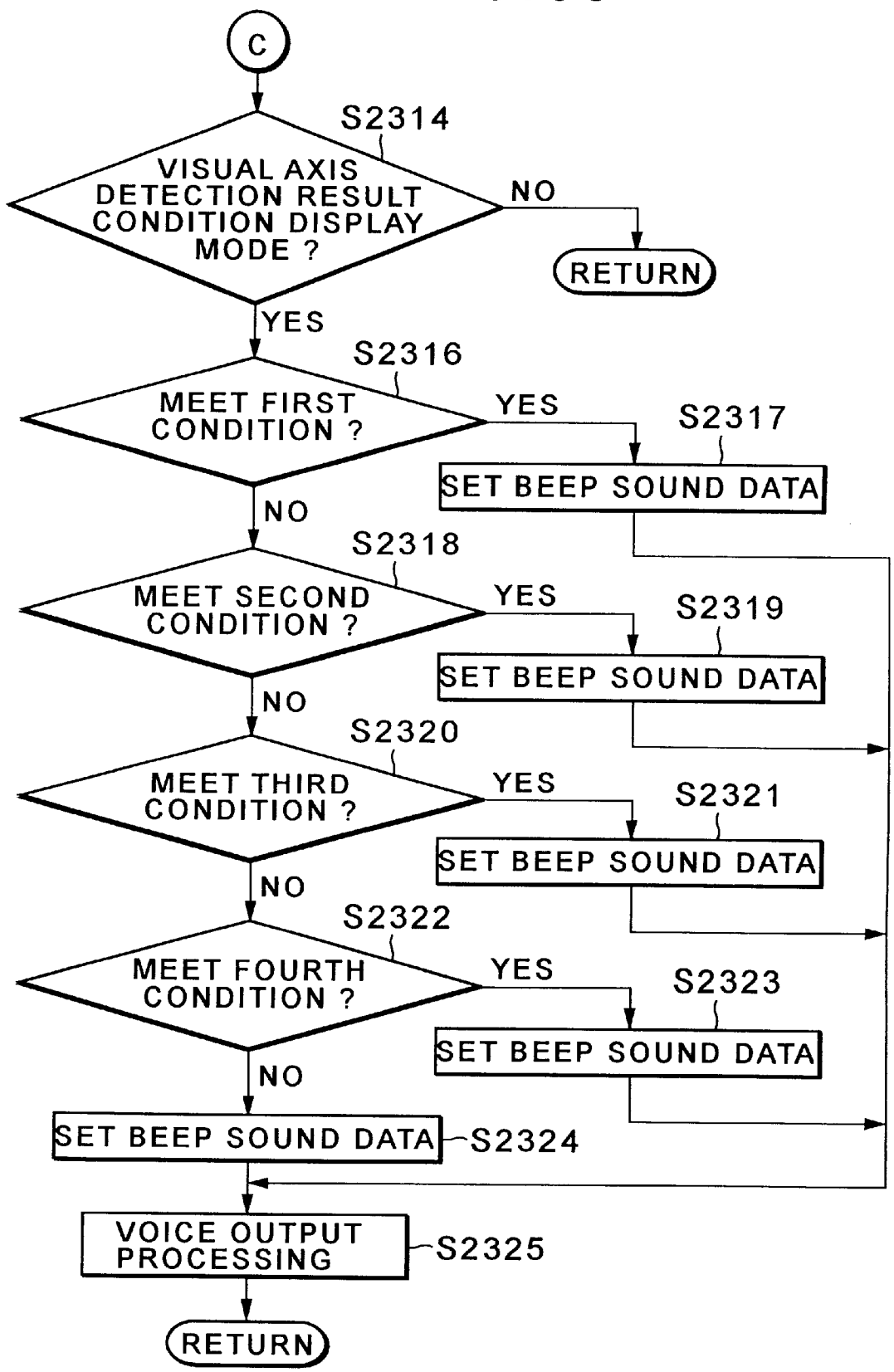
FIG. 60 is a flowchart showing the visual axis detection result information notification processing performed by the visual axis entry transmission apparatus according to the thirteenth embodiment of the present invention.

An explanation will now be given for the visual axis detection result information notification processing according to a thirteenth embodiment while referring to FIGS. 59 and 60. FIGS. 59 and 60 are flowcharts showing the visual axis detection result information notification processing performed by the visual axis entry transmission apparatus according to the thirteenth embodiment.

The arrangement for this embodiment is the same as that for the eleventh embodiment, except that a user is notified of detection result information by receiving a beep sound that is released through a loudspeaker incorporated in a personal computer 1008. Therefore, no explanation for the arrangement will be given.

The visual axis detection result information notification processing will now be described while referring to FIGS. 59 and 60. Since this processing differs from the processing in the twelfth embodiment only in that to send a notification a beep sound is employed instead of the vocal message, only the portion that differs will be explained. Furthermore, since the processing at steps S2301 to S2313 in FIG. 59 is the same as that at steps S2201 to S2213 in the twelfth embodiment, no explanation for it will be given.

After the process at step S2306 or S2307, or upon receipt of a negative response at step S2311 or S2312, program control goes to step S2314. At step S2314, as is shown in FIG. 60, a check is performed to determine whether the visual axis detection result condition display mode is set. When the visual axis detection result condition display mode is not set, program control exits from this processing sequence. When the visual axis detection result condition display mode is set, at step S2316 a check is performed to determine whether the count value of the counter EyeBlinkCnt and the value of the flag EyeBlinkStartFlg satisfy the values that are specified under the first condition. When the values satisfy the first condition, this means that the count value of the counter EyeBlinkCnt≧1 and the value of the flag EyeBlinkStartFlg=0 are established. When the first condition is satisfied, i.e., when the count value of the counter EyeBlinkCnt is equal to or greater than "1" and the value of the flag EyeBlinkStartFlg is "0", it is assumed that the eyes are closed and no blinks are detected. Then, at step S2317 beep sound data indicating that no blinking was detected while the user's eyes were closed is stored in a vocal output memory. Then, at step S2325, a vocal output process is performed to release the beep sound data stored in the vocal output memory. Program control thereafter exists this processing sequence.

When the first condition is not satisfied, at step S2318 a check is performed to determine whether the count value of the counter EyeBlinkCnt, the value of the flag EyeBlink-StartFlg and the count value of the counter SelectedCnt satisfy the values that are specified under the second condition. When the values satisfy the second condition, this means that the count value of the counter EyeBlinkCnt≧1, the value of the flag EyeBlinkStartFlg=1 and the count value of the counter SelectedCnt<the preset value are established. When the second condition is satisfied, i.e., when the count value of the counter EyeBlinkCnt is equal to or greater than "1" and the value of the flag EyeBlinkStartFlg is "1", it is assumed that the entry of the selected character is not yet established because the count value of the counter SelectedCnt does not reach the preset value while the blinks are detected to specify the selected character. Then, at step S2319 beep sound data indicating that the entry of the selected character is not yet established is stored in a vocal output memory. Then, at step S2325, a vocal output process is performed to release the beep sound data stored in the vocal output memory. Program control thereafter exists this processing sequence.

When the second condition is not satisfied, at step S2320 a check is performed to determine whether the count value of the counter EyeBlinkCnt, the value of the flag EyeBlink-StartFlg and the count value of the counter SelectedCnt satisfy the values that are specified under the third condition. When the values satisfy the third condition, this means that the count value of the counter EyeBlinkCnt≧1, the value of the flag EyeBlinkStartFlg=1 and the count value of the counter SelectedCnt≧a the preset value are established. When the third condition is satisfied, i.e., when the count value of the counter SelectedCnt has reached the preset value, it is assumed that the selected character can be established by keeping the eyes closed for a predetermined period of time because, while the selected character is confirmed, the count value of the counter EyeBlinkCnt is equal to or greater than "1" and the value of the flag EyeBlinkStartFlg is "1". Then, at step S2321 beep sound data indicating that the selected character can be established by keeping the eyes closed for a predetermined period of time is stored in a vocal output memory. Then, at step S2325, a vocal output process is performed to release the beep sound data stored in the vocal output memory. Program control thereafter exists this processing sequence.

When the third condition is not satisfied, at step S2322 a check is performed to determine whether the count value of the counter SelectedCnt satisfies the value that is specified under the fourth condition. When the count value satisfies the fourth condition, this means that the count value of the counter SelectedCnt≧the preset value is established. When the fourth condition is satisfied, i.e., when the count value of the counter SelectedCnt has reached the preset value, it is assumed that the eyes are not closed because the selected character is confirmed but the current condition does not correspond to the first to the third condition. Then, at step S2323 beep sound data indicating that the selected character is confirmed is stored in a vocal output memory. Then, at step S2325, a vocal output process is performed to release the beep sound data stored in the vocal output memory. Program control thereafter exists this processing sequence.

When the fourth condition is not satisfied, i.e., when the condition does not corresponds to the first to the fourth condition, it is assumed that the eyes are opened and a character is not yet selected because the count value of the counter SelectedCnt<the preset value is established. Then, at step S2324 beep sound data indicating that a character is not yet selected is stored in a vocal output memory. Then, at step S2325, a vocal output process is performed to release the beep sound data stored in the vocal output memory. Program control thereafter exists this processing sequence.

As is described above, in this embodiment, since the user is provided detection result information by the use of beep sound data, the same effect can be acquired as that provided by the twelfth embodiment.

(n) Fourteenth Embodiment

Figure 61:
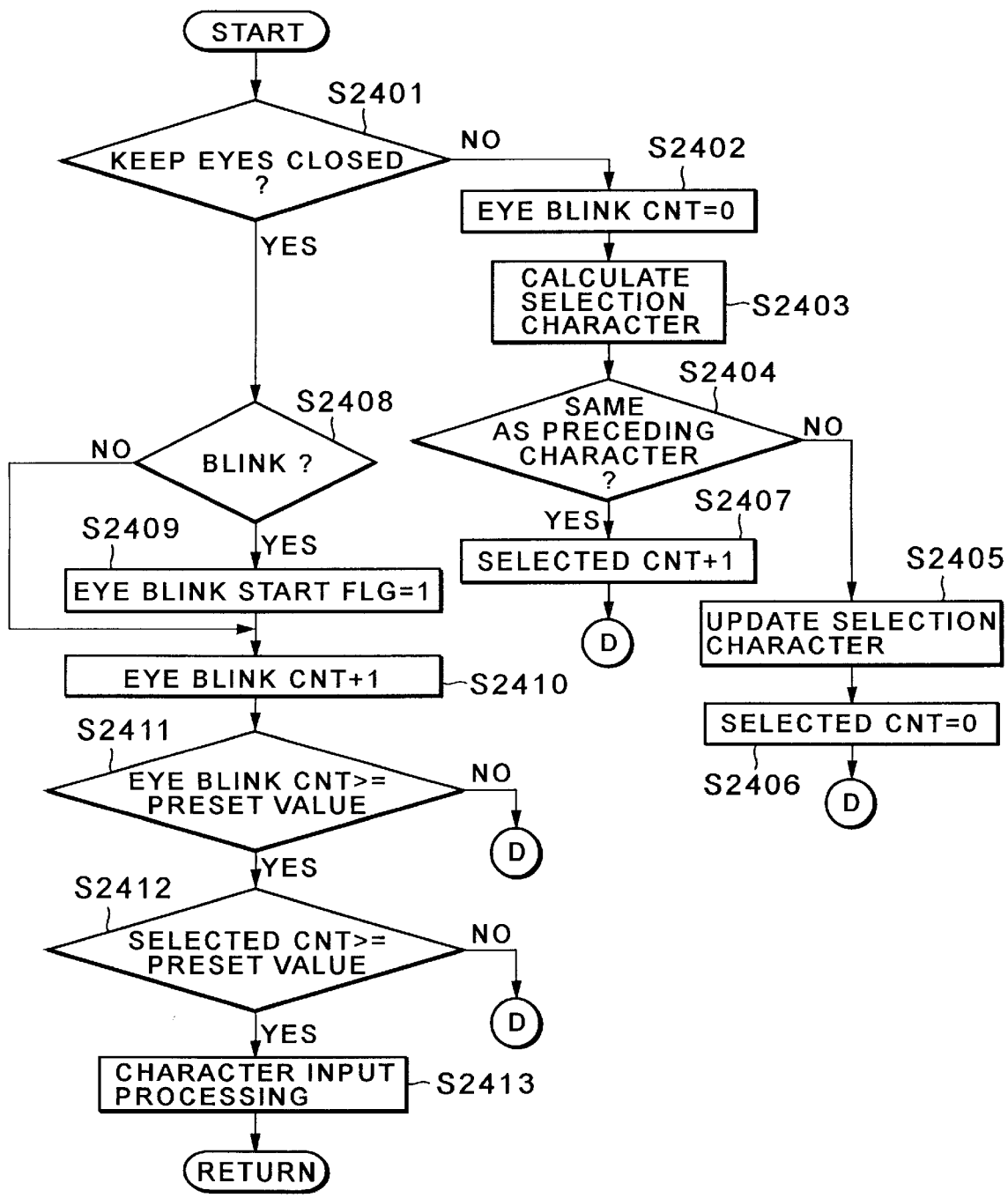
FIG. 61 is a flowchart showing visual axis detection result information notification processing performed by the visual axis entry transmission apparatus according to a fourteenth embodiment of the present invention.
Figure 62:
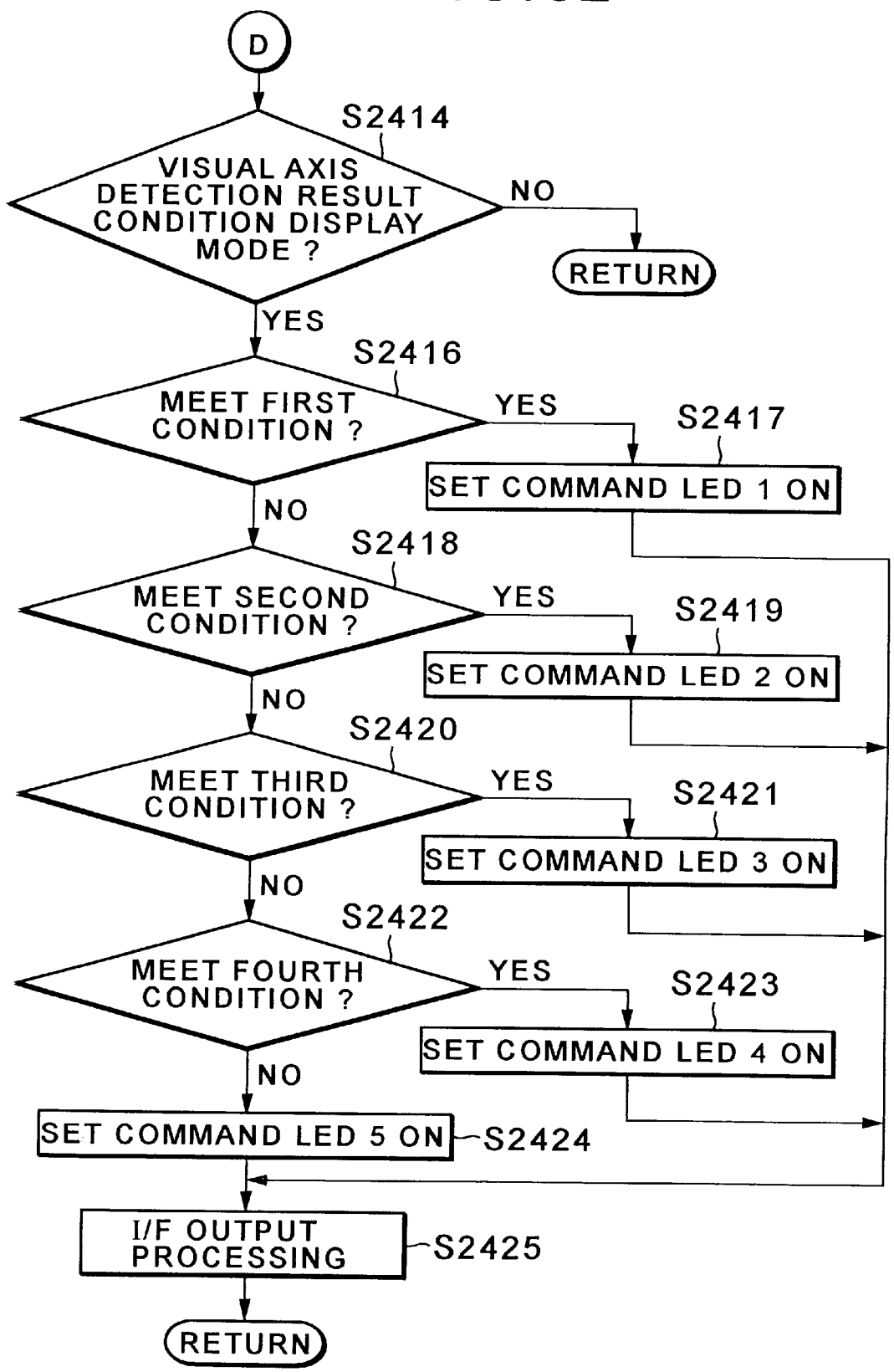
FIG. 62 is a flowchart showing the visual axis detection result information notification processing performed by the visual axis entry transmission apparatus according to the fourteenth embodiment of the present invention.

An explanation will now be given for the visual axis detection result information notification processing according to a fourteenth embodiment while referring to FIGS. 61 and 62. FIGS. 60 and 61 are flowcharts showing the visual axis detection result information notification processing performed by the visual axis entry transmission apparatus according to the fourteenth embodiment.

The arrangement for this embodiment is the same as that for the eleventh embodiment, except that a plurality of light emitting diodes (not shown) are incorporated in a head-mounted display unit 1006 and a user is notified of detection result information by controlling light emitted by these diodes. Therefore, no explanation for the arrangement will be given.

The visual axis detection result information notification processing will now be described while referring to FIGS. 61 and 62. Since this processing differs from the processing in the twelfth embodiment only in that to send a notification the ON states of a plurality of light emitting diodes, which emit visible light, are employed instead of the vocal message, only the portion that differs will be explained. Furthermore, since the processing at steps S2401 to S2413 in FIG. 61 is the same as that at steps S2201 to S2213 in the twelfth embodiment, no explanation for it will be given.

After the process at step S2406 or S2407, or upon receipt of a negative response at step S2411 or S2412, program control goes to step S2414. At step S2414, as is shown in FIG. 62, a check is performed to determine whether the visual axis detection result condition display mode is set. When the visual axis detection result condition display mode is not set, program control exits from this processing. When the visual axis detection result condition display mode is set, at step S2416 a check is performed to determine whether the count value of the counter EyeBlinkCnt and the value of the flag EyeBlinkStartFlg satisfy the values that are specified under the first condition. When the values satisfy the first condition, this means that the count value of the counter EyeBlinkCnt≧1 and the value of the flag EyeBlinkStartFlg=0 are established. When the first condition is satisfied, i.e., when the count value of the counter EyeBlinkCnt is equal to or greater than "1" and the value of the flag EyeBlinkStartFlg is "0", it is assumed that the eyes are closed and no blinks are detected. Then, at step S2417 an ON command for a light emitting diode LED1 indicating that no blinking was detected while the eyes were closed is stored in an I/F output memory. At step S2425 the ON command is output to the light emitting diode LED1 by the I/F output memory, and program control thereafter exits this processing sequence. Upon receiving the ON command, the light emitting diode LED1 is turned on to notify the user that no blinking was detected while the eyes were closed.

When the first condition is not satisfied, at step S2418 a check is performed to determine whether the count value of the counter EyeBlinkCnt, the value of the flag EyeBlinkStartFlg and the count value of the counter SelectedCnt satisfy the values that are specified under the second condition. When the values satisfy the second condition, this means that the count value of the counter EyeBlinkCnt≧1, the value of the flag EyeBlinkStartFlg=1 and the count value of the counter SelectedCnt<the preset value are established. When the second condition is satisfied, i.e., when the count value of the counter EyeBlinkCnt is equal to or greater than "1" and the value of the flag EyeBlinkStartFlg is "1", it is assumed that the entry of the selected character is not yet established because the count value of the counter SelectedCnt does not reach the preset value while the blinks are detected to specify the selected character. Then, at step S2419 an ON command for a light emitting diode LED2 indicating that the entry of the selected character is not yet established is stored in an I/F output memory. At step S2425 the ON command is output to the light emitting diode LED2 by the I/F output memory, and program control thereafter exits this processing sequence. Upon receiving the ON command, the light emitting diode LED2 is turned on to notify the user that the entry of the selected character is not yet established.

When the second condition is not satisfied, at step S2420 a check is performed to determine whether the count value of the counter EyeBlinkCnt, the value of the flag EyeBlinkStartFlg and the count value of the counter SelectedCnt satisfy the values that are specified under the third condition. When the values satisfy the third condition, this means that the count value of the counter EyeBlinkCnt≧1, the value of the flag EyeBlinkStartFlg=1 and the count value of the counter SelectedCnt≧the preset value are established. When the third condition is satisfied, i.e., when the count value of the counter SelectedCnt has reached the preset value, it is assumed that the selected character can be established by keeping the eyes closed for a predetermined period of time because, while the selected character is confirmed, the count value of the counter EyeBlinkCnt is equal to or greater than "1" and the value of the flag EyeBlinkStartFlg is "1". Then, at step S2421 an ON command for a light emitting diode LED3 indicating that the selected character can be established by keeping the eyes closed for a predetermined period of time is stored in an I/F output memory. Then, at step S2425 the ON command is output to the light emitting diode LED3 by the I/F output memory, and program control thereafter exits this processing sequence. Upon receiving the ON command, the light emitting diode LED3 is turned on to notify the user that the selected character can be established by keeping the eyes closed for a predetermined period of time.

When the third condition is not satisfied, at step S2422 a check is performed to determine whether the count value of the counter SelectedCnt satisfies the value that is specified under the fourth condition. When the count value satisfies the fourth condition, this means that the count value of the counter SelectedCnt≧the preset value is established. When the fourth condition is satisfied, i.e., when the count value of the counter SelectedCnt has reached the preset value, it is assumed that the eyes are not closed because the selected character is confirmed but the current condition does not correspond to the first to the third condition. Then, at step S2423 an ON command for a light emitting diode LED4 indicating that the selected character is confirmed is stored in an I/F output memory. At step S2425 the ON command is output to the light emitting diode LED4 by the I/F output memory, and program control thereafter exits this processing sequence. Upon receiving the ON command, the light emitting diode LED4 is turned on to notify the user that the selected character is confirmed.

When the fourth condition is not satisfied, i.e., when the condition does not corresponds to the first to the fourth condition, it is assumed that the eyes are opened and a character is not yet selected because the count value of the counter SelectedCnt<the preset value is established. Then, at step S2424 an ON command for a light emitting diode LED5 indicating that a character is not yet selected is stored in an I/F output memory. At step S2425 the ON command is output to the light emitting diode LED5 by the I/F output memory, and program control thereafter exits this processing sequence. Upon receiving the ON command, the light emitting diode LED5 is turned on to notify the user that a character is not yet selected.

As is described above, in this embodiment, since the user is notified of the detection result information by turning on the light emitting diodes LED1 to LED5, the same effect as in the eleventh embodiment can be obtained.

(o) Fifteenth Embodiment

Figure 63:
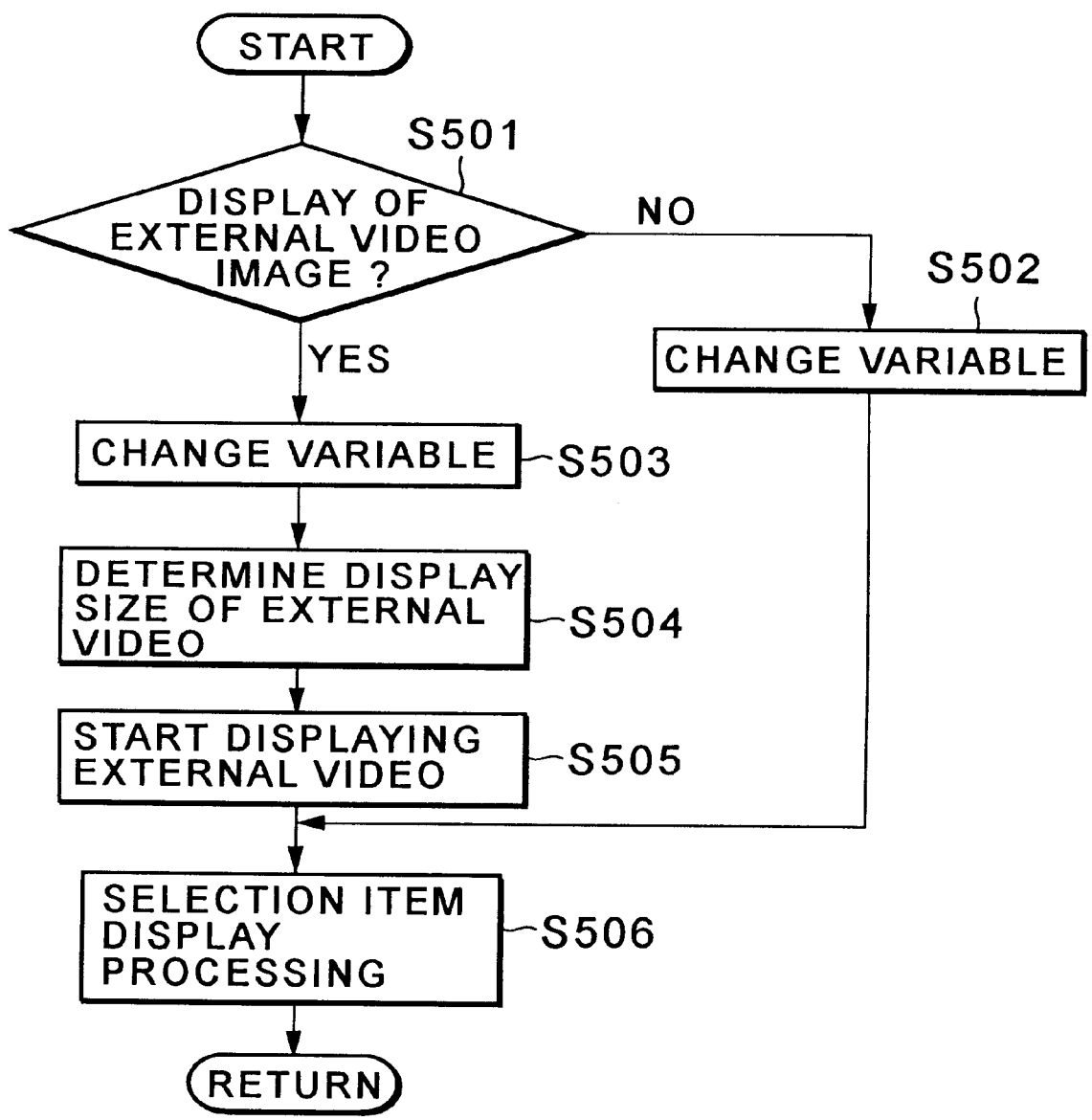
FIG. 63 is a flowchart showing external video display processing performed by the visual axis entry transmission apparatus according to a fifteenth embodiment of the present invention.
Figure 64:
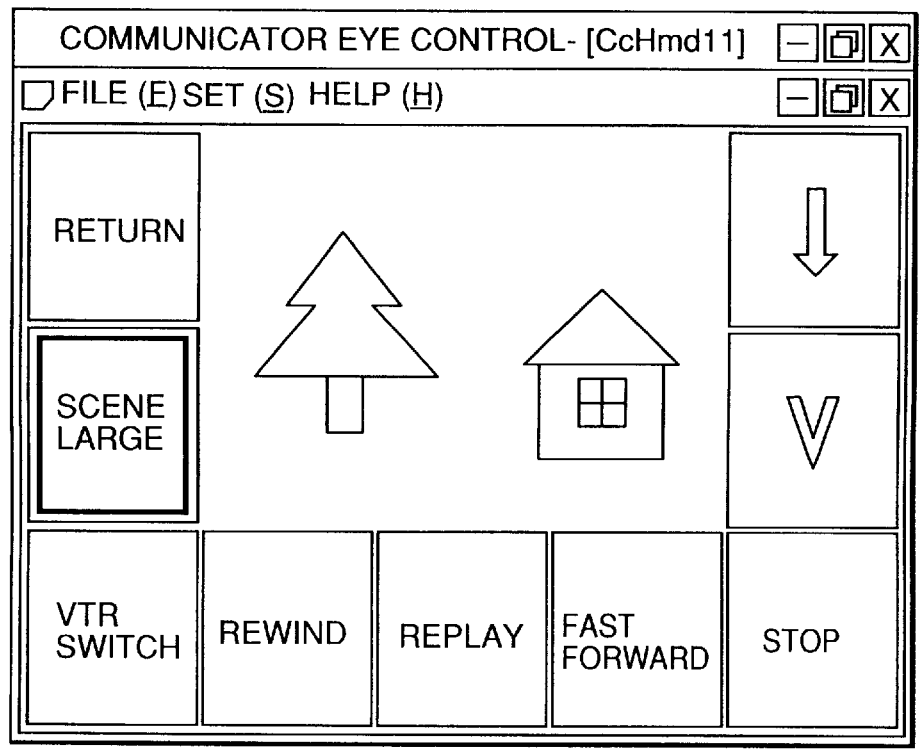
FIG. 64 is a diagram showing an example screen on a head-mounted display that is obtained through the external video display processing in FIG. 63.
Figure 65:
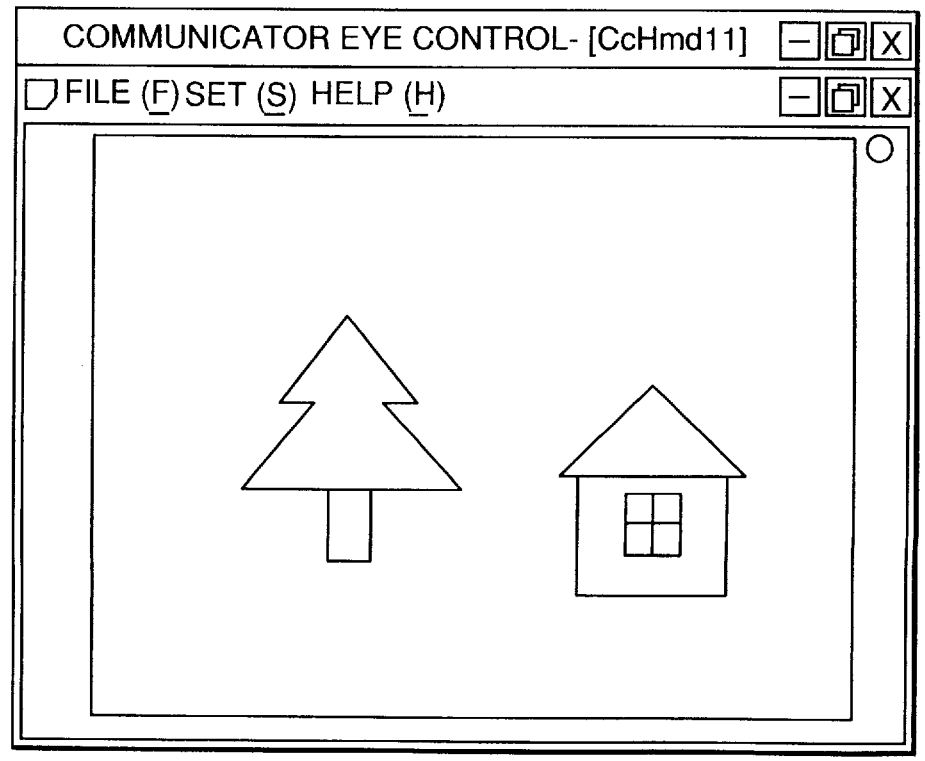
FIG. 65 is a diagram showing another example screen on the head-mounted display that is obtained through the external video display processing in FIG. 63.

A fifteenth embodiment of the present invention will be described while referring to FIGS. 63 to 65. FIG. 63 is a flowchart showing external video display processing performed by a visual axis entry transmission apparatus according to the fifteenth embodiment of the present invention, and FIGS. 64 and 65 are diagrams showing example screens displayed on the head-mounted display unit 1006 via the external video display processing in FIG. 63.

In this embodiment, the personal computer 1008 includes an interface for receiving an external video, and performs a display process whereby the received external video and the display panel, on which are displayed available choices by the visual axis input, are arranged together on the liquid crystal display device 1002 of the head-mounted display unit 1006; and a process, based on an instruction from the user, for setting an arbitrary display area ratio of the external video image to the display panel that are displayed on the liquid crystal display device 1002 of the head-mounted display unit 1006.

The external video display processing in this embodiment will now be described while referring to FIG. 63.

First, at step S501 a check is performed to determine whether an external video image is to be displayed. When an external video image is not to be displayed, at step S502 a variable that indicates the display area ratio of the external video to the display panel on liquid crystal display device 1002 is changed to a value that is applicable when only display panel is displayed on the screen. Program control then goes to step S506, whereat choices are displayed on the display panel. Program control thereafter exits this processing sequence.

When at step S501 the external video image is to be displayed, at step S503 a variable that represents the display area ratio of the external video image to the display panel on the liquid crystal display device 1002 is set to a desired value. At step S504 the display size of the external video image is determined based on the ratio set at step S503. At step S505 the control for the liquid crystal display circuit 1007 is initiated to display the external video image on the liquid crystal display device 1002. At step S506 options are displayed in an area other than the display area for the external video image. Program control thereafter exits this processing sequence.

In this processing, the screen shown in FIG. 64 can be provided for the user. When the external video is enlarged on the screen in FIG. 64, the "Scene, large" icon is selected by the entry of the visual axis. As a result, as is shown in FIG. 65, the external video image is enlarged and displayed using the entire display area of the liquid crystal display device 1002. At this time, the options are not displayed and only an icon (a round button at the right upper corner of the screen) for returning to the screen shown in FIG. 64 is displayed.

In this embodiment, therefore, the user can monitor the external video image as well as the options.

(p) Sixteenth Embodiment

Figure 66:
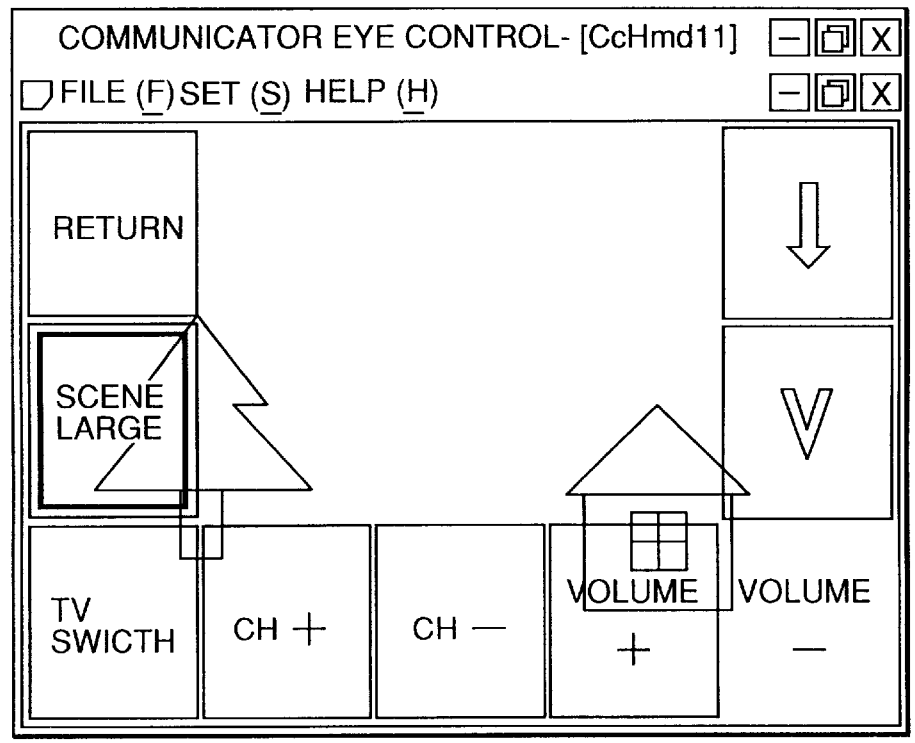
FIG. 66 is a diagram showing an example screen on the head-mounted display that is obtained through external video display processing performed by the visual axis entry transmission apparatus according to a sixteenth embodiment of the present invention.
Figure 67:
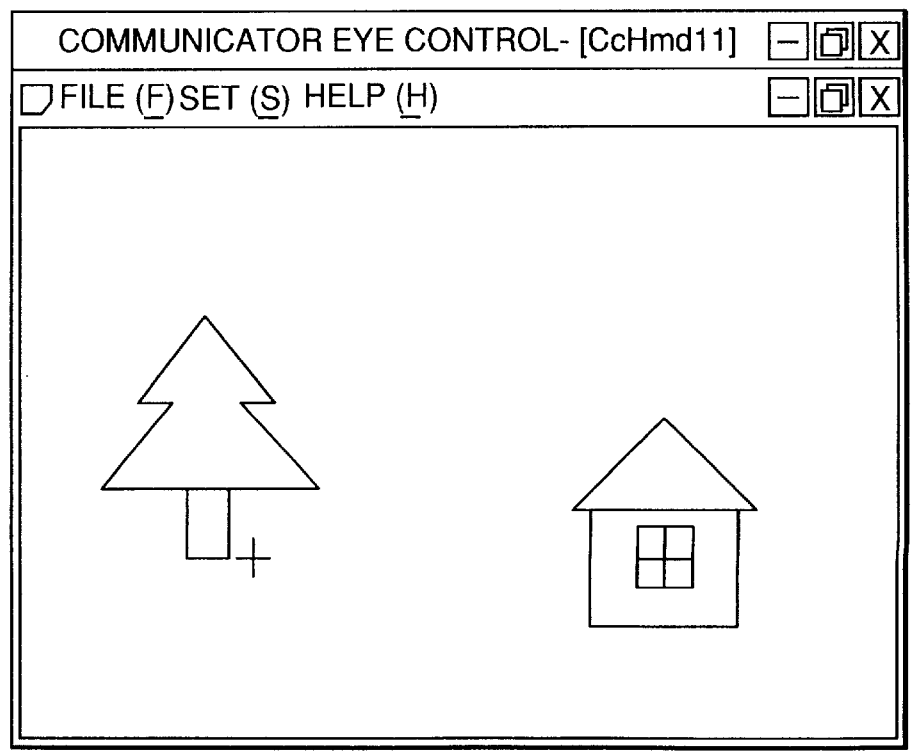
FIG. 67 is a diagram showing another example screen on the head-mounted display that is obtained through the external video display processing performed by the visual axis entry transmission apparatus according to the sixteenth embodiment of the present invention.
Figure 68:
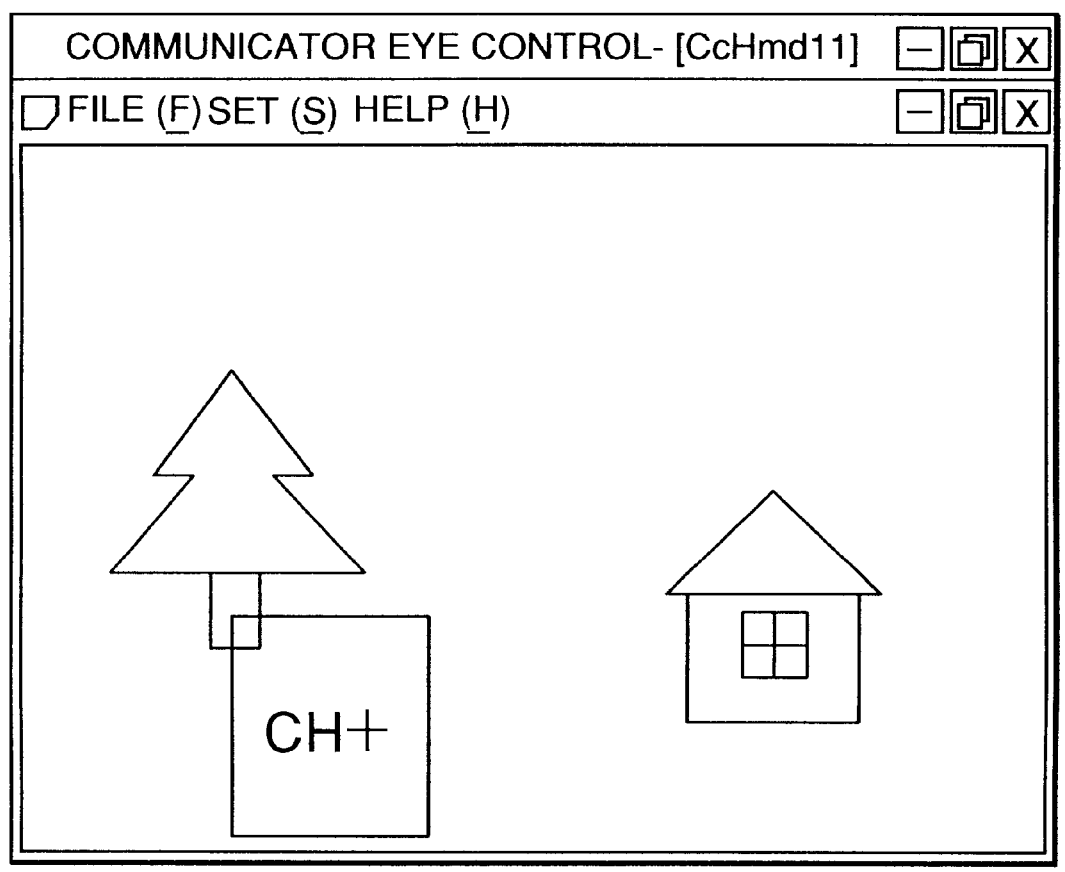
FIG. 68 is a diagram showing an additional example screen on the head-mounted display that is obtained through the external video display processing performed by the visual axis entry transmission apparatus according to the sixteenth embodiment of the present invention.

A sixteenth embodiment of the present invention will now be described while referring to FIGS. 66 to 68. FIGS. 66 to 68 are diagrams showing example screens displayed on the head-mounted display unit 1006 via the video display processing performed by a visual axis entry transmission apparatus according to the sixteenth embodiment of the present invention.

In this embodiment, the personal computer 1008 includes an interface for receiving an external video image, and performs a display process for overlapping options, on the screen of the liquid crystal display device 1002 of the head-mounted display unit 1006, that can be selected by moving the visual axis to their screen locations. In addition, whether the external video image and the options are to be displayed overlapping can be selected. Furthermore, a process is performed whereby, when a specific portion of the external video image is selected by moving the visual axis to the location the portion occupies on the screen on which only the external video image is displayed, whether the portion is in an option display screen location is determined, and whereby, when the portion to which the visual axis is moved is in an option display screen location the corresponding option for that location is displayed overlapping the external video image.

In the display processing in this embodiment, the external video image and the options can be displayed overlapping each other, as is shown in FIG. 66.

Furthermore, when a specific portion ("+" in FIG. 67) of the external video image is selected by moving the visual axis to the location the portion occupies on the screen on which only the external video image is displayed, whether the portion is in an option screen display location is determined. When the position to which the visual axis is moved is in a screen display location for option "CH+", the option "CH+" is displayed overlapping the external video, as is shown in FIG. 68. When the option is selected by the visual axis being moved to its screen location, it is input and the corresponding process is performed.

Therefore, in this embodiment, the user can select an option by using the visual axis while monitoring the externally input video image.

(q) Seventeenth Embodiment

A seventeenth embodiment of the present invention will now be described while referring to FIGS. 69 to 72. FIGS. 69 to 72 are diagrams showing example screens displayed on the head-mounted display unit 1006 via the video image display processing performed by a visual axis entry transmission apparatus according to the seventeenth embodiment of the present invention.

In this embodiment, the display form for an option is changed and the option is displayed in its new form on the liquid crystal display device 1002 of the head-mounted display unit 1006.

Figure 71:
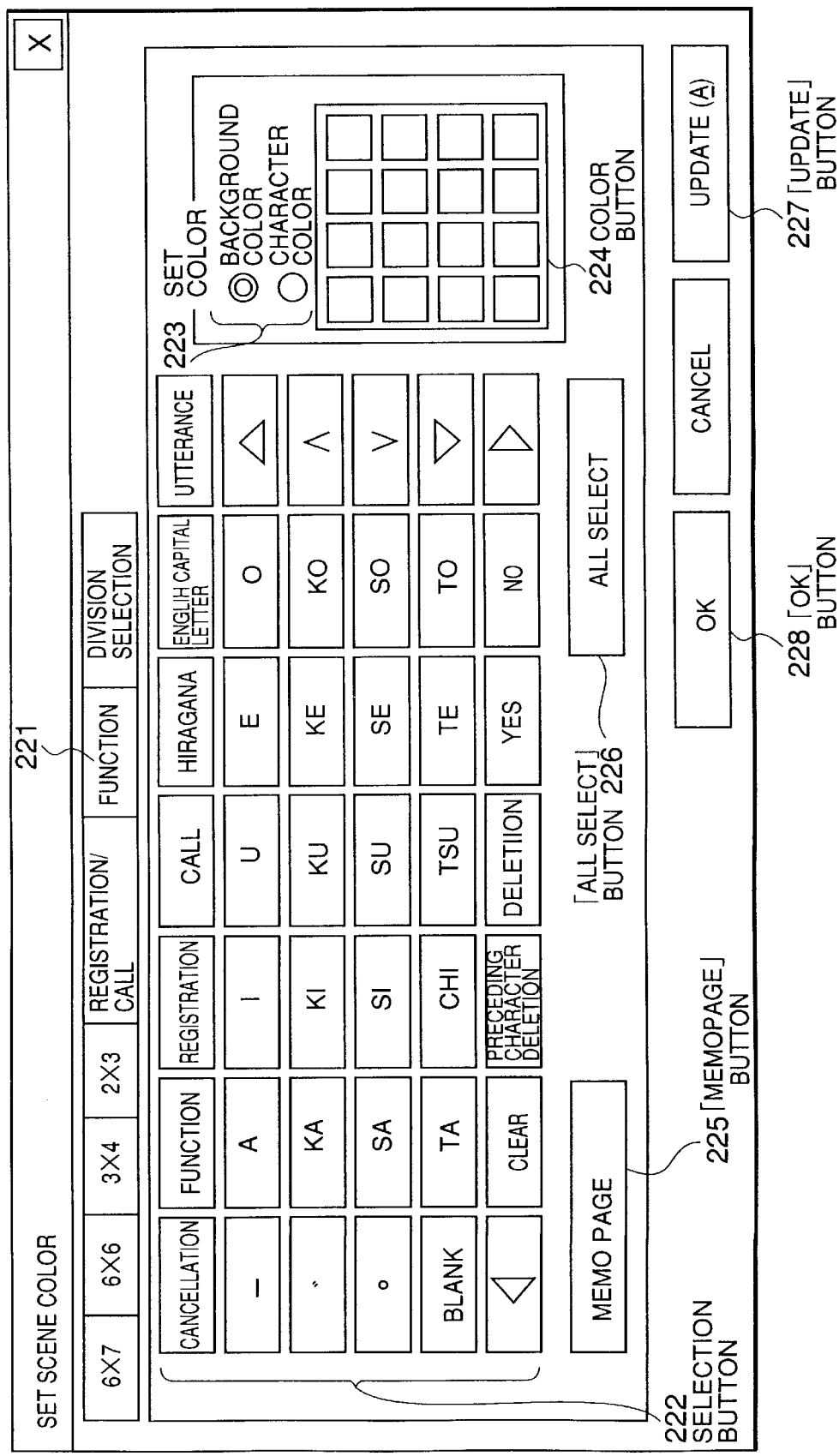
FIG. 71 is a diagram showing an additional example screen on the head-mounted display that is obtained through the external video display processing performed by the visual axis entry transmission apparatus according to the seventeenth embodiment of the present invention.

In the display processing for this embodiment, in order to change the option display forms in FIG. 69 that are displayed on the head-mounted display unit 1006, on the screen the "Set" menu option is selected and the menu screen in FIG. 70 is opened. When the "Set scene color" menu item is selected on this screen, the "Set scene color" dialogue box in FIG. 71 is opened, a specific scene is selected in the dialogue box using a scene selection tag 221, and a color change target option is instructed by a selection button 222. Then, a background color/character color check button 223 is used to instruct a background color change or a character color change in the "Set color" portion, and a color button 224 is employed to designate a desired color.

Furthermore, to change the color used for a memo page display, a "MemoPage" button 225 is selected. Then, the background color change or the character color change in the "Set color" portion is instructed by using the background color/character color check button 223, and a desired color is selected by using the color button 224. Finally, the selection button 222 is employed.

In addition, to display in one color all the options and the memopage display portion on the selection screen, a "Select all" button 226 is used. Then, the background color change or the character color change is instructed by using the background color/character color check button 223, and a desired color is selected by using the color button 224. When a desired color has been set in this manner, an "Update" button 227 in the lower portion of the dialogue box is selected, so that the options are displayed in a different color on the head-mounted display unit 1006. When an "OK" button 228 is selected instead of the "Update" button 227 and the "Set scene color" dialogue box is closed, the option colors can be changed on the head-mounted display unit 1006.

When, for example, the color for "A" in the choices is changed to black, and the background color is changed to white using the "Set scene color" dialogue box, the screen in FIG. 72 is displayed on the head-mounted display unit 1006.

As is described above, in this embodiment, the options can be so displayed that the user can easily identify them.

(r) Eighteenth Embodiment

Figure 73:
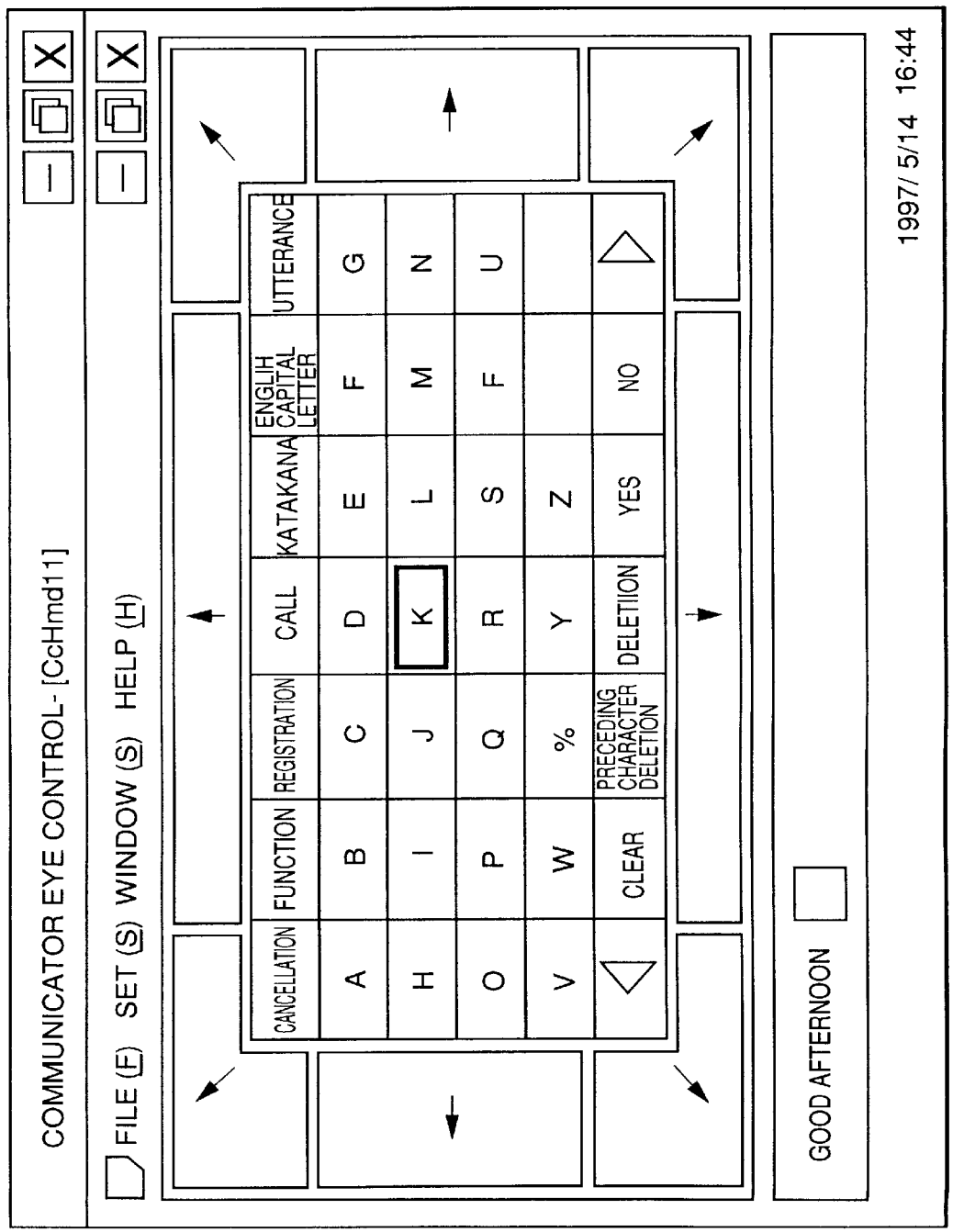
FIG. 73 is a diagram showing an example screen on the head-mounted display that is obtained through selection processing performed by the visual axis entry transmission apparatus according to an eighteenth embodiment of the present invention.
Figure 74:
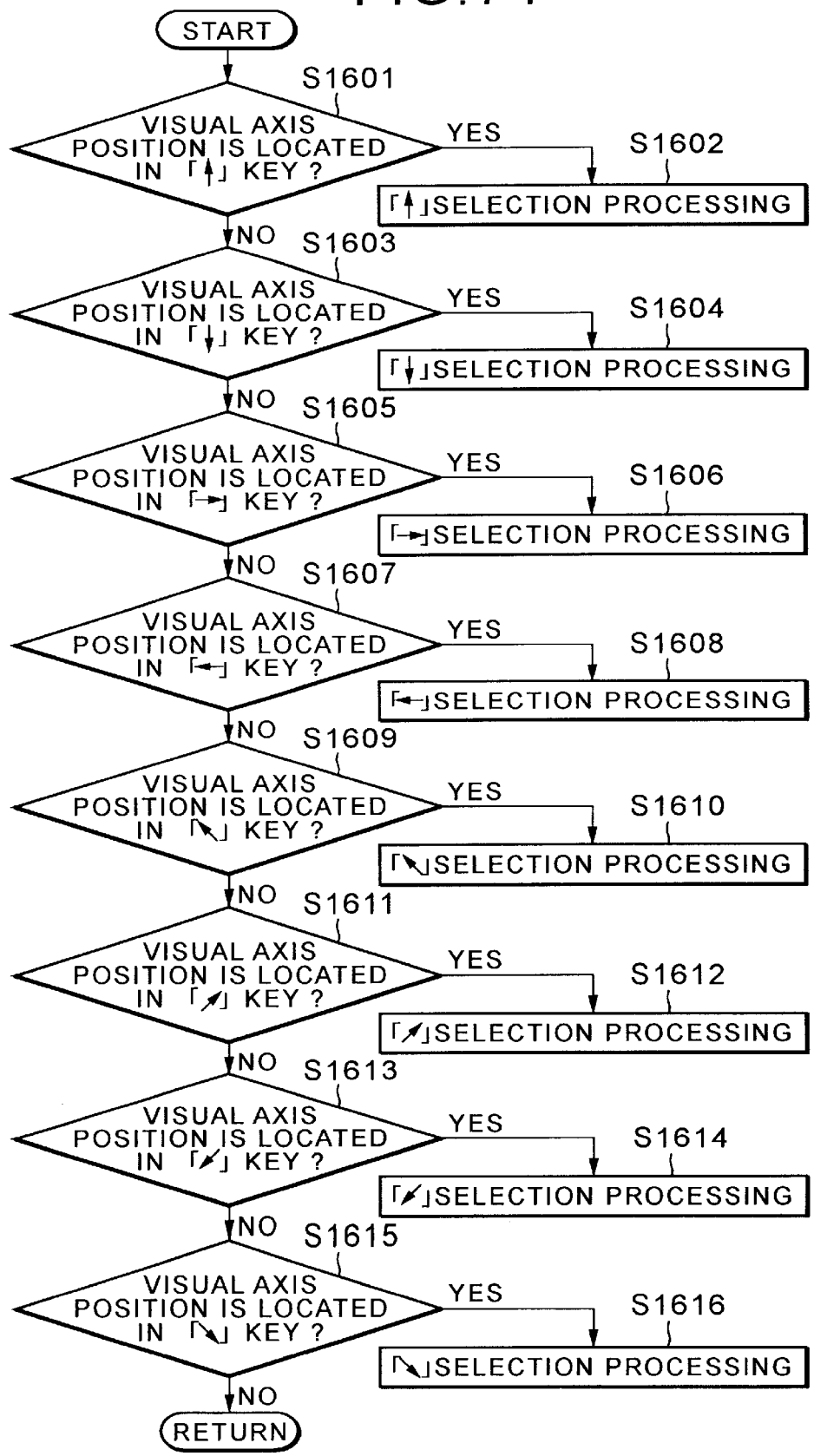
FIG. 74 is a flowchart showing the selection processing performed by the visual axis entry transmission apparatus according to the eighteenth embodiment of the present invention.
Figure 75:
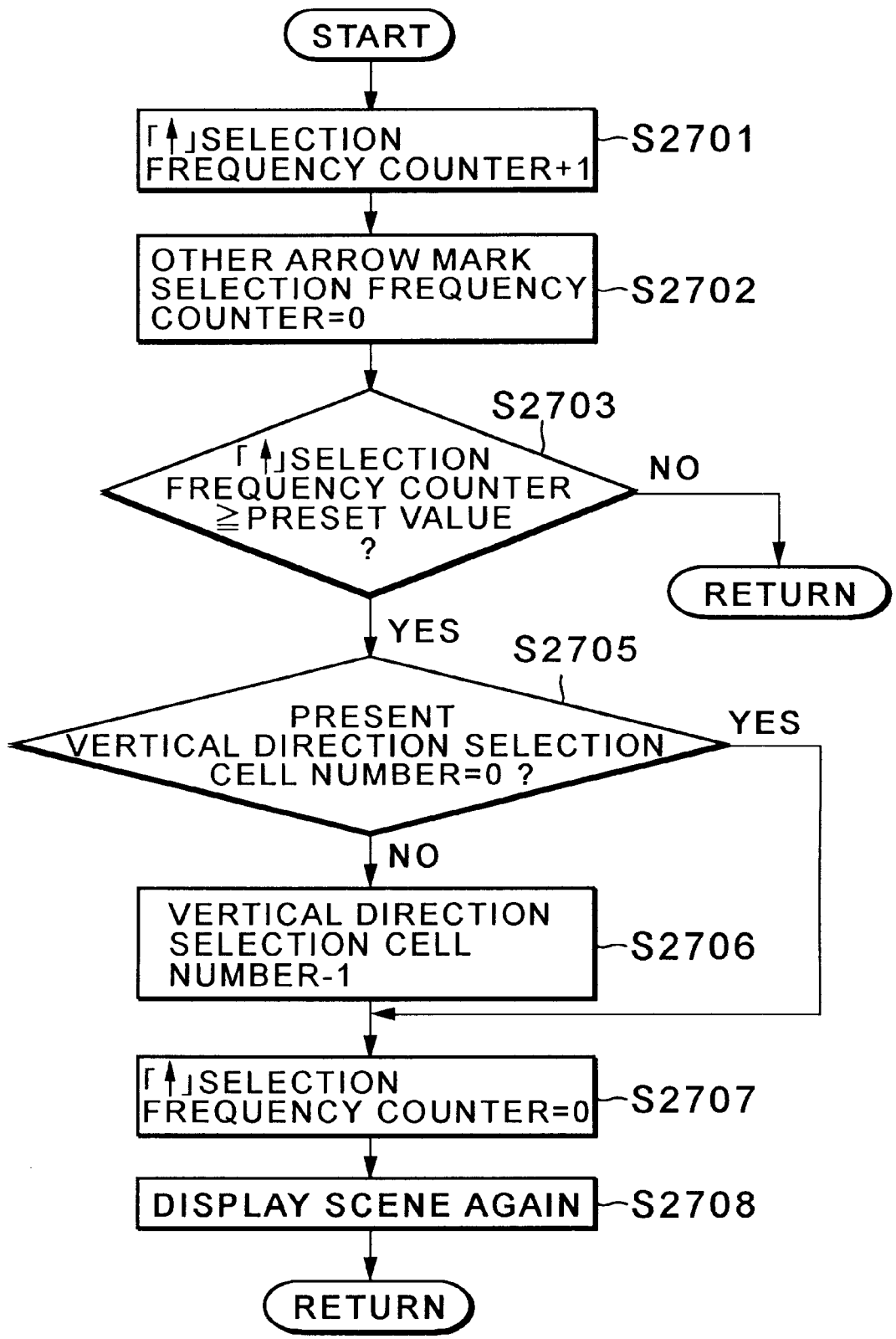
FIG. 75 is a flowchart showing an up arrow ("↑") key selection process at step S1602 in FIG. 74.
Figure 76:
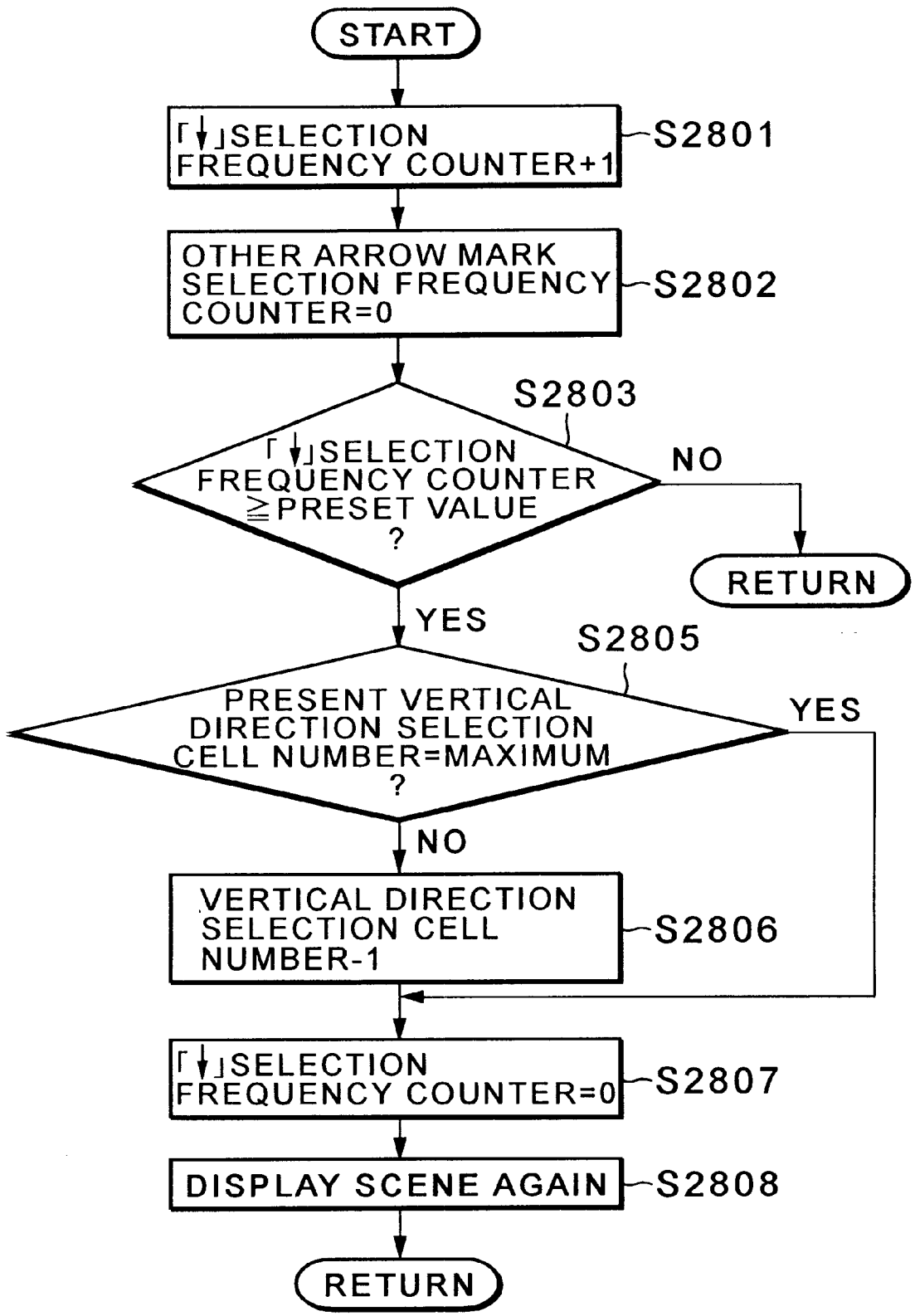
FIG. 76 is a flowchart showing a down arrow ("↓") key selection process at step S1604 in FIG. 74.
Figure 77:
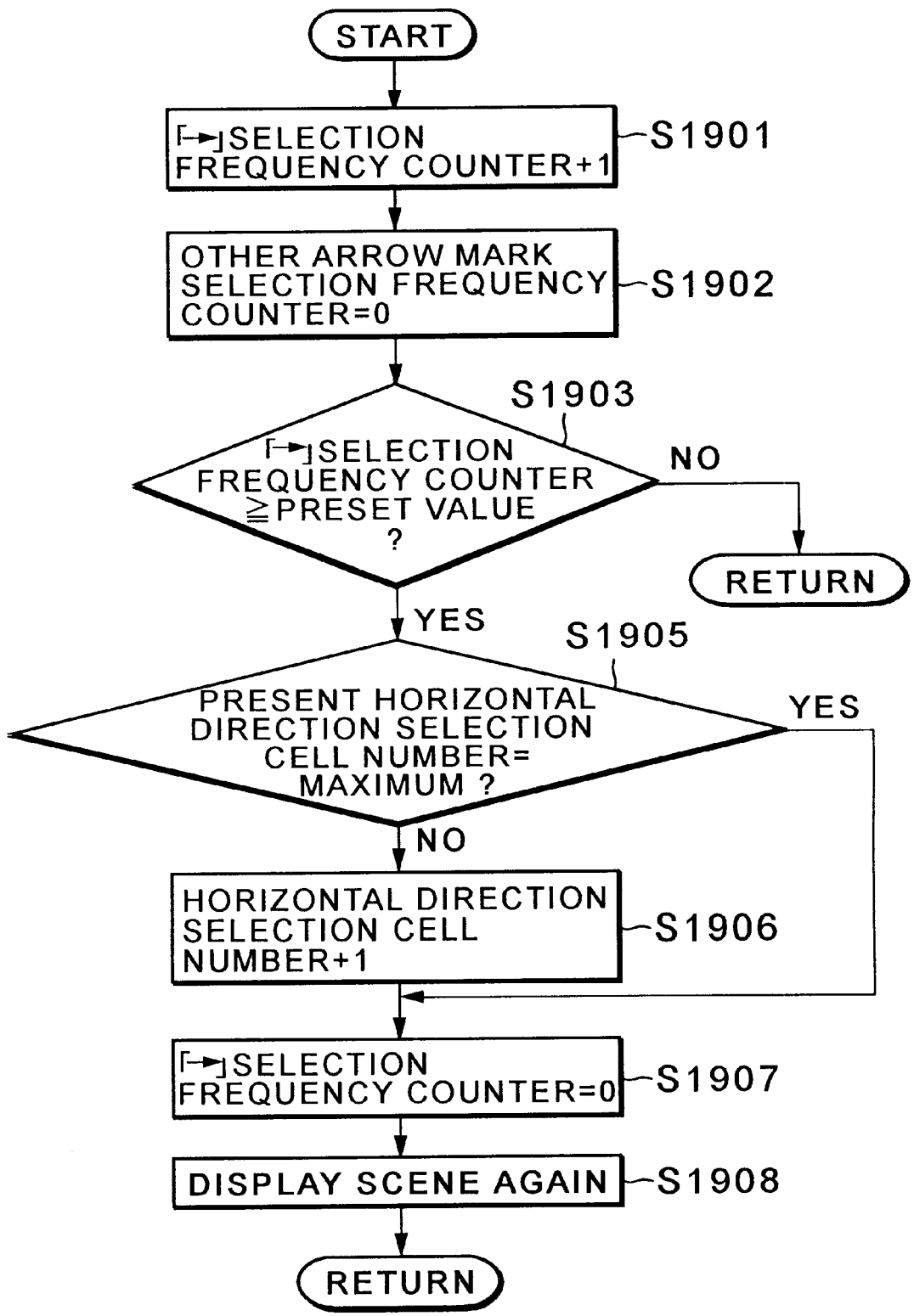
FIG. 77 is a flowchart showing a right arrow ("→") key selection process at step S1606 in FIG. 74.
Figure 78:
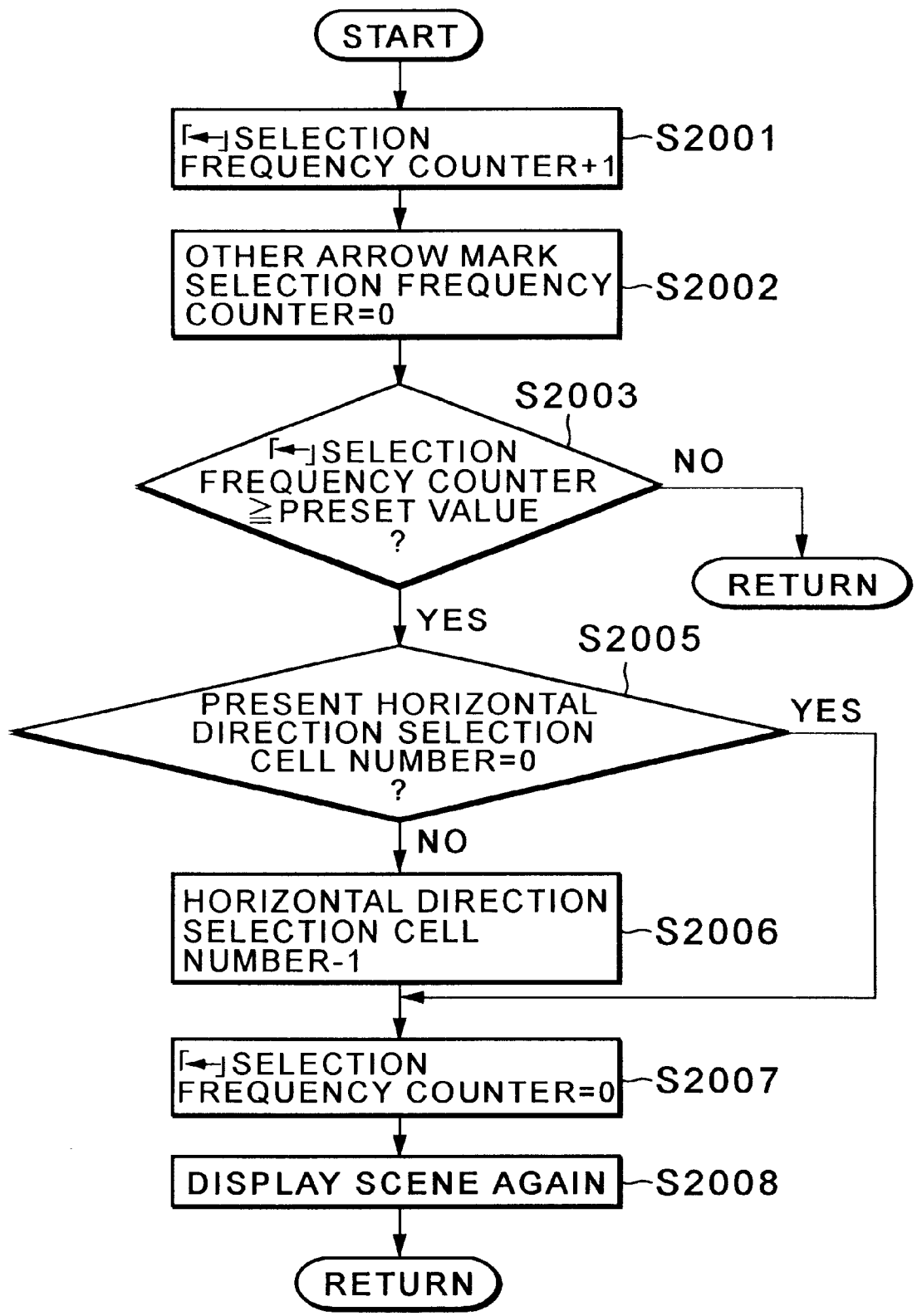
FIG. 78 is a flowchart showing a left arrow ("←") key selection process at step S1608 in FIG. 74.
Figure 79:
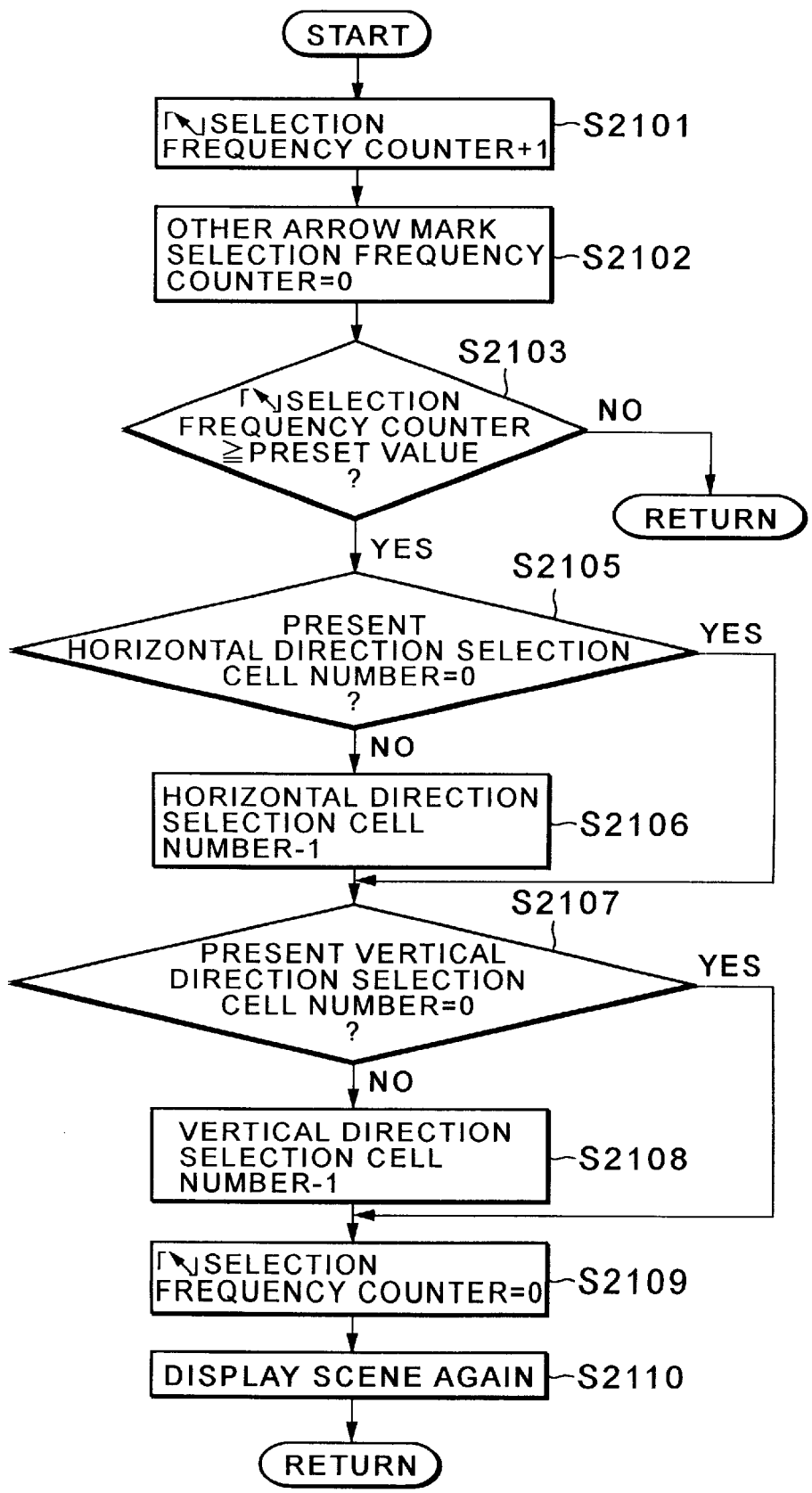
FIG. 79 is a flowchart showing a left upward pointing arrow ("↖") key selection process at step S1610 in FIG. 74.
Figure 80:
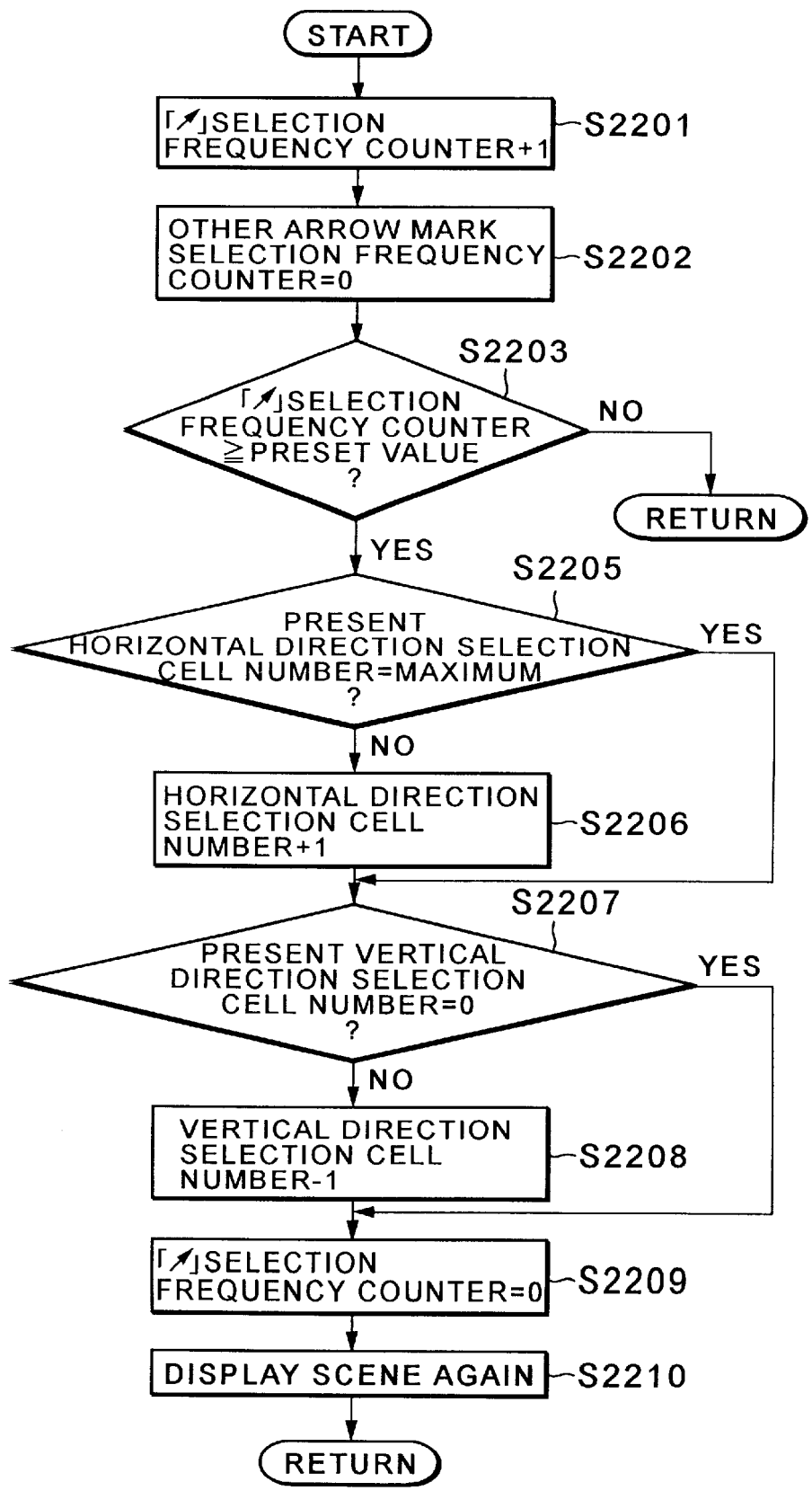
FIG. 80 is a flowchart showing a right upward pointing arrow ("↗") key selection process at step S1612 in FIG. 74.
Figure 81:
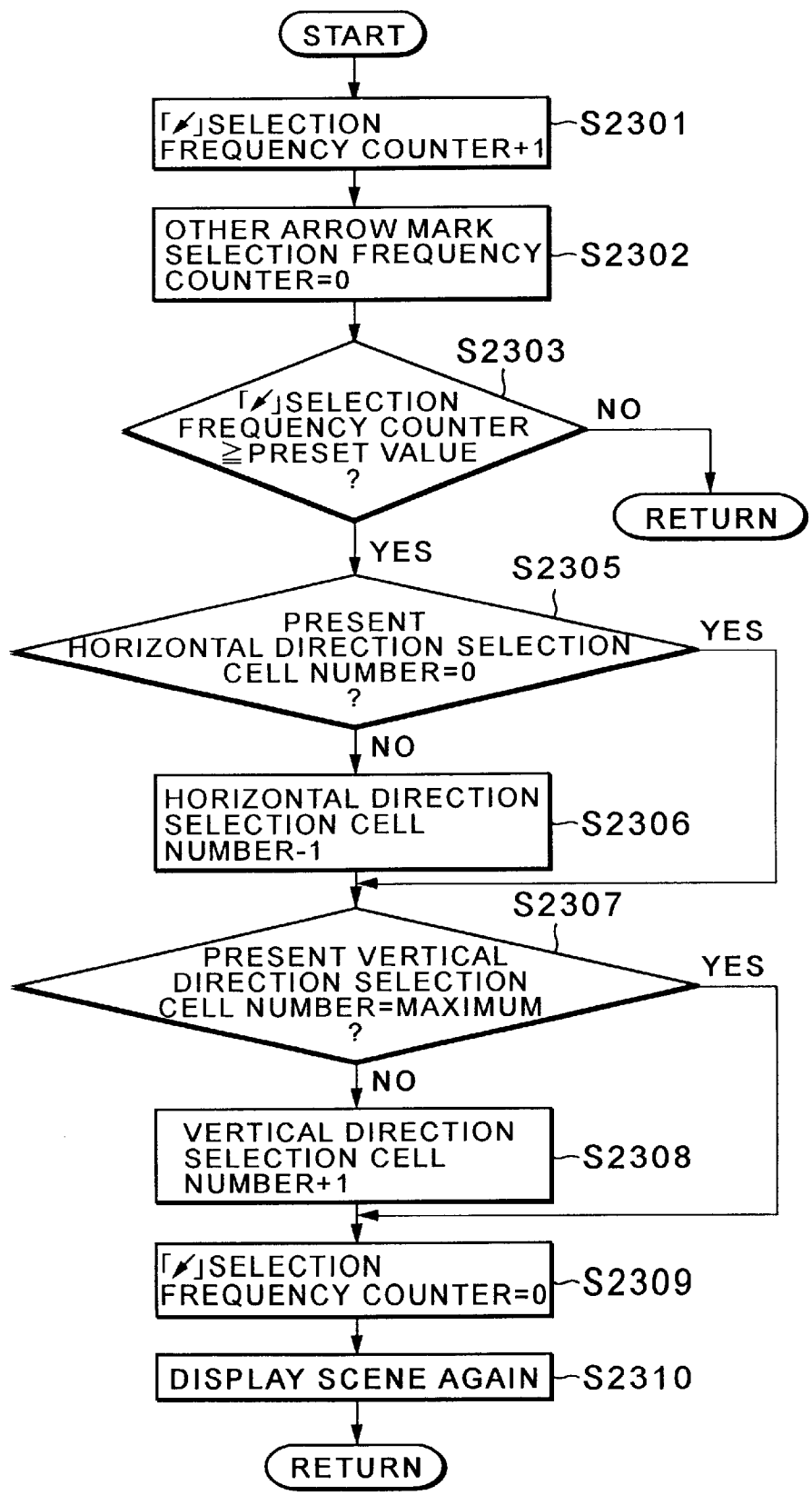
FIG. 81 is a flowchart showing a left downward pointing arrow ("↙") key selection process at step S1614 in FIG. 74.
Figure 82:
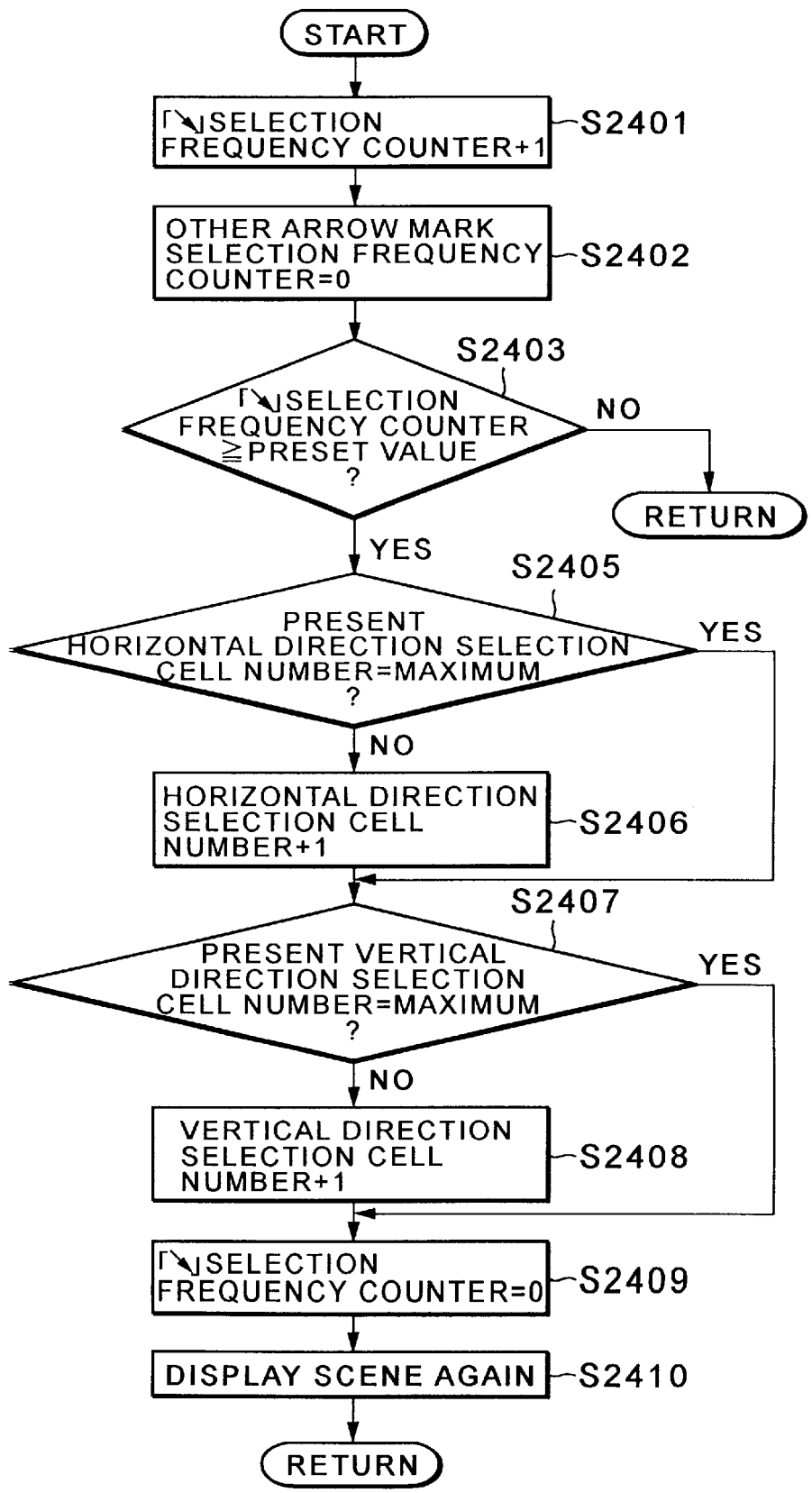
FIG. 82 is a flowchart showing a right downward pointing arrow ("↘") key selection process at step S1616 in FIG. 74.

An eighteenth embodiment of the present invention will now be described while referring to FIGS. 73 to 82. FIG. 73 is a diagram showing an example selection screen displayed on the head-mounted display unit 1006 via the selection processing performed by a visual axis entry transmission apparatus according to the eighteenth embodiment of the present invention. FIG. 74 is a flowchart showing the selection processing performed by the visual axis entry transmission apparatus according to the eighteenth embodiment. FIG. 75 is a flowchart showing up arrow key selection processing at step S1602 in FIG. 74. FIG. 76 is a flowchart showing down arrow key selection processing at step S1604 in FIG. 74. FIG. 77 is a flowchart showing right arrow key selection processing at step S1606 in FIG. 74. FIG. 78 is a flowchart showing left arrow key selection processing at step S1608 in FIG. 74. FIG. 79 is a flowchart showing up-left arrow key selection processing at step S1610 in FIG. 74. FIG. 80 is a flowchart showing up-right arrow key selection processing at step S1612 in FIG. 74. FIG. 81 is a flowchart showing down-left arrow key selection processing at step S1614 in FIG. 74. FIG. 82 is a flowchart showing down-right arrow key selection processing at step S1616 in FIG. 74.

In this embodiment, options are selected by performing visual axis entries a plurality of times. Specifically, as is shown in FIG. 73, options are positioned in the center of the selection screen, and "↑", "↓", "←", "→", "↖", "↗", "↙", and "↘" arrows are positioned around the periphery. To move the selection frame to the location of a desired character, or to a desired option, the user selects one of the eight arrow keys by moving the visual axis to the screen location occupied by the key and performing the visual axis entry that satisfies the visual axis confirmation condition. Then, the character or the option inside the selection frame is selected and entered.

The selection processing using the selection screen will now be described while referring to FIG. 74. First, at step S1601 a check is performed to determine whether the visual axis is positioned at the "↑" key on the selection screen displayed on the head-mounted display unit 1006. When the visual axis is positioned at the "↑" key, program control moves to step S1602, whereat the up arrow key selection processing is performed. When the visual axis is not positioned at the "↑" key, program control moves to step S1603 and a check is performed to determine whether the visual axis is positioned at the "↓" key on the selection screen. When the visual axis is positioned at the "↓" key, program control moves to step S1604, whereat the down arrow key selection processing is performed. When the visual axis is not positioned at the "↓" key, program control moves to step S1605 and a check is performed to determine whether the visual axis is positioned at the "→" key on the selection screen. When the visual axis is positioned at the "→" key, program control moves to step S1606, whereat the right arrow key selection processing is performed. When the visual axis is not positioned at the "→" key, program control moves to step S1607 and a check is performed to determine whether the visual axis is positioned at the "←" key on the selection screen. When the visual axis is positioned at the "←" key, program control moves to step S1608, whereat the left arrow key selection processing is performed. When the visual axis is not positioned at the "←" key, program control moves to step S1609 and a check is performed to determine whether the visual axis is positioned at the "↖" key on the selection screen. When the visual axis is positioned at the "↖" key, program control moves to step S1610, whereat the up-left arrow key selection processing is performed. When the visual axis is not positioned at the "↖" key, program control moves to step S1611 and a check is performed to determine whether the visual axis is positioned at the "↗" key on the selection screen. When the visual axis is positioned at the "↗" key, program control moves to step S1612, whereat the up-right arrow key selection processing is performed. When the visual axis is not positioned at the "↗" key, program control moves to step S1613 and a check is performed to determine whether the visual axis is positioned at the "↙" key on the selection screen. When the visual axis is positioned at the "↙" key, program control moves to step S1614, whereat the down-left arrow key selection processing is performed. When the visual axis is not positioned at the "↙" key, program control moves to step S1615 and a check is performed to determine whether the visual axis is positioned at the "↘" key on the selection screen. When the visual axis is positioned at the "↘" key, program control moves to step S1616, whereat the down-right arrow key selection processing is performed. When the visual axis is not positioned at the "↘" key, it is assumed that the visual axis is not positioned at any of the arrow keys, and program control thereafter exits this processing sequence.

The up arrow key selection processing will now be described while referring to FIG. 75. In the up arrow key selection processing, first at step S2701 the value of an up arrow key selection frequency counter is incremented by one, and at step S2702 the other arrow key selection frequency counters are reset. At step S2703 a check is performed to determine whether the count value of the up arrow key selection frequency counter is equal to or greater than a preset value. When the value of the up arrow selection frequency counter is smaller than the preset value, program control exits this processing sequence. When the value of the up arrow selection frequency counter is equal to or greater than the preset value, at step S2705 a check is performed to determine whether the current vertical direction selection cell number is 0, i.e., whether the currently selected option is positioned at the topmost cell. If the currently selected choice is not located at the topmost cell, at step S2706 the vertical direction cell number is incremented by one, and program control advances to step S2707. When the currently selected option is located at the topmost cell, program control skips step S2706 and goes to step S2707.

At step S2707 the up arrow selection frequency counter is reset, and at step S2708 the screen is again displayed. Program control thereafter exits this processing sequence.

The down arrow key selection processing will now be described while referring to FIG. 76. In the down arrow key selection processing, first at step S2801 the value of a down arrow key selection frequency counter is incremented by one, and at step S2802 the other arrow key selection frequency counters are reset. At step S2803 a check is performed to determine whether the count value of the down arrow key selection frequency counter is equal to or greater than a preset value. When the value of the down arrow selection frequency counter is smaller than the preset value, program control exits this processing sequence. When the value of the down arrow selection frequency counter is equal to or greater than the preset value, at step S2805 a check is performed to determine whether the current vertical direction selection cell number is a maximum value, i.e., whether the currently selected option is positioned at the lowermost cell. If the currently selected choice is not located at the lowermost cell, at step S2806 the vertical direction cell number is decremented by one, and program control advances to step S2807. When the currently selected option is located at the lowermost cell, program control skips step S2806 and goes to step S2807.

At step S2807 the down arrow selection frequency counter is reset, and at step S2808 the screen is again displayed. Program control thereafter exits this processing sequence.

The right arrow key selection processing will now be described while referring to FIG. 77. In the right arrow key selection processing, first at step S1901 the value of a right arrow key selection frequency counter is incremented by one, and at step S1902 the other arrow key selection frequency counters are reset. At step S1903 a check is performed to determine whether the count value of the right arrow key selection frequency counter is equal to or greater than a preset value. When the value of the right arrow selection frequency counter is smaller than the preset value, program control exits this processing sequence. When the value of the right arrow selection frequency counter is equal to or greater than the preset value, at step S1905 a check is performed to determine whether the current horizontal direction selection cell number is a maximum value, i.e., whether the currently selected option is positioned at the rightmost cell. If the currently selected choice is not located at the rightmost cell, at step S1906 the horizontal direction cell number is incremented by one, and program control advances to step S1907. When the currently selected option is located at the rightmost cell, program control skips step S1906 and goes to step S1907.

At step S1907 the right arrow selection frequency counter is reset, and at step S1908 the screen is again displayed. Program control thereafter exits this processing sequence.

The left arrow key selection processing will now be described while referring to FIG. 78. In the left arrow key selection processing, first at step S2001 the value of a left arrow key selection frequency counter is incremented by one, and at step S2002 the other arrow key selection frequency counters are reset. At step S2003 a check is performed to determine whether the count value of the left arrow key selection frequency counter is equal to or greater than a preset value. When the value of the left arrow selection frequency counter is smaller than the preset value, program control exits this processing sequence. When the value of the left arrow selection frequency counter is equal to or greater than the preset value, at step S2005 a check is performed to determine whether the current horizontal direction selection cell number is 0, i.e., whether the currently selected option is positioned at the leftmost cell. If the currently selected choice is not located at the leftmost cell, at step S2006 the horizontal direction cell number is decremented by one, and program control advances to step S2007. When the currently selected option is located at the leftmost cell, program control skips step S2006 and goes to step S2007.

At step S2007 the left arrow selection frequency counter is reset, and at step S2008 the screen is again displayed. Program control thereafter exits this processing sequence.

The up-left arrow key selection processing will now be described while referring to FIG. 79. In the up-left arrow key selection processing, first at step S2101 the value of an up-left arrow key selection frequency counter is incremented by one, and at step S2102 the other arrow key selection frequency counters are reset. At step S2103 a check is performed to determine whether the count value of the up-left arrow key selection frequency counter is equal to or greater than a preset value. When the value of the up-left arrow selection frequency counter is smaller than the preset value, program control exits this processing sequence. When the value of the up-left arrow selection frequency counter is equal to or greater than the preset value, at step S2105 a check is performed to determine whether the current horizontal direction selection cell number is 0, i.e., whether the currently selected option is positioned at the leftmost cell. If the currently selected choice is not located at the leftmost cell, at step S2106 the horizontal direction cell number is decremented by one, and program control advances to step S2107. When the currently selected option is located at the leftmost cell, program control skips step S2106 and goes to step S2107.

At step S2107 a check is performed to determine whether the current vertical direction selection cell number is 0, i.e., whether the currently selected option is positioned at the topmost cell. If the currently selected choice is not located at the topmost cell, at step S2108 the vertical direction cell number is incremented by one, and program control advances to step S2109. When the currently selected option is located at the topmost cell, program control skips step S2108 and goes to step S2109.

At step S2109 the up-left arrow selection frequency counter is reset, and at step S2110 the screen is again displayed. Program control thereafter exits this processing sequence.

The up-right arrow key selection processing will now be described while referring to FIG. 80. In the up-right arrow key selection processing, first at step S2201 the value of an up-right arrow key selection frequency counter is incremented by one, and at step S2202 the other arrow key selection frequency counters are reset. At step S2203 a check is performed to determine whether the count value of the up-right arrow key selection frequency counter is equal to or greater than a preset value. When the value of the up-right arrow selection frequency counter is smaller than the preset value, program control exits this processing sequence. When the value of the up-right arrow selection frequency counter is equal to or greater than the preset value, at step S2205 a check is performed to determine whether the current horizontal direction selection cell number is a maximum value, i.e., whether the currently selected option is positioned at the rightmost cell. If the currently selected choice is not located at the rightmost cell, at step S2206 the horizontal direction cell number is incremented by one, and program control advances to step S2207. When the currently selected option is located at the rightmost cell, program control skips step S2206 and goes to step S2207.

At step S2207 a check is performed to determine whether the current vertical direction selection cell number is 0, i.e., whether the currently selected option is positioned at the topmost cell. If the currently selected choice is not located at the topmost cell, at step S2208 the vertical direction cell number is incremented by one, and program control advances to step S2209. When the currently selected option is located at the topmost cell, program control skips step S2208 and goes to step S2209.

At step S2209 the up-right arrow selection frequency counter is reset, and at step S2210 the screen is again displayed. Program control thereafter exits this processing sequence.

The down-left arrow key selection processing will now be described while referring to FIG. 81. In the down-left arrow key selection processing, first at step S2301 the value of a down-left arrow key selection frequency counter is incremented by one, and at step S2302 the other arrow key selection frequency counters are reset. At step S2303 a check is performed to determine whether the count value of the down-left arrow key selection frequency counter is equal to or greater than a preset value. When the value of the down-left arrow selection frequency counter is smaller than the preset value, program control exits this processing sequence. When the value of the down-left arrow selection frequency counter is equal to or greater than the preset value, at step S2305 a check is performed to determine whether the current horizontal direction selection cell number is 0, i.e., whether the currently selected option is positioned at the leftmost cell. If the currently selected choice is not located at the leftmost cell, at step S2306 the horizontal direction cell number is decremented by one, and program control advances to step S2307. When the currently selected option is located at the leftmost cell, program control skips step S2306 and goes to step S2307.

At step S2307 a check is performed to determine whether the current vertical direction selection cell number is a maximum value, i.e., whether the currently selected option is positioned at the lowermost cell. If the currently selected choice is not located at the lowermost cell, at step S2308 the vertical direction cell number is incremented by one, and program control advances to step S2309. When the currently selected option is located at the lowermost cell, program control skips step S2308 and goes to step S2309.

At step S2309 the down-left arrow selection frequency counter is reset, and at step S2310 the screen is again displayed. Program control thereafter exits this processing sequence.

The down-right arrow key selection processing will now be described while referring to FIG. 82. In the down-right arrow key selection processing, first at step S2401 the value of a down-right arrow key selection frequency counter is incremented by one, and at step S2402 the other arrow key selection frequency counters are reset. At step S2403 a check is performed to determine whether the count value of the down-right arrow key selection frequency counter is equal to or greater than a preset value. When the value of the down-right arrow selection frequency counter is smaller than the preset value, program control exits this processing sequence. When the value of the down-right arrow selection frequency counter is equal to or greater than the preset value, at step S2405 a check is performed to determine whether the current horizontal direction selection cell number is a maximum value, i.e., whether the currently selected option is positioned at the rightmost cell. If the currently selected choice is not located at the rightmost cell, at step S2406 the horizontal direction cell number is incremented by one, and program control advances to step S2407. When the currently selected option is located at the rightmost cell, program control skips step S2406 and goes to step S2407.

At step S2407 a check is performed to determine whether the current vertical direction selection cell number is a maximum value, i.e., whether the currently selected option is positioned at the lowermost cell. If the currently selected choice is not located at the lowermost cell, at step S2408 the vertical direction cell number is incremented by one, and program control advances to step S2409. When the currently selected option is located at the lowermost cell, program control skips step S2408 and goes to step S2409.

At step S2409 the down-right arrow selection frequency counter is reset, and at step S2410 the screen is again displayed. Program control thereafter exits this processing sequence.

As is described above, in this embodiment, by shifting the visual axis to select the eight arrow keys, a selection frame can be moved to a desired character or option, and the visual axis entry that satisfies the visual axis input confirmation condition can be performed. As a result, the character or the option at the selection frame can be selected and entered, so that a specific entry can be performed easily and certainly, and the operating environment that facilities the data input can be provided for the user.

(s) Nineteenth Embodiment

Figure 83:
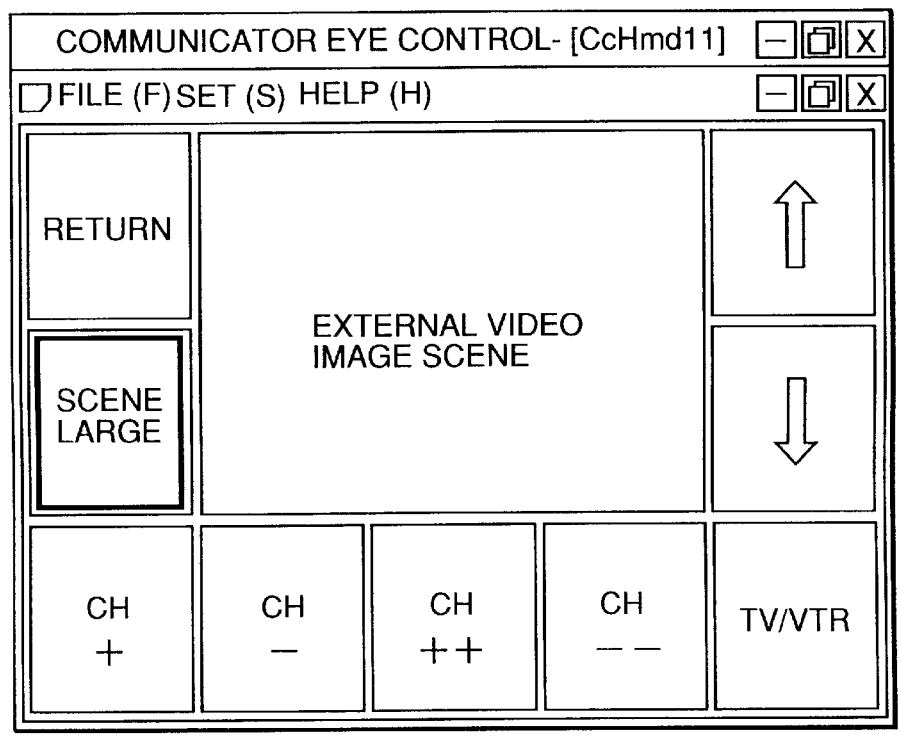
FIG. 83 is a diagram showing an example selection screen on the head-mounted display provided by the visual axis entry transmission apparatus according to a nineteenth embodiment of the present invention.
Figure 84:
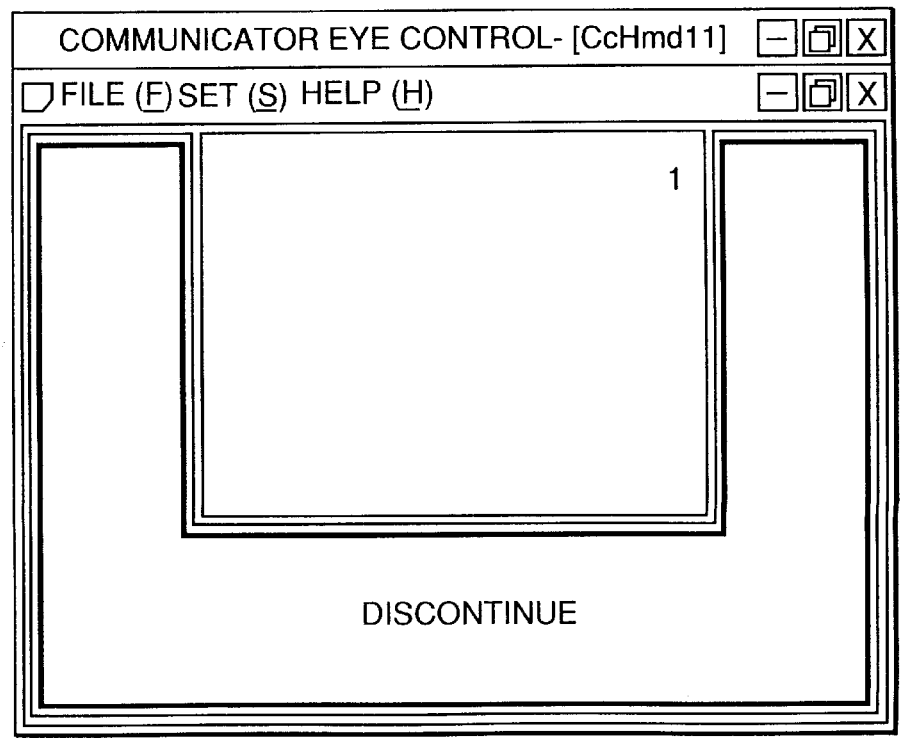
FIG. 84 is a diagram showing another example selection screen on the head-mounted display provided by the visual axis entry transmission apparatus according to the nineteenth embodiment of the present invention.
Figure 85:
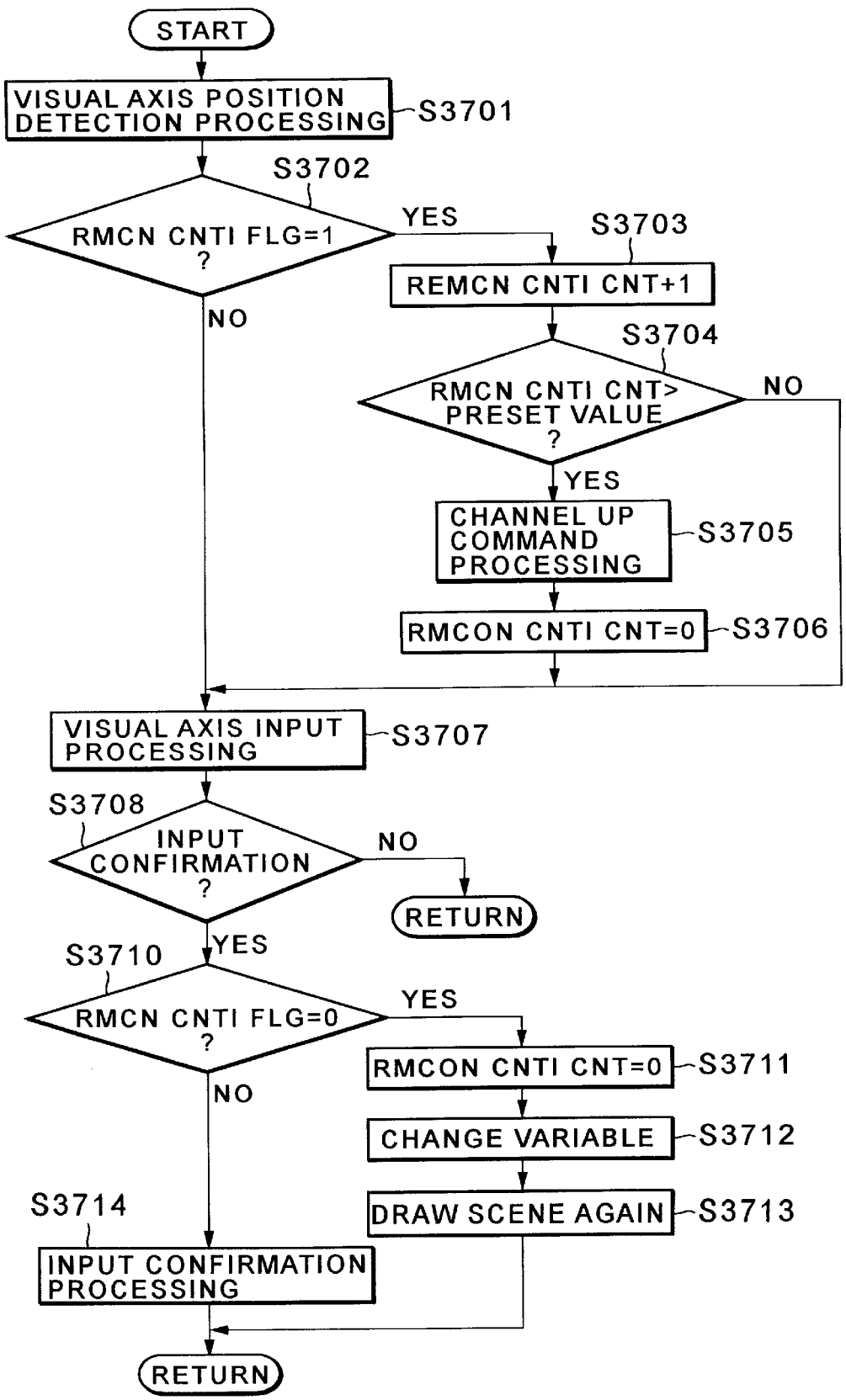
FIG. 85 is a flowchart showing the processing performed by the visual axis entry transmission apparatus according to the nineteenth embodiment of the present invention.

A nineteenth embodiment of the present invention will now be explained while referring to FIGS. 83 to 85. FIGS. 83 and 84 are diagrams showing example selection screens that are displayed on the head-mounted display unit 1006 of a visual axis entry transmission apparatus according to the nineteenth embodiment of the present invention. FIG. 85 is a flowchart showing the processing performed by the visual axis entry transmission apparatus according to the nineteenth embodiment.

In this embodiment, the personal computer 1008 includes an interface for connecting an external device so that it can be controlled, and performs a process whereby available options are displayed on the head-mounted display unit 1006 to sequentially vary the degree of control provided for the external device, and whereby when one of the options is selected by shifting the visual axis, a command generated by the personal computer 1008 to sequentially vary the degree of control can be output through the interface to the external device.

In this embodiment, an explanation will be given for an example wherein a television, for example, is connected to the apparatus and the options, as well as a television broadcast scene, are displayed on the head-mounted display unit 1006 for changing channels and adjusting the volume. Of these options, included is an option for instructing that the channels be sequentially changed, one by one.

Specifically, as is shown in FIG. 83, an external video image and options located around the periphery are displayed on the head-mounted display unit 1006. When option "CH++," which instructs the sequential changing of the channels, one by one, is selected by shifting the visual axis, upon receipt of this selection the personal computer 1008 sequentially outputs via the interface channel change commands to change the television channels one by one. Each time the channel change command is received, the television channel is switched. Further, as the option "CH++" was the one selected, the screen on the head-mounted display unit 1006 is changed to the screen shown in FIG. 84, on which an option is displayed to instruct at which channel the channel change sequence should be halted. When a desired channel is displayed on this screen, "Discontinue" is selected by using the visual axis. In response to this selection, the personal computer 1008 halts the output of the channel change command, so that the user can view the scene carried by the desired channel.

The above described processing will now be described while referring to FIG. 85. First, at step S3701 the visual axis detection process is performed. At step S3702 a check is performed to determine whether the value of flag RmcnCntFlg, which indicates that a command is being sequentially output to the television, is "1." When the value of the flag RmcnCntFlg is "1," it is assumed that the command is being sequentially output to the television, and program control moves to step S3703. At step S3703 the value of counter RmconCntiCnt, which serves as a timer for generating the output timing of the above command, is incremented by one. At step S3704 a check is performed to determine whether the value of the counter RmconCntiCnt exceeds a preset value. When the value of the counter RmconCntiCnt exceeds the preset value, program control advances to step S3705, whereat a process for outputting a command to advance the channel by one is performed. At step S3706 the counter RmconCntiCnt is reset, and program control then goes to step S3707. When the value of the counter RmconCntiCnt does not exceed the preset value, program control skips steps S3705 and S3706 and moves to step S3707.

At step S3707 the visual axis entry process is performed. At step S3708 a check is performed to determine whether the entry has been confirmed. When the entry has is been confirmed, program control exits this processing sequence.

When the entry has been confirmed, at step S3710 a check is performed to determine the value of the flag RmcnCntFlg is 0. When the value of the flag RmcnCntFlg is 0, program control goes to step S3711, whereat the counter RmconCntiCnt is reset. Following this, at step S3712 a variable is changed for setting the display area ratio of the external video image to the option on the head-mounted display unit 1006. At step S3713 the screen is again displayed based on the new variable setting, and program control thereafter exits this processing sequence. When the value of the flag RmcnCntFlg is not 0, program control moves to step S3714, whereat the input confirmation process is performed. Program control thereafter exits this processing sequence.

When, at step S3702, the value of the flag RmcnCntFlg is not 1, program control moves to step S3707, and the above described process is thereafter performed.

As is described above, in this embodiment, the degree of control provided for the external device can be sequentially changed by employing the visual axis.

In this embodiment, an example for sequentially changing the channel of the television is employed. However, control can also be provided for sequentially changing other functions, such as volume.

(t) Twentieth Embodiment

Figure 86:
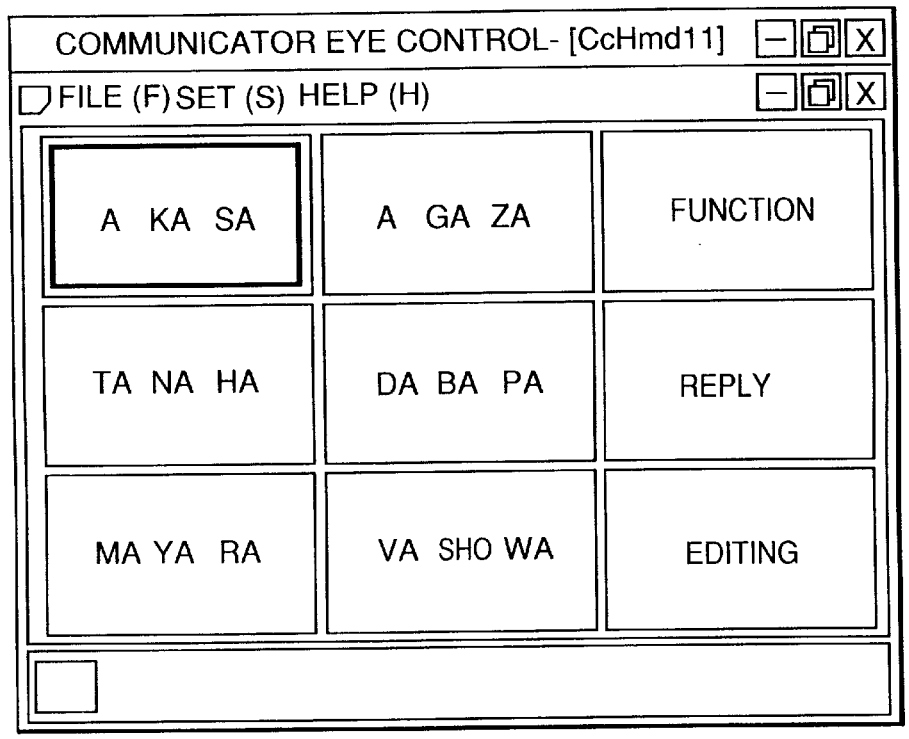
FIG. 86 is a diagram showing an example selection screen on the head-mounted display provided by the visual axis entry transmission apparatus according to a twentieth embodiment of the present invention.
Figure 87:
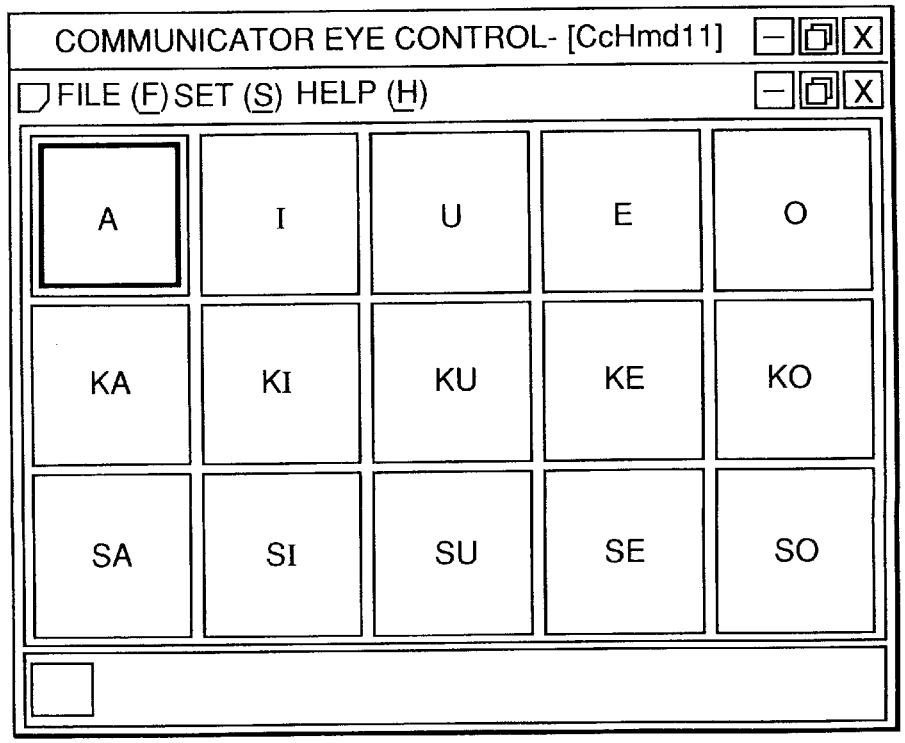
FIG. 87 is a diagram showing another example selection screen on the head-mounted display provided by the visual axis entry transmission apparatus according to the twentieth embodiment of the present invention.

A twentieth embodiment according to the present invention will now be described while referring to FIGS. 86 and 87. FIGS. 86 and 87 are diagrams showing example selection screens displayed on the head-mounted display unit 1006 of a visual axis entry transmission apparatus according to the twentieth embodiment of the present invention.

In this embodiment, options are displayed as layers on the head-mounted display unit 1006. An option to be input is selected by employing the visual axis to trace in order the options that are located below an option that has been selected.

In this embodiment, as is shown in FIG. 86, options, such as "A KA SA", "TA NA HA" and "MA YA RA", are displayed on the first selection screen. "A KA SA" is an option that provides a group of hiragana characters in columns headed by "A", "KA" and "SA". Similarly, "TA NA HA" is an option that provides a group of hiragana characters in columns headed by "TA", "NA" and "HA", and "MA YA RA" is a option that provides a group of hiragana characters in columns headed by "MA", "YA" and "RA". "Function" is a function for selecting, as a group, a remote control function, a hiragana/katakana/alphanumeric character mode switching function, a registration function, a fixed sentence calling function, and a setup change function.

When for example, on this screen "A KA SA" is selected and entered using the visual axis, the screen is changed to the individual character selection screen in FIG. 87. The individual character selection screen is used to select individual hiragana characters from the columns headed by "A", "KA" and "SA". When, for example, on the screen "A" is selected and selected by using the visual axis, "A" is displayed in the sentence display portion across the bottom of the screen.

When another option is selected on the first selection screen, the screen is changed to another individual selection screen for the selection of individual options from the selected group. If a group of options is further included in the selected option group on the individual item selection screen, the user can sequentially trace options that are located below the selected option to select the individual option to be included in the group, and by employing the visual axis can display a pertinent selection screen.

Options to be grouped under one option can be set arbitrarily. In this case, a process need only be performed whereby the options for forming a group are selected in advance in accordance with the instructions of a user, and the layers of the grouped options are traced in order.

As is described above, according to this embodiment, a plurality of options are grouped together under one option, that option is selected by selecting the options included therein, and a corresponding option is then selected from among the multiple options. That is, the visual axis is employed while the selection options located below the first selected option are traced in order, and a specific option is selected and established. Therefore, multiple selection options need not be displayed at one time, and the area for each option displayed can be larger than that when multiple options are displayed at the same time. As a result, the user can easily focus the visual axis on a desired option, and the occurrence of selection errors can be reduced.

(u) Twenty-first Embodiment

Figure 88:
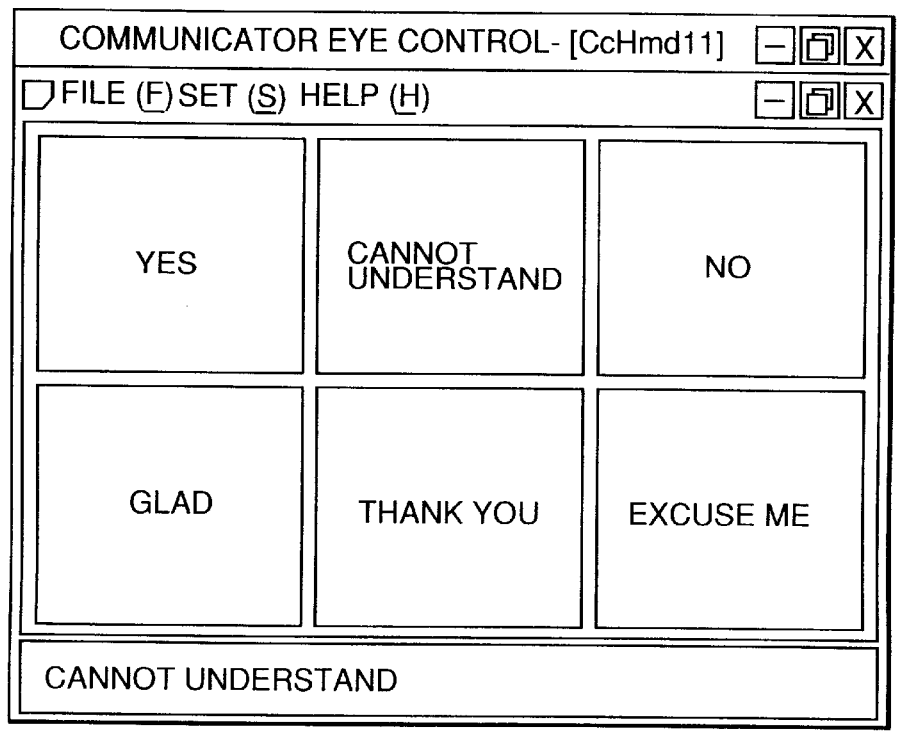
FIG. 88 is a diagram showing an example selection screen on the head-mounted display provided by the visual axis entry transmission apparatus according to a twenty-first embodiment of the present invention.
Figure 89:
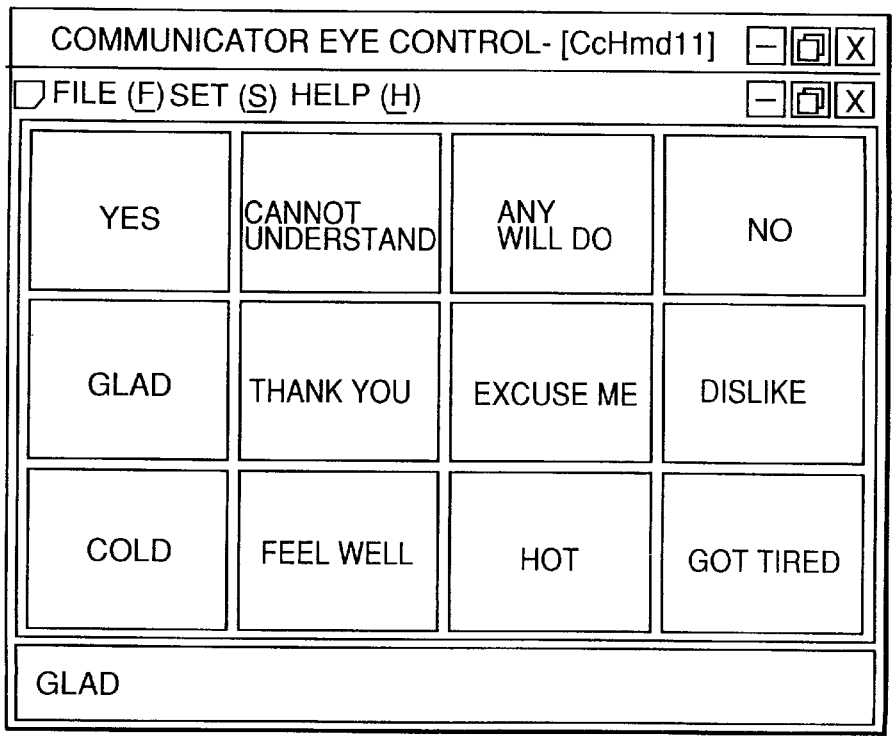
FIG. 89 is a diagram showing another example selection screen on the head-mounted display provided by the visual axis entry transmission apparatus according to the twenty-first embodiment of the present invention.

A twenty-first embodiment according to the present invention will now be explained while referring to FIGS. 88 and 89. FIGS. 88 and 89 are diagrams showing example selection screens displayed on the head-mounted display unit 1006 of a visual axis entry transmission apparatus according to the twenty-first embodiment of the present invention.

In this embodiment, provided is a mode in which a plurality of words that are prepared in advance are displayed for selection purposes on the head-mounted display unit 1006, and in which a desired word is selected by employing the visual axis.

In this embodiment, as is shown in FIG. 88, words or phrases, such as "Yes", "No" and "Thank you", are displayed that are frequently employed as responses. Therefore, as a response to a query by a user, "Yes" or "No" can be selected with one visual axis entry, and a quick response is possible, without an operation for sequentially inputting characters, such as "HA" and "I", being required. In addition, this selection screen can be employed as a screen for training in how to employ the visual axis for entries.

Furthermore, as is shown in FIG. 89 a greater variety of responses can be provided by displaying more words or phrases than those on the above screen.

As is described above, according to the eleventh to the twenty-first embodiments, the user can confirm the result of the detection of the visual axis, and does not have to uselessly repeat operations.

Furthermore, the user can monitor an external video image while viewing the display panel.

In addition, the user can view a screen having a desired display condition.

Further, the user can select an option by using the visual axis, while viewing an externally input video image.

Moreover, the options on the display panel can be displayed so that a user can easily identify them.

Also, the degree of control provided for an external device can be sequentially changed.

Then too, a predetermined entry is easily ensured, and an operating environment can be provided that facilitates an input operation by a user.

Further, the user can set a desired layer structure for options.

The present invention can be applied to a system that is constituted by a plurality of devices, or to an apparatus that includes a single device. The present invention can also be applied by supplying a program to a system or to an apparatus. In this case, the effects of the present invention can be provided by adding to the system or to the apparatus a memory medium in which is stored a program that constitutes a software application for implementing the present invention.

In the above embodiments, a ROM is employed as a memory medium. However, the memory medium is not limited to a ROM and can be, for example, a floppy disk, a hard disk, an optical disk, a magneto optical disk, a CD-ROM, a CD-R, a DVD, a magnetic tape or a nonvolatile memory card.

What is claimed is:

1. A visual line detecting apparatus comprising:
    display means for displaying a plurality of icons on a display panel;
    visual line detection means for detecting a visual line of a user facing said display panel;
    determination means for determining an icon corresponding to a position of the visual line of the user detected by said visual line detection means;
    external image input means for receiving an external image signal; and
    display control means for controlling said display means so as to display an external image corresponding to the external image signal received by said external image input means, wherein, when the external image is displayed by said display means, said display control means is capable of controlling said display means so as to display, overlapping each other, the external image and the icon corresponding to the position of the visual line of the user determined by said determination means.

2. An apparatus according to claim 1, further comprising:
    head position detection means for detecting a head position of the user; and
    compensation means for compensating the position of the visual line that is detected by said visual line detection means.

3. An apparatus according to claim 1,
    wherein said display means includes projection means for projecting a video image on said display panel.

4. An apparatus according to claim 3, wherein said video image includes said plurality of icons.

5. An apparatus according to claim 3, wherein, when the visual line is positioned on the same icon or video image for a predetermined period of time or longer, said determination means determines that the icon or video image has been selected.

6. An apparatus according to claim 5, further comprising change means for, upon receipt of an instruction by the user, changing the predetermined period of time required to determine that a video image is selected.

7. An apparatus according to claim 3, wherein, when the visual line is positioned on an icon or video image and the user closes his or her eyes for a predetermined period of time, said determination means determines that the icon or video image has been selected.

8. An apparatus according to claim 7, further comprising change means for, upon receiving an instruction from the user, changing the predetermined period of time the eyes of the user must remain closed before a video image to be selected is determined.

9. An apparatus according to claim 3, wherein, when the visual line is positioned on an icon or video image and the user depresses and holds a switch for a predetermined period of time, said determination means determines that the icon or video image has been selected.

10. An apparatus according to claim 9, further comprising change means for, upon receiving an instruction from the user, changing the predetermined period of time said switch must be depressed and held before a video image to be selected is determined.

11. An apparatus according to claim 10, further comprising change means for changing the specific ratio upon receiving an instruction from the user.

12. An apparatus according to claim 3, wherein said determination means includes:
    means for identifying an icon or video image when the visual line is positioned on the same icon or video image for a predetermined period of time or longer;
    means for identifying an icon or video image when the visual line is positioned on the icon or video image and the user's eyes are closed and held closed for a predetermined period of time;
    means for identifying an icon or video image when the visual line is positioned on the icon or video image and the user depresses and holds a switch for a predetermined period of time; and
    switching means for changing the one of said identifying means for determining an icon or video image has been selected.

13. An apparatus according to claim 4, further comprising change means for, upon receipt of an instruction by the user, changing the predetermined period of time required to determine that an icon or video image is selected.

14. An apparatus according to claim 3, wherein, when the visual line is positioned on the same icon or video image at a specific ratio for a predetermined period of time, said determination means identifies the icon or video image to be selected.

15. An apparatus according to claim 14, further comprising change means for changing the specific ratio upon receiving an instruction from the user.

16. An apparatus according to claim 3, further comprising change means for changing the number of icons or video images included in said display panel upon receiving an instruction from the user.

17. An apparatus according to claim 3, further comprising switching means for, upon receiving an instruction from the user, switching an icon or video image on said display panel and an external image.

18. An apparatus according to claim 17, wherein the external image is a video image received from a television, a video recorder, a computer, a video-on-demand device, a clock, a crime prevention device or a video telephone.

19. An apparatus according to claim 18, wherein said external environment device is a lighting apparatus, a television, an audio device, a video recorder, a computer, a video-on-demand device, a telephone, a video telephone, a clock, an electric blind, an electric curtain, an electric window opening/closing device, an air conditioner, a crime prevention device, an electric reclining bed, a device for handling body excretions, a lifter or a nurse calling device.

20. An apparatus according to claim 17, further comprising operation means for operating an external environment device upon receiving an instruction from the user.

21. An apparatus according to claim 3, further comprising visibility adjustment means for adjusting visibility of the video image or the plurality of icons on said display panel.

22. An apparatus according to claim 3, further comprising deletion means for deleting an icon or video image on said display panel.

23. An apparatus according to claim 22, further comprising switching means for, upon receiving an instruction from the user, switching the display or deleting a video image on said display panel.

24. An apparatus according to claim 23, further comprising change means for changing said predetermined period of time that the eyes of the user must be held closed.

25. An apparatus according to claim 3, further comprising printing means for performing printing in accordance with an icon or video image selected by using the visual line.

26. An apparatus according to claim 25, wherein paper is not discharged each time printing is performed.

27. An apparatus according to one of claims 1 and 2, wherein, when the visual line is positioned on the same icon for a predetermined period of time or longer, said determination means determines that the icon has been selected.

28. An apparatus according to claim 27, further comprising change means for, upon receipt of an instruction by the user, changing the predetermined period of time required to determine that an icon is selected.

29. An apparatus according to one of claims 1 and 2, wherein, when the visual line is positioned on an icon and the user closes his or her eyes for a predetermined period of time, said determination means determines that the icon has been selected.

30. An apparatus according to claim 29, further comprising change means for, upon receiving an instruction from the user, changing the predetermined period of time the eyes of the user must remain closed before an icon to be selected is determined.

31. An apparatus according to one of claims 1 and 2, wherein, when the visual line is positioned on an icon and the user depresses and holds a switch for a predetermined period of time, said determination means determines that the icon has been selected.

32. An apparatus according to claim 31, further comprising change means for, upon receiving an instruction from the user, changing the predetermined period of time said switch must be depressed and held before an icon to be selected is determined.

33. An apparatus according to one of claims 1 and 2, wherein said determination means includes:
   means for identifying an icon when the visual line is positioned on the same icon for a predetermined period of time or longer;
   means for identifying an icon when the visual line is positioned on the icon and the user's eyes are closed and held closed for a predetermined period of time;
   means for identifying an icon when the visual line is positioned on the icon and the user depresses and holds a switch for a predetermined period of time; and
   switching means for changing the one of said identifying means for determining that an icon has been selected.

34. An apparatus according to one of claims 1 and 2, wherein, when the visual line is positioned on the same icon at a specific ratio for a predetermined period of time, said determination means identifies the icon to be selected.

35. An apparatus according to claim 34, further comprising change means for changing the specific ratio upon receiving an instruction from the user.

36. An apparatus according to one of claims 1 and 2, further comprising change means for changing the number of icons included in said display panel upon receiving an instruction from the user.

37. An apparatus according to one of claims 1 and 2, further comprising switching means for, upon receiving an instruction from the user, switching an icon on said display panel and an external image.

38. An apparatus according to claim 37, wherein the external image is a video image received from a television, a video recorder, a computer, a video-on-demand device, a clock, a crime prevention device or a video telephone.

39. An apparatus according to claim 37, further comprising operation means for operating an external environment device upon receiving an instruction from the user.

40. An apparatus according to claim 39, wherein said external environment device is a lighting apparatus, a television, an audio device, a video recorder, a computer, a video-on-demand device, a telephone, a video telephone, a clock, an electric blind, an electric curtain, an electric window opening/closing device, an air conditioner, a crime prevention device, an electric reclining bed, a device for handling body excretions, a lifter or a nurse calling device.

41. An apparatus according to claim 1, further comprising visibility adjustment means for adjusting visibility of the plurality of icons on said display panel.

42. An apparatus according to one of claims 1 and 2, further comprising deletion means for deleting an icon on said display panel.

43. An apparatus according to claim 42, further comprising switching means for, upon receiving an instruction from the user, switching the display or deleting the icon on said display panel.

44. An apparatus according to claim 43, wherein said deletion means deletes the icon on said display panel when the eyes of the user have been closed for a predetermined period of time.

45. An apparatus according to claim 44, further comprising change means for changing said predetermined period of time that the eyes of the user must be held closed.

46. An apparatus according to claim 43, wherein said deletion means deletes the icon on said display panel when the user sets the visual line along a predetermined direction line.

47. An apparatus according to claim 46, further comprising change means for changing said predetermined direction line along which the user sets the visual line.

48. An apparatus according to one of claims 1 and 3 to 5, further comprising area restriction means for restricting an area to which entry by the visual line is permissible.

49. An apparatus according to claim 48, further comprising switching means for, upon receiving an instruction from the user, determining whether the area to which entry by the visual line is permissible is to be restricted.

50. An apparatus according to claim 49, further comprising change means for, upon receiving an instruction from the user, changing the area to which entry by the visual line is permissible.

51. An apparatus according to claim 48, wherein the area to which entry by the visual line is permissible is restricted after the eyes of the user have been closed for a predetermined period of time.

52. An apparatus according to claims 51, further comprising change means for changing the predetermined period of time that the eyes of the user must remain closed.

53. An apparatus according to claim 48, wherein the area to which entry by the visual line is permissible is restricted by the user setting the visual line along a predetermined direction line.

54. An apparatus according to claim 53, further comprising change means for changing the predetermined direction line along which the user sets the visual line.

55. An apparatus according to claim 48, wherein the position of the visual line is not displayed in the area to which entry by the visual line is restricted.

56. An apparatus according to claim 48, further comprising change means for, upon receiving an instruction from the user, changing a setup that establishes whether the position of the visual line is to be displayed in the area to which entry by the visual line is restricted.

57. An apparatus according to one of claims 1 or 3 to 5, further comprising change means for changing the size of said display panel to be displayed.

58. An apparatus according to claim 57, further comprising change means for, upon receiving an instruction from the user, changing the size of said display panel.

59. An apparatus according to one of claims 1 or 3 to 5, further comprising change means for employing the visual line to change a cursor position in a sentence display portion that is displayed.

60. An apparatus according to claim 59, further comprising switching means for, upon receiving an instruction from the user, switching a setup that establishes whether the cursor position is to be changed using the visual line.

61. An apparatus according to one of claims 1 or 3 to 5, wherein, after an entry by the visual line has been established, another entry using the visual line is not accepted for a predetermined period of time.

62. An apparatus according to claim 61, further comprising change means for changing the predetermined period of time during which, after an entry by the visual line has been established, another entry using the visual line is not accepted.

63. An apparatus according to one of claims 1 and 2, further comprising printing means for performing printing in accordance with an icon selected by using the visual line.

64. An apparatus according to claim 63, wherein paper is not discharged each time printing is performed.

65. An apparatus according to claim 64, further comprising change means for, upon receiving an instruction from the user, changing a setup that establishes whether paper is to be discharged each time printing is permitted.

66. A visual line detecting apparatus comprising:
projection means for projecting a video image on a display screen;
visual line detection means for detecting a visual line of a user facing said display screen;
head position detection means for detecting a head position of the user;
compensation means for compensating a position of the visual line detected by said visual line detection means;
determination means for determining a video image on said display screen which the user is viewing, on the basis of a visual line position compensated by said compensation means;
external image input means for receiving an external image signal; and
display control means for controlling said projection means so as to project an external image corresponding to the external image signal received by said external image input means, wherein, when the external image is projected by said projection means, said display control means is capable of controlling said projection means so as to project, overlapping each other, the external image and the video image determined by said determination means.

67. An apparatus according to claim 66, wherein, when the visual line is positioned on the same video image for a predetermined period of time or longer, said determination means determines that the video image has been selected.

68. An apparatus according to claim 67, further comprising change means for, upon receiving an instruction from the user, changing the predetermined period of time the eyes of the user must remain closed before an icon or video image to be selected is determined.

69. An apparatus according to claim 66, wherein, when the visual line is positioned on a video image and the user closes his or her eyes for a predetermined period of time, said determination means determines that the video image has been selected.

70. An apparatus according to claim 69, further comprising change means for, upon receiving an instruction from the user, changing the predetermined period of time said switch must be depressed and held before an icon or video image to be selected is determined.

71. An apparatus according to claim 66, wherein, when the visual line is positioned on a video image and the user depresses and holds a switch for a predetermined period of time, said determination means determines that the video image has been selected.

72. An apparatus according to claim 66, wherein said determination means includes:
means for identifying a video image when the visual line is positioned on the same video image for a predetermined period of time or longer;
means for identifying a video image when the visual line is positioned on the video image and the user's eyes are closed and held closed for a predetermined period of time;
means for identifying a video image when the visual line is positioned on the video image and the user depresses and holds a switch for a predetermined period of time; and
switching means for changing the one of said identifying means for determining a video image has been selected.

73. An apparatus according to claim 66, wherein, when the visual line is positioned on the same video image at a specific ratio for a predetermined period of time, said determination means identifies the video image to be selected.

74. An apparatus according to claim 66, further comprising change means for changing the number of video images included in said display panel upon receiving an instruction from the user.

75. An apparatus according to claim 74, wherein the external image is a video image received from a television, a video recorder, a computer, a video-on-demand device, a clock, a crime prevention device or a video telephone.

76. An apparatus according to claim 74, further comprising operation means for operating an external environment device upon receiving an instruction from the user.

77. An apparatus according to claim 76, wherein said external environment device is a lighting apparatus, a television, an audio device, a video recorder, a computer, a video-on-demand device, a telephone, a video telephone, a clock, an electric blind, an electric curtain, an electric window opening/closing device, an air conditioner, a crime prevention device, an electric reclining bed, a device for handling body excretions, a lifter or a nurse calling device.

78. An apparatus according to claim 66, further comprising switching means for, upon receiving an instruction from the user, switching a video image on said display panel and an external image.

79. An apparatus according to claim 66, further comprising visibility adjustment means for adjusting visibility of the video image on said display panel.

80. An apparatus according to claim 79, further comprising switching means for, upon receiving an instruction from the user, switching the display or deleting an icon or video image on said display panel.

81. An apparatus according to claim 80, wherein said deletion means deletes the video image on said display panel when the eyes of the user have been closed for a predetermined period of time.

82. An apparatus according to claim 80, wherein said deletion means deletes the video image on said display panel when the user sets the visual line along a predetermined direction line.

83. An apparatus according to claim 66, further comprising deletion means for deleting a video image on said display panel.

84. An apparatus according to claim 83, wherein said deletion means deletes the icon or video image on said display panel when the eyes of the user have been closed for a predetermined period of time.

85. An apparatus according to claim 84, further comprising change means for changing said predetermined period of time that the eyes of the user must be held closed.

86. An apparatus according to claim 85, further comprising change means for changing said predetermined direction line along which the user sets the visual line.

87. An apparatus according to claim 83, wherein said deletion means deletes the icon or video image on said display panel when the user sets the visual line along a predetermined direction line.

88. An apparatus according to claim 87, further comprising change means for changing said predetermined direction line along which the user sets the visual line.

89. An apparatus according to claim 88, wherein paper is not discharged each time printing is performed.

90. An apparatus according to claim 89, further comprising change means for, upon receiving an instruction from the user, changing a setup that establishes whether paper is to be discharged each time printing is permitted.

91. An apparatus according to claim 66, further comprising printing means for performing printing in accordance with a video image selected by using the visual line.

92. An apparatus according to claim 91, further comprising change means for, upon receiving an instruction from the user, changing a setup that establishes whether paper is to be discharged each time printing is permitted.

93. A visual line detecting method comprising the steps of:
   displaying a plurality of icons on a display panel;
   detecting a visual line of a user facing the display panel;
   determining an icon corresponding to a position of the visual line detected in said detecting step;
   receiving an external image signal input externally; and
   controlling the display panel so as to display, overlapping each other, an external image corresponding to the external image signal externally input in said receiving step and the icon that is determined by the visual line of the user.

94. A memory medium on which is stored a program to be executed by a computer in a visual line detecting apparatus for detecting the intent of a user in accordance with the visual line, said program including the procedures of:
   displaying a plurality of icons on a display panel;
   detecting the visual line of the user facing the display panel;
   determining an icon corresponding to a position of the visual line detected in said detecting step;
   receiving an external image signal input externally; and
   controlling the display panel so as to display, overlapping each other, an external image corresponding to the external image signal externally input in said receiving step and the icon that is determined by the visual line of the user.

95. A visual line detecting apparatus comprising:
   image observation means for displaying a display panel that is easy for a user to see;
   external image input means for receiving an external video image;
   visual line detection means for detecting a visual line of the user facing said display panel displayed by said image observation means;
   visual line entry means for entering the visual line of the user, which is detected by said visual line detection means, as input information for display by said image observation means on said display panel, and for employing the input information to transmit the intent of the user; and
   display control means for permitting said image observation means to arrange in parallel said display panel and the external video image.

96. An apparatus according to claim 95, wherein said image observation means has one screen on which said display panel and the external video image is capable of being displayed in parallel, and wherein, upon receiving an instruction from the user, said display control means sets an arbitrary display area ratio of said display panel to the external video image on said screen of said image observation means.

97. A visual line detecting apparatus comprising:
   image observation means for displaying a video image that is easy for a user to see;
   visual line detection means for entering a visual line of the user, which is detected by said visual line detection means, as input information for the video image that is displayed by said image observation means, and for employing the input information to transmit the intent of the user;
   external video image entry means for receiving an external video image; and
   display control means for controlling said image observation means so as to display the external video image received by said external video image entry means,
   wherein, when the external video image is displayed by said image observation means, said display control means is capable of controlling said image observation means so as to display, overlapping each other, the external video image and an icon that is selected by the visual line of the user.

98. An apparatus according to claim 97, further comprising selection means for, upon receiving an instruction from the user, determining whether the icon displayed by said image observation means is to overlap the external video image.

99. A visual line detecting apparatus comprising:
   image observation means for so displaying a display panel in which icons are included that a user easily sees said icons;
   visual line detection means for detecting a visual line of the user facing said display panel displayed by said image observation means;
   visual line entry means for entering, as input information for said display panel, the visual line of the user that is detected by said visual line detection means, and for employing the input information to transmit an intent of the user;

external image input means for receiving an external video image; and display control means for controlling said image observation means so as to display, overlapping each other, the icons and the externally input video image, and changing a display form of the icons displayed by said image observation means on said display panel, upon receiving an instruction from the user.

100. An apparatus according to claim 99, wherein, upon receiving an instruction from the user, said display control means changes the background color of an icon displayed on said display panel.

101. An apparatus according to claim 99, wherein, upon receiving an instruction from the user, said display control means changes the character color of an icon on said display panel.

102. A visual line detecting apparatus comprising:

visual line entry means for detecting a visual line of a user facing a display panel, and for entering the result of the detection of the visual line of the user as information input to said display panel to transmit an intent of the user in accordance with the input information, connection means for connecting an external device to said visual line entry means;

display control means for controlling the display, on said display panel, of one or more icons corresponding to said external device; and output means for, when the input information that is transmitted by said visual line entry means reflects an intent of the user to sequentially vary the control degree of the one or more icons, sequentially outputting a command through said connection means to said external device so as to sequentially vary the control degree of the one or more icons.

103. A visual line detecting apparatus comprising:

visual line entry means for detecting a visual line of a user facing a display panel, and for entering the result of the detection of the visual line of the user as information input to said display panel to transmit an intent of the user in accordance with the input information; and display control means for controlling the display of one or more icons in layers on said display panel, wherein, while the icons that are located below a selected icon are traced in order, the input information is entered from said visual line entry means in the order of display of the icons, thereby enabling a mode in which said user is capable of establishing a specific intent.

104. An apparatus according to claim 103, wherein an arbitrary layer structure for the icons is set by the user.

105. A visual line detecting method comprising the steps of:

employing image observation means to display a display panel a user easily sees;

detecting a visual line of the user facing the display panel that is displayed by said image observation means;

entering the visual line of the user as input information for the display panel, and employing the input information to transmit an intent of the user;

receiving an external video image; and controlling said image observation means, by a display control means, so as to display the external video image in parallel with the display panel.

106. A method according to claim 105, whereby said image observation means has one screen on which the display panel and the external video image are displayed in parallel, and whereby, upon receiving an instruction from the user, said display control means sets an arbitrary display area ratio of the display panel to the external video image on the screen of said image observation means.

107. A visual line detecting method comprising the steps of:

displaying, using image observation means, a video image that is easy for a user to see;

detecting a visual line of the user facing the video image displayed by said image observation means;

entering the visual line of the user as input information for the video image that is displayed by said image observation means;

employing the input information to transmit an intent of the user;

receiving an external video image;

controlling said image observation means so as to display the external video image; and displaying the external video image by said image observation means, so that the external video image and the video image that is selected by the visual line of the user overlap each other.

108. A method according to claim 107, further comprising the step of, upon receiving an instruction from the user, determining whether the video image displayed by said image observation means is to overlap the external video image.

109. A visual line detecting method comprising the steps of:

displaying, using image observation means, a display panel in which icons are included so that a user easily sees the icons;

detecting a visual line of the user facing the display panel displayed by said image observation means;

entering the visual line of the user as input information for the display panel that is displayed by said image observation means, and employing the input information to transmit an intent of the user;

receiving an external video image; and controlling said image observation means so as to display, overlapping each other, the icons and the external video image, and to change a display form for the icons on the display panel upon receiving an instruction from the user.

110. A method according to claim 109, whereby, upon receiving an instruction from the user, the background color for an icon displayed on the display panel is changed.

111. A method according to claim 109, whereby, upon receiving an instruction from the user, the character color of an icon on the display panel is changed.

112. A visual line detecting method comprising the steps of:

detecting a visual line of a user facing a display panel;

entering the result of the detection of the visual line of the user as information input to the display panel to transmit an intent of the user in accordance with the input information;

connecting an external device to a visual line entry transmission apparatus through connection means;

displaying, on the display panel, icons for the external device; and sequentially outputting, when the transmitted input information reflects an intent of the user to sequentially vary the control degree of the icon a command through said connection means to the external device so as to sequentially vary the control degree.

113. A visual line detecting method comprising the steps of:
   detecting a visual line of a user facing a display panel;
   entering the result of the detection of the visual line of the user as information input to the display panel to transmit an intent of the user in accordance with the input information;
   displaying options in layers on the display panel; and
   while icons that are located below a selected icon are traced in order, entering the input information in the order of the display of the icons, thereby enabling a mode in which the user is capable of establishing a specific intent.

114. A method according to claim 113, whereby an arbitrary layer structure for the icons is set by the user.

115. A memory medium storing a computer readable program for controlling a visual line detecting method, said program comprising the steps of:
   employing image observation means to display a display panel that a user easily sees;
   detecting a visual line of the user facing the display panel that is displayed by said image observation means;
   entering the visual line of the user as input information for the display panel that is displayed by said image observation means, and employing the input information to transmit an intent of the user;
   receiving an external video image; and
   controlling said image observation means to display the external video image in parallel with the display panel.

116. A memory medium according to claim 115, wherein said image observation means has one screen on which the display panel and the external video image are capable of being displayed in parallel, and wherein, upon receiving an instruction from the user, said display control step sets an arbitrary display area ratio of the display panel to the external video image on the screen of said image observation means.

117. A memory medium on which is stored a program for building a visual line entry transmission system, which comprises:
   image observation means for displaying a video image that is easy for a user to see;
   visual line detection means for detecting a visual line of the user facing the video image displayed by said image observation means; and
   visual line entry means for entering the visual line of the user, which is detected by said visual line detection means, as input information for the video image that is displayed by said image observation means, and for employing the input information to transmit an intent of the user, said program including:
      an external video image entry module for receiving an external video image; and
      a display control module for controlling said image observation means so as to display the external video image received by said external video image entry module,
      wherein, when the external video image is displayed by said image observation means, said display control module displays, overlapping each other, the external video image and an icon that is selected by the visual line of the user.

118. A memory medium according to claim 117, wherein said program further comprises a selection module for, upon receiving an instruction from the user, determining whether the icon displayed by said image observation means is to overlap the external video image.

119. A memory medium storing a computer readable program for controlling a visual line detecting method, said program comprising the steps of:
   employing image observation means to display a display panel in which icons are included such that a user easily sees the icons;
   detecting a visual line of the user facing the display panel that is displayed by said image observation means;
   entering the visual line of the user as input information for the display panel that is displayed by said image observation means, and employing the input information to transmit an intent of the user;
   receiving an external video image; and
   controlling the display of the icons and the external video image so that they overlap each other, and so that a change of a display form of the icons on the display panel can be made upon receiving an instruction from the user.

120. A memory medium according to claim 119, wherein, upon receiving an instruction from the user, said display control step changes the background color of an icon displayed on the display panel.

121. A memory medium according to claim 119, wherein, upon receiving an instruction from the user, said display control step changes the character color of an icon on the display panel.

122. A memory medium on which is stored a program for building a visual line entry transmission system, which comprises:
   visual line entry means for detecting a visual line of a user facing a display panel, and for entering the result of the detection of the visual line of the user as information input to said display panel to transmit an intent of the user in accordance with the input information, said program including:
      a display control module for displaying, on said display panel, icons for an external device that is connected to said visual line entry transmission system through connection means; and
      an output module for, when input information reflects an intent of the user to sequentially vary the control degree of the icon, sequentially outputting a command through said connection means to the external device so as to sequentially vary the control degree of the icon.

123. A memory medium on which is stored a program for building a visual line entry transmission system, which comprises:
   visual line entry means for detecting a visual line of a user facing a display panel, and for entering the result of the detection of the visual line of the user as information input to said display panel to transmit an intent of the user in accordance with the input information, said program including:
      a display control module for displaying icons in layers on said display panel; and
      a mode execution module for, while icons that are located below a selected icon are traced in order, entering the input information from said visual line entry means in the order of the display of the icons, and for enabling a mode in which the user is capable of establishing a specific intent.

* * * * *

UNITED STATES PATENT AND TRADEMARK OFFICE
CERTIFICATE OF CORRECTION

PATENT NO. : 6,426,740 B1
DATED : July 30, 2002
INVENTOR(S) : Hironori Goto et al.

It is certified that error appears in the above-identified patent and that said Letters Patent is hereby corrected as shown below:

<u>Drawings,</u>
Sheet 45, Figure 52, "MORING" should read -- MORNING --.
Sheet 62, Figure 71, "DELETIION" should read -- DELETION --.
Sheet 64, Figure 73, "DELETIION" should read -- DELETION --.

<u>Column 7,</u>
Line 35, "sightly" should read -- slightly --.

<u>Column 10,</u>
Line 67, "|0xd' - xe'|" should read -- | xd' - xe'| --.

<u>Column 33,</u>
Line 20, "exists" should read -- exits --.
Line 42, "exists" should read -- exits --.
Line 66, "exists" should read -- exits --.

<u>Column 34,</u>
Line 16, "exists" should read -- exits --.
Line 18, "corresponds" should read -- correspond --.
Line 26, "exists" should read -- exits --.

<u>Column 35,</u>
Line 11, "exists" should read -- exits --.
Line 33, "exists" should read -- exits --.
Line 43, "$\geq$a" should read -- $\geq$ --.
Line 57, "exists" should read -- exits --.

UNITED STATES PATENT AND TRADEMARK OFFICE
CERTIFICATE OF CORRECTION

PATENT NO. : 6,426,740 B1
DATED : July 30, 2002
INVENTOR(S) : Hironori Goto et al.

It is certified that error appears in the above-identified patent and that said Letters Patent is hereby corrected as shown below:

Column 36,
Line 7, "exists" should read -- exits --.
Line 17, "exists" should read -- exits --.

Column 46,
Line 66, "has is" should read -- has --.

Column 53,
Line 5, "1 or" should read -- 1 and --.
Line 11, "1 or" should read -- 1 and --.
Line 19, "1 or" should read -- 1 and --.

Column 57,
Line 22, "information," should read -- information; --.

Signed and Sealed this

Eighteenth Day of February, 2003

JAMES E. ROGAN
*Director of the United States Patent and Trademark Office*